United States Patent
Gardai et al.

(10) Patent No.: US 11,820,827 B2
(45) Date of Patent: Nov. 21, 2023

(54) METHODS OF TREATING MYELODYSPLASTIC SYNDROME AND ACUTE MYELOID LEUKEMIA WITH NONFUCOSYLATED ANTI-CD70 ANTIBODIES

(71) Applicant: Seagen Inc., Bothell, WA (US)

(72) Inventors: Shyra Gardai, Bothell, WA (US); Phoenix Ho, Bothell, WA (US)

(73) Assignee: SEAGEN INC., Bothell, WA (US)

( * ) Notice: Subject to any disclaimer, the term of this patent is extended or adjusted under 35 U.S.C. 154(b) by 277 days.

(21) Appl. No.: 17/134,963

(22) Filed: Dec. 28, 2020

(65) Prior Publication Data

US 2021/0221897 A1     Jul. 22, 2021

Related U.S. Application Data

(60) Provisional application No. 63/011,906, filed on Apr. 17, 2020, provisional application No. 62/954,904, filed on Dec. 30, 2019.

(51) Int. Cl.
| | |
|---|---|
| C07K 16/28 | (2006.01) |
| A61K 47/68 | (2017.01) |
| A61P 35/00 | (2006.01) |
| A61K 31/47 | (2006.01) |
| A61K 31/496 | (2006.01) |
| A61K 31/706 | (2006.01) |
| A61K 39/395 | (2006.01) |
| A61K 39/00 | (2006.01) |
| A61K 38/07 | (2006.01) |

(52) U.S. Cl.
CPC .......... *C07K 16/2875* (2013.01); *A61K 31/47* (2013.01); *A61K 31/496* (2013.01); *A61K 31/706* (2013.01); *A61K 38/07* (2013.01); *A61K 39/3955* (2013.01); *A61K 47/6803* (2017.08); *A61K 47/6849* (2017.08); *A61P 35/00* (2018.01); *A61K 2039/505* (2013.01); *C07K 2317/21* (2013.01); *C07K 2317/24* (2013.01); *C07K 2317/41* (2013.01); *C07K 2317/732* (2013.01); *C07K 2317/92* (2013.01)

(58) Field of Classification Search
CPC ............ C07K 16/2875; C07K 2317/21; C07K 2317/24; C07K 2317/41; C07K 2317/732; C07K 2317/92; A61K 31/47; A61K 31/496; A61K 31/706; A61K 38/07; A61K 39/3955; A61K 47/6803; A61K 47/6849; A61K 2039/505; A61P 35/00
See application file for complete search history.

(56) References Cited

U.S. PATENT DOCUMENTS

| | | | |
|---|---|---|---|
| 4,474,893 A | 10/1984 | Reading | |
| 4,486,414 A | 12/1984 | Pettit | |
| 4,676,980 A | 6/1987 | Segal et al. | |
| 4,714,681 A | 12/1987 | Reading | |
| 4,816,397 A | 3/1989 | Boss | |
| 4,816,444 A | 3/1989 | Pettit | |
| 4,816,567 A | 3/1989 | Cabilly | |
| 4,879,278 A | 11/1989 | Pettit | |
| 4,925,648 A | 5/1990 | Hansen | |
| 4,946,778 A | 8/1990 | Ladner et al. | |
| 4,978,744 A | 12/1990 | Pettit | |
| 4,986,988 A | 1/1991 | Pettit | |
| 5,076,973 A | 12/1991 | Pettit | |
| 5,122,464 A | 6/1992 | Wilson | |
| 5,138,036 A | 8/1992 | Pettit | |
| 5,155,027 A | 10/1992 | Sledziewski | |
| 5,223,409 A | 6/1993 | Ladner et al. | |
| 5,225,539 A | 7/1993 | Winter | |
| 5,258,498 A | 11/1993 | Huston | |
| 5,336,603 A | 8/1994 | Capon | |
| 5,349,053 A | 9/1994 | Landolfi | |
| 5,359,046 A | 10/1994 | Capon | |
| 5,403,484 A | 4/1995 | Ladner | |
| 5,410,024 A | 4/1995 | Pettit | |
| 5,427,908 A | 6/1995 | Dower | |
| 5,504,191 A | 4/1996 | Pettit | |
| 5,516,637 A | 5/1996 | Huang | |
| 5,521,284 A | 5/1996 | Pettit | |
| 5,530,097 A | 6/1996 | Pettit | |
| 5,530,101 A | 6/1996 | Queen et al. | |
| 5,554,725 A | 9/1996 | Pettit | |
| 5,565,332 A | 10/1996 | Hoogenboom et al. | |
| 5,571,698 A | 11/1996 | Ladner | |
| 5,573,920 A | 11/1996 | Randle | |
| 5,573,924 A | 11/1996 | Beckmann | |
| 5,580,717 A | 12/1996 | Dower | |

(Continued)

FOREIGN PATENT DOCUMENTS

| | | |
|---|---|---|
| EP | 0012023 A1 | 6/1980 |
| EP | 0105360 A1 | 4/1984 |

(Continued)

OTHER PUBLICATIONS

Pohlen M, et al. (Oct. 2016) Haematologica. 101(10):1208-1215. (doi: 10.3324/haematol.2016.147934).*

Adam, P.J. et al. (2006). "CD70 (TNFSF7) Is Expressed At High Prevalence In Renal Cell Carcinomas and Is Rapidly Internalised On Antibody Binding," British J. of Cancer. 95:298-306.

Agathanggelou, A. et al. (Oct. 1995). "Expression of Immune Regulatory Molecules In Epstein-Barr Virus-Associated Nasopharyngeal Carcinomas With Prominent Lymphoid Stroma. Evidence For A Functional Interaction Between Epithelial Tumor Cells and Infiltrating Lymphoid Cells," Am J. Pathol., 147(4):1152-1160.

(Continued)

*Primary Examiner* — Robert S Landsman

(74) *Attorney, Agent, or Firm* — Morrison & Foerster LLP

(57) ABSTRACT

The invention provides methods of treating cancer, such as myeloid malignancies including myelodysplastic syndrome (MDS) and acute myeloid leukemia (AML), with nonfucosylated anti-CD70 antibodies.

22 Claims, 16 Drawing Sheets

Specification includes a Sequence Listing.

(56) References Cited

U.S. PATENT DOCUMENTS

| | | | |
|---|---|---|---|
| 5,585,089 A | 12/1996 | Queen et al. | |
| 5,591,828 A | 1/1997 | Bosslet | |
| 5,599,902 A | 2/1997 | Pettit | |
| 5,601,819 A | 2/1997 | Wong | |
| 5,635,483 A | 6/1997 | Pettit | |
| 5,658,727 A | 8/1997 | Barbas | |
| 5,663,149 A | 9/1997 | Pettit | |
| 5,665,860 A | 9/1997 | Pettit | |
| 5,698,426 A | 12/1997 | Huse | |
| 5,733,743 A | 3/1998 | Johnson et al. | |
| 5,750,753 A | 5/1998 | Kimae | |
| 5,780,225 A | 7/1998 | Wigler | |
| 5,780,588 A | 7/1998 | Pettit | |
| 5,807,715 A | 9/1998 | Morrison | |
| 5,821,047 A | 10/1998 | Garrard | |
| 5,859,205 A | 1/1999 | Adair | |
| 5,969,108 A | 10/1999 | Mccafferty | |
| 6,034,065 A | 3/2000 | Pettit | |
| 6,130,237 A | 10/2000 | Denny | |
| 6,214,345 B1 | 4/2001 | Firestone | |
| 6,239,104 B1 | 5/2001 | Pettit | |
| 6,323,315 B1 | 11/2001 | Pettit | |
| 6,342,219 B1 | 1/2002 | Thorpe | |
| 6,407,213 B1 | 6/2002 | Carter | |
| 6,881,557 B2 | 4/2005 | Foote | |
| 6,884,869 B2 | 4/2005 | Senter | |
| 7,261,892 B2 | 8/2007 | Terrett | |
| 7,351,408 B2 | 4/2008 | Bertozzi | |
| 7,491,390 B2 | 2/2009 | Law | |
| 7,498,298 B2 | 3/2009 | Doronina | |
| 7,641,903 B2 | 1/2010 | Law | |
| 7,659,241 B2 | 2/2010 | Senter | |
| 7,662,387 B2 | 2/2010 | Law | |
| 7,829,531 B2 | 11/2010 | Senter | |
| 7,851,437 B2 | 12/2010 | Senter | |
| 8,067,546 B2 | 11/2011 | Mcdonagh | |
| 8,163,551 B2 | 4/2012 | Alley | |
| 8,337,838 B2 | 12/2012 | Law | |
| 8,562,987 B2 | 10/2013 | Mcdonagh | |
| 8,574,907 B2 | 11/2013 | Alley | |
| 8,609,104 B2 | 12/2013 | Law | |
| 8,663,642 B2 | 3/2014 | Law | |
| 9,051,372 B2 | 6/2015 | Law | |
| 9,051,972 B2 | 6/2015 | Garvey | |
| 9,228,026 B2 | 1/2016 | Smith | |
| 9,428,585 B2 | 8/2016 | Mcdonagh | |
| 9,701,752 B2 | 7/2017 | Mcdonagh | |
| 9,816,069 B2 | 11/2017 | Alley | |
| 10,196,445 B1 | 2/2019 | Engelhardt et al. | |
| 10,443,035 B2 | 10/2019 | Alley | |
| 11,319,526 B2 * | 5/2022 | Alley | C07H 13/04 |
| 2003/0083263 A1 | 5/2003 | Doronina | |
| 2003/0096743 A1 | 5/2003 | Senter | |
| 2003/0105000 A1 | 6/2003 | Pero | |
| 2003/0130189 A1 | 7/2003 | Senter | |
| 2004/0110704 A1 | 6/2004 | Yamane | |
| 2004/0131612 A1 | 7/2004 | Watkins | |
| 2004/0157782 A1 | 8/2004 | Doronina | |
| 2004/0180002 A1 | 9/2004 | Young | |
| 2005/0009751 A1 | 1/2005 | Senter | |
| 2005/0010664 A1 | 1/2005 | Hubbard | |
| 2005/0106644 A1 | 5/2005 | Cairns | |
| 2005/0113308 A1 | 5/2005 | Senter | |
| 2005/0118656 A1 | 6/2005 | Terrett | |
| 2005/0123547 A1 | 6/2005 | Terrett | |
| 2005/0191299 A1 | 9/2005 | Swamy | |
| 2005/0238649 A1 | 10/2005 | Doronina | |
| 2006/0074008 A1 | 4/2006 | Senter | |
| 2006/0083736 A1 | 4/2006 | Law | |
| 2006/0233794 A1 | 10/2006 | Law | |
| 2007/0292422 A1 | 12/2007 | Law | |
| 2008/0025989 A1 | 1/2008 | Law | |
| 2008/0138341 A1 | 6/2008 | Law | |
| 2008/0138343 A1 | 6/2008 | Law | |
| 2008/0226657 A1 | 9/2008 | Doronina | |
| 2008/0241128 A1 | 10/2008 | Jeffrey | |
| 2008/0248051 A1 | 10/2008 | Doronina | |
| 2008/0248053 A1 | 10/2008 | Doronina | |
| 2009/0047296 A1 | 2/2009 | Doronina | |
| 2009/0074772 A1 | 3/2009 | Law | |
| 2009/0148942 A1 | 6/2009 | Mcdonagh | |
| 2009/0317869 A1 | 12/2009 | Alley | |
| 2010/0129362 A1 | 5/2010 | Law | |
| 2010/0150925 A1 | 6/2010 | Law | |
| 2010/0158910 A1 | 6/2010 | Law | |
| 2010/0183636 A1 | 7/2010 | Law | |
| 2012/0045436 A1 | 2/2012 | Mcdonagh | |
| 2012/0183997 A1 | 7/2012 | Alley | |
| 2012/0276086 A1 | 11/2012 | Black et al. | |
| 2012/0294863 A1 | 11/2012 | Law | |
| 2014/0031536 A1 | 1/2014 | Alley | |
| 2014/0178936 A1 | 6/2014 | Mcdonagh | |
| 2015/0337259 A1 | 11/2015 | Alley | |
| 2017/0022282 A1 | 1/2017 | Mcdonagh et al. | |
| 2018/0155677 A1 | 6/2018 | Alley | |
| 2019/0276796 A1 | 9/2019 | Alley | |
| 2019/0284287 A1 | 9/2019 | Goubier et al. | |
| 2019/0352418 A1 * | 11/2019 | Wilson | C07K 16/2896 |

FOREIGN PATENT DOCUMENTS

| | | |
|---|---|---|
| EP | 0173494 A2 | 3/1986 |
| EP | 0184187 A2 | 6/1986 |
| EP | 0217577 A2 | 4/1987 |
| EP | 0239400 A2 | 9/1987 |
| EP | 0171496 A2 | 11/1987 |
| EP | 0367166 A1 | 5/1990 |
| EP | 0404097 A2 | 10/1991 |
| EP | 0519596 A1 | 12/1992 |
| EP | 0592106 A1 | 4/1994 |
| EP | 1176195 A1 | 1/2002 |
| WO | 198303679 A1 | 10/1983 |
| WO | 198601533 A1 | 3/1986 |
| WO | 198605807 A1 | 10/1986 |
| WO | 198702671 A1 | 5/1987 |
| WO | 198901036 A1 | 2/1989 |
| WO | 199002809 A1 | 3/1990 |
| WO | 199100360 A1 | 1/1991 |
| WO | 199109967 A1 | 7/1991 |
| WO | 199110737 A1 | 7/1991 |
| WO | 199201047 A1 | 1/1992 |
| WO | 199205793 A1 | 4/1992 |
| WO | 199208802 A1 | 5/1992 |
| WO | 199218619 A1 | 10/1992 |
| WO | 199308829 A1 | 5/1993 |
| WO | 199311161 A1 | 6/1993 |
| WO | 199311236 A1 | 6/1993 |
| WO | 199317715 A1 | 9/1993 |
| WO | 1994004690 A1 | 3/1994 |
| WO | 199515982 A2 | 6/1995 |
| WO | 199520401 A1 | 8/1995 |
| WO | 199515982 A3 | 12/1995 |
| WO | 199604388 A1 | 2/1996 |
| WO | 199954342 A1 | 10/1999 |
| WO | 200194629 A2 | 12/2001 |
| WO | 2002088172 A2 | 11/2002 |
| WO | 2003026577 A2 | 4/2003 |
| WO | 2003035835 A2 | 5/2003 |
| WO | 2003046581 A2 | 6/2003 |
| WO | 2003035835 A3 | 10/2003 |
| WO | 2004010957 A2 | 2/2004 |
| WO | 2004073656 A2 | 9/2004 |
| WO | 2004073656 A3 | 2/2005 |
| WO | 2005081711 A2 | 9/2005 |
| WO | 2006044643 A2 | 4/2006 |
| WO | 2006089231 A2 | 8/2006 |
| WO | 2006113909 A2 | 10/2006 |
| WO | 2006089231 A3 | 12/2006 |
| WO | 2007011968 A2 | 1/2007 |
| WO | 2007038637 A2 | 4/2007 |
| WO | 2007011968 A3 | 10/2007 |
| WO | 2008074004 A2 | 6/2008 |
| WO | 2009135181 A2 | 11/2009 |

(56) References Cited

FOREIGN PATENT DOCUMENTS

| | | |
|---|---|---|
| WO | 2009135181 A3 | 2/2010 |
| WO | 2018229303 A1 | 12/2018 |
| WO | 2020127503 A1 | 6/2020 |

OTHER PUBLICATIONS

Agematsu, K. et al. (Aug. 1997). "B Cell Subpopulations Separated By CD27 and Crucial Collaboration Of CD27+ B Cells and Helper T Cells In Immunoglobulin Production," Eur. J. Immunol. 27(8):2073-2079. Abstract Submitted.

Agematsu, K. et al. (Jan. 1, 1998). "Generation Of Plasma Cells From Peripheral Blood Memory B Cells: Synergistic Effect Of Interleukin-10 and CD27/CD70 Interaction," Blood 91(1):173-180.

Akewanlop, C. et al. (May 15, 2001). "Phagocytosis of Breast Cancer Cells Mediated by Anti-MUC-1 Monoclonal Antibody, DF3, and Its Bispecific Antibody," Cancer Res. 61:4061-4065.

Akiba, H. et al. (Jan. 17, 2000). "Critical Contribution Of OX40 Ligand To T Helper Cell Type 2 Differentiation In Experimental Leishmaniasis," J. Exp. Med. 191(2):375-380.

Al-Lazikani, B. et al. (1997). "Standard Conformations for the Canonical Structures of Immunoglobulins," J. Mol. Biol 273:927-948.

Altschul, S.F. et al. (Oct. 5, 1990). "Basic Local Alignment Search Tool," J. Mol. Biol. 215(3):403-410.

Altschul, S.F. et al. (Sep. 1, 1997). "Gapped BLAST and PSI-Blast: A New Generation of Protein Database Search Programs," Nucleic Acids Res. 25(17):3389-3402.

Ames, R.S. et al. (Aug. 18, 1995). "Conversion of Murine Fabs Isolated From A Combinatorial Phage Display Library To Full Length Immunoglobulins," J. Immunol. Methods 184(2):177-186.

Arber, D.A. et al. (May 19, 2016). "The 2016 revision to the World Health Organization Classification of Myeloid Neoplasms and Acute Leukemia," Blood 127(20):2391-2405.

Armour, K.L. et al. (1999). "Recombinant Human IgG Molecules Lacking Fcγ Receptor I Binding and Monocyte Triggering Activities," Eur. J. Immunol. 29:2613-2624.

Asseman, C. et al. (Oct. 4, 1999). "An Essential Role for Interleukin 10 in the Function of Regulatory T Cells That Inhibit Intestinal Inflammation," J. Exp. Med. 190(7):995-1004.

Baert, F. et al. (Feb. 13, 2003). "Influence of Immunogenicity on the Long-Term Efficacy of Infliximab in Crogn's Disease," N. Engl. J. Med. 348(7):601-608, 16 pages.

Bahler, D.W. et al. (Aug. 1992). "Clonal Evolution Of a Follicular Lymphoma: Evidence For Antigen Selection," PNAS, 89(15):6770-6774.

Bahler, D.W. et al. (Oct. 1, 1992). "Antigen Selection in Human Lymphomagenesis," Cancer Res., 52(19 Suppl.):5547s-5551s.

Baxevanis, A.D. et al. (Apr. 1993). "Interactions Of Coiled Coils In Transcription Factors: Where Is The Specificity?," Curr. Op. Gen. Devel. 3(2):278-285.

Beidler, C.B. et al. (Dec. 1, 1988). "Cloning and High Level Expression Of A Chimeric Antibody With Specificity For Human Carcinoembryonic Antigen," J. Immunol. 141(11):4053-4060.

Belkaid, Y. (Nov. 2007, e-pub. Oct. 19, 2007). "Regulatory T Cells and Infection: A Dangerous Necessity," Nature Reviews, 2007, 7:875-888.

Bernheim, a. et al. (Mar. 1993). "Cytogenetic Studies In Three Xenografted Nasopharyngeal Carcinomas," Cancer Genet. Cytogenet. 66(1):11-15.

Better, M. et al. (May 20, 1988). "*Escherichia coli* Secretion of An Active Chimerica Antibody Fragment," Science 240:1041-1043.

Bettini, M. et al. (Dec. 2009). "Regulatory T Cells and Inhibitory Cytokines in Autoimmunity," Curr. Opin. Immunol. 21(6):612-618, 12 pages.

Bindon, C.L. et al. (Jul. 1988). "Human Monoclonal IgG Isotypes Differ in Complement Activating Function at the Level of C4 As Well As C1q", J. Exp. Med. 168:127-142.

Bitter, G.A. et al. (1987). "Expression and Secretion Vectors For Yeast," Methods in Enzymol. 153:516-544.

Bohmann, D. et al. (Dec. 4, 1987). "Human Proto-Oncogene c-jun Encodes A DNA Binding Protein With Structural and Functional Properties Of Transcription Factor AP-1," Science 238(4832):1386-1392.

Bowman, M.R. et al. (Feb. 15, 1994). "The Cloning of CD70 and Its Identification as the Ligand for CD27," J. Immunol. 152(4):1756-1761. Abstract Submitted.

Braun, T. et al. (Feb. 1, 2003, e-pub. Oct. 13, 2005). "NF-κB Constitutes a Potential Therapeutic Target in High-Risk Myelodysplastic Syndrome," Blood 107(3):1156-1165.

Brinkmann, U. et al. (May 11, 1995). "Phage Display Of Disulfide-Stabilized Fv Fragments," J. Immunol. Methods 182(1):41-50.

Brugnoni, D. et al. (1997). "CD70 Expression On T-Cell Subpopulations: Study Of Normal Individuals and Patients With Chronic Immune Activation," Immunol. Lett. 55(2):99-104.

Burgess, W.H. et al. (1990). "Possible Dissociation Of The Heparin-Binding And Mitogenic Activities Of Heparin-Binding (Acidic Fibroblast) Growth Factor-1 From Its Receptor-Binding Activities By Site-Directed Mutagenesis Of A Single Lysine Residue," J. Cell Biol. 111:2129-2138.

Burton, D.R. et al. (1994). "Human Antibodies From Combinatorial Libraries," Advances in Imniunology 57:191-280.

Cao, Z. et al. (1991). "Regulated Expression of Three C/EBP Isoforms During Adipose Conversion of 3T3-L1 Cells," Genes & Development 5:1538-1552.

Carter, P. et al. (Feb. 1992). "High Level *Escherichia coli* Expression and Production of a Bivalent Humanized Antibody Fragment," Bio/Technology 10:163-167.

Carter, P. et al. (Nov. 2001). "Improving the Efficacy of Antibody-Based Cancer Therapies," Nature Reviews, (1):118-129.

Carter, P. et al. (Oct. 1995). Toward The Production Of Bispecific Antibody Fragments For Clinical Applications. J. Hematotherapy 4:463-470.

Casset, F. et al. (2003) "A Peptide Mimetic Of An Anti-CD4 Monoclonal Antibody By Rational Design," BBRC 307:198-205.

Chari, R.V.J. et al. (Jan. 1, 1992). "Immunoconjugates Containing Noveal maytansinoids: Promissing Anticancer Drugs," Cancer Res. 52:127-131.

Chen, C. et al. (1995). "Enhancement and Destruction Of Antibody Function By Somatic Mutation: Unequal Occurrence Is Controlled By V Gene Combinatorial Associations," EMBO 14 (12):2784-2794.

Chen, F.-M et al. (2001). "Potentiation of Antitumor Immunity By Antibody-Directed Enzyme Prodrug Therapy," Int. J. Cancer 94(6):850-858.

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Cheson, B.D. (Dec. 15, 2003). "Revised Recommendations of the International Working Group for Diagnosis, Standardization of Response Criteria, Treatment Outcomes, and Reporting Standard for Therapeutic Trials in Acute Myeloid Leukemia," J Clin Oncol 21(24):4642-4649. Abstract Submitted.

Cheson, B.D. et al. (Jul. 15, 2006, e-pub. Apr. 11, 2006). "Clinical Application and Proposal for Modification of the International Working Group (IWG) Response Criteria in Myelodysplasia," Blood 108(2):419-425.

Chothia, C. et al. (1987). "Canonical Structures for the Hypervariable Regions of Immunoglobulins," J. Mol. Biol. 196:901-917.

Chothia, C. et al. (Dec. 5, 1985). "Domain Association In Immunoglobulin Molecules. The Packing Of Variable Domains," J. Mol. Biol. 186(3):651-663.

Clackson, T. et al. (Aug. 15, 1991). "Making Antibody Fragments Using Phage Display Libraries," Nature 352:624-628.

Claessens, Y.-E. et al. (Mar. 1, 2002). "In Vitro Proliferation and Differentiation of Erythroid Progenitors From Patients With Myelodysplastic Syndromes: Evidence For Fas-Dependent Apoptosis," Blood 99(5):1594-1601.

Claessens, Y.-E. et al. (May 15, 2005, e-pub. Jan. 27, 2005). "Rescue of Early-Stage Myelodysplastic Syndrome-Deriving Erythroid

(56) References Cited

OTHER PUBLICATIONS

Precursor by the Ectopic Expression of a Dominatnt-Negative Form of FADD," Blood 105(10):4035-4042.
Cockett, M.I. et al. (Jul. 1990). "High Level Expression Of Tissue Inhibitor Of Metalloproteinases In Chinese Hamster Ovary Cells Using Glutamine Synthetase Gene Amplification," Bio/Technology 8(7):662-667 (Jul. 1990).
Cohen, L. (Feb. 1987). "Optimization Of Dose-Time Factors For a Tumor And Multiple Associated Normal Tissues," Int. J. Radiat. Oncology. Biol. Phys. 13(2):251-258. Abstract Submitted.
Colbère-Garapin, F. et al. (Jul. 25, 1981). "A New Dominant Hybrid Selective Marker For Higher Eukaryotic Cells," .J. Mol. Biol. 150(1):1-14.
Collison, L.W. et al. (2009). "Regulatory T Cell Suppression is Potentiated by Target T Cells in a Cell Contact, IL-35-and IL-10-Dependent Manner," J. Immunol. 182:6121-6128.
Collison, L.W. et al. (2011). "In Vitro Treg Suppression Assays," Methods Molecular Biology 707:21-37, 18 pages.
Colman, P.M. (1994). "Effects Of Amino Acid Sequence Changes On Antibody-Antigen Interactions," Research in Immunology 145(1):33-36.
Crouse, G.F. et al. (Feb. 1983). "Expression and Amplification Of Engineered Mouse Dihydrofolate Reductase Minigenes," Mol. Cell. Biol. 3:257-266.
Dannull, J. et al. (Dec. 2005). "Enhancement of Vaccine-Mediated Antitumor Immunity in Cancer Patients After Depletion of Regulatory T Cells," J Clin Invest 115(12):3623-3633.
Davis, R.L. et al. (Mar. 9, 1990). "The MyoD DNA Binding Domain Contains A Recognition Code For Muscle-Specific Gene Activation," Cell 60(5):733-746.
De Jong, R. et al. (Apr. 15, 1991). "Regulation of Expression of CD27, A T Cell-Specific Member of a Novel Family of Membrane Receptors," J. Immunol. 146(8):2488-2494.
De Pascalis, R. et al. (2002) "Grafting of "Abbreviated" Complementarity-Determining Regions Containing Specificity-Determining Residues Essential for Ligand Contact to Engineer a Less Immunogenic Humanized Monoclonal Antibody," J Immunol. 169:3076-3084.
Den Haan, J.M. et al. (Jun. 9, 1995). "Identification of a Graft Versus Host Disease-Associated Human Minor Histocompatibility Antigen," Science 268(5216):1476-1480. Abstract Submitted.
Dieckmann, D. et al. (Jun. 4, 2001). "Ex Vivo Isolation and Characterization of CD4+ CD25+ T Cells with Regulatory Properties from Human Blood," J. Exp. Med. 193(11):1303-1310.
Dillman, R.O. (Oct. 1989). "Monoclonal Antibodies for Treating Cancer", Ann. Int. Med., 111:592-603.
Doronina, S.O. et al. (Aug. 2003). "Erraturm: Development of Potent Monoclonal Antibody Auristatin Conjugates for Cancer Therapy," Nat. Biotechnol. 21(8):941.
Ebert, B.L. et al. (Jan. 17, 2008). "Identification of RPS14 as a 5q-Syndrome Gene by RNA Interference Screen," Nature 451(7176), p. 335-339, 11 pages.
Emery, S.C. et al. (1994). "Humanised Monoclonal Antibodies For Therapeutic Applications," Exp. Opin. Invest. Drugs, 3(3):241-251.
Foecking, M.K. et al. (1986). "Powerful and Versatile Enhancer-Promoter Unit For Mammalian Expression Vectors," Gene 45(1):101-105.
Freshney, R.I. et al. (1983). "Culture of Animal Cells," Chapter 1 in A Manual of Basic Technique, Alan R. Liss, Inc., New York, NY, pp. 1-6.
Gillies, S.D. et al. (Dec. 20, 1989). "High-Level Expression Of Chimeric Antibodies Using Adapted cDNA Variable Region Cassettes," J. Immunol. Methods 125(1-2):191-202.
Giralt, S.A. et al. (Dec. 1, 1994). "Leukemia Relapse After Allogeneic Bone Marrow Transplantation: A Review," Blood 84(11):3603-3612.
Goodwin, R.G. et al. (May 7, 1993). "Molecular and Biological Characterization of a Ligand for CD27 Defines a New Family of Cytokines with Homology to Tumor Necrosis Factor," Cell 73(3):447-456. Abstract Submitted.

Gordon, K.A. et al. (Apr. 2006). "Humanized Anti-CD70 Auristatin Antibody-Drug Conjugates Show Potent In Vitro Cytotoxicity in Renal Cell Carcinoma Primary Cultures Established from Patient Tumor Isolates," Abstract No. 3733, 97th Annual Meeting of the American Association for Cancer Research, Apr. 1-5, 2006, Washington, D.C., 4 pages.
Gravestein, L.A. et al. (1995). "Novel mAbs Reveal Potent Co-Stimulatory Activity of Murine CD27," Int. Immunol, 7(4):551-557.
Gravestein, L.A. et al. (Apr. 1993). "Cloning and Expression of Murine CD27: Comparison With 4-1BB, Another Lymphocyte-Specific Member of The Nerve Growth Factor Receptor Family," Eur. J. Immunol. 23(4):943-950. Abstract Submitted.
Grewal, I.S. (Mar. 2008). "CD70 as a Therapeutic Target In Human Malignancies," Expert Opin. Ther. Targets 12(3):341-351. Abstract Submitted.
Gruss, H.J. et al. (Sep. 1996). "Pathophysiology of Hodgkin's Disease: Functional and Molecular Aspects," Baillieres Clin. Haematol. 9(3):417-446. Abstract Submitted.
Gura, T. (1997). "Systems for identifying new drugs are often faulty," Science 278(5340):1041-1042.
Hai, T. et al. (May 9, 1991). "Cross-family Dimerization Of Transcription Factors Fos/Jun and ATF/CREB Alters DNA Binding Specificity," Proc. Natl. Acad. Sci. USA 88(9):3720-3724.
Hai, T.W. et al. (Dec. 1989). "Transcription Factor ATF cDNA Clones: An Extensive Family Of Leucine Zipper Proteins Able To Selectively Form DNA-Binding Heterodimers," Genes Dev. 3(12B):2083-2090.
Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.
Held-Feindt, J. et al. (2002). "CD70/CD27 Ligand, A Member of The TNF Family, Is Expressed In Human Brain Tumors," Int. J. Cancer 98(3):352-356.
Hieter, P.A. et al. (Feb. 10, 1982). "Evolution Of Human Immunoglobulin Kappa J Region Genes," J. Biol. Chem. 257(3):1516-1522.
Higgins, D.G. et al. (1996). "Using CLUSTAL For Multiple Sequence Alignments," Methods Enzyniol. 266:383-402.
Hintzen, R.Q. et al. (1994). "Characterization of the Human CD27 Ligand, A Novel Member of the TNF Gene Family," J. Immunol. 152(4):1762-1773.
Hintzen, R.Q. et al. (Jul. 1, 1991). "A Soluble Form of The Human T Cell Differentiation Antigen CD27 Is Released After Triggering of The TCR/CD3 Complex," J. Immunol. 147(1):29-35. Abstract Submitted.
Hintzen, R.Q. et al. (Jul. 1994). "CD27: Marker and Mediator of T-Cell Activation?", Immunol. Today, 15(7):307-311. Abstract Submitted.
Hintzen, R.Q. et al. (Mar. 15, 1995). "Engagement of CD27 With Its Ligand CD70 Provides a Second Signal for T Cell Activation," J. Immunol. 154(6):2612-2623. Abstract Submitted.
Hintzen, R.Q. et al. (Mar. 1994). "CD70 Represents The Human Ligand For CD 27," Int. Immunol. 6(3):477-480. Abstract Submitted.
Hintzen, R.Q. et al. (Sep. 1, 1993). "Regulation of CD27 Expression on Subsets of Mature T-Lymphocytes," J. Immunol. 151(5):2426-2435. Abstract Submitted.
Hishima, T. et al. (May 2000). "CD70 Expression In Thymic Carcinoma," Am. J. Surg. Pathol. 24(5):742-746. Abstract Submitted.
Holliger, P. et al. (Jul. 1993), "Diabodies': Small Bivalent and Bispecific Antibody Fragments," Proc. Natl. Acad. Sci. USA 90:6444-6448.
Holliger, P. et al. (Sep. 2005). "Engineered Antibody Fragments and The Rise of Single Domains," Nat. Biotechnol. 23(9):1126-1136.
Holm, P. et al. (Feb. 2007). "Functional Mapping and Single Chain Construction Of The Anti-Cytokeratin 8 Monoclonal Antibody TS1," Mol. Immunol. 44(6):1075-1084.
Honegger, A. et al. (Jun. 8, 2001). "Yet Another Numbering Scheme For Immunoglobulin Variable Domains: An Automatic Modeling And Analysis Tool," J. Mol. Biol. 309:657-670.

(56) References Cited

OTHER PUBLICATIONS

Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.

Huston, J.S. et al. (1991). "Protein Engineering Of Single-Chain Fv Analogs and Fusion Proteins," Methods in Enzymology 203:46-88.

Inn List 69 (2013). WHO Drug Information 27(1):85-87, 3 pages.

Inouye, S. et al. (May 10, 1985). "Up-Promoter Mutations In The Ipp Gene Of *Escherichia coli*," Nucleic Acids Res. 13(9):3101-3109.

Iwahashi, M. et al. (Oct.-Nov. 1999). "CDR Substitutions of a Humanized Monoclonal Antibody (CC49): Contributions of Individual CDRs to Antigen Binding and Immunogenicity," Mol. Immunol. 36(15-16):1079-1091.

Jacquot, S. et al. (Sep. 15, 1997). "CD154/CD40 and CD70/CD27 Interactions Have Different and Sequential Functions in T Cell-Dependent B Cell Responses: Enhancement of Plasma Cell Differentiation by CD27 Signaling," J. Immunol. 159(6):2652-2657. Abstract Submitted.

Jefferis, R. et al. (Jul./Aug. 2009). "Human Immunoglobulin Allotypes," MABS 1(4):1-7.

Jeffrey, S.C. et al. (May-Jun. 2006, e-pub. May 3, 2006). "Development and Properties of Beta-Glucuronide Linkers for Monoclonal Antibody-Drug Conjugates," American Chemical Society 17(3):A-J.

Jones, P. et al. (May 29, 1986). "Replacing The Complementarity-Determining Regions In A Human Antibody With Those From A Mouse," Nature 321:522-525.

Karlin, S. et al. (Jun. 1993). "Applications and Statistics For Multiple High-Scoring Segments In Molecular Sequences," Proc. Natl. Acad. Sci. USA 90:5873-5877.

Karlin, S. et al. (Mar. 1990). "Methods For Assessing The Statistical Significance Of Molecular Sequence Features By Using General Scoring Schemes," Proc. Natl. Acad. Sci. USA 87(6):2264-2268.

Keler, T. et al. (Jun. 1, 2000). "Differential Effect Of Cytokine Treatment On Fcα Receptor I-and Fcγ receptor I-Mediated Tumor Cytotoxicity By Monocyte-Derived Macrophages," J. Immunol. 164(11):5746-5752.

Kettleborough, C. et al. (1991). "Humanization of a Mouse Monoclonal Antibody By CDR-Grafting: The Importance Of Framework Residues On Loop Conformation," Protein Eng. 4(7):773-783.

Kettleborough, C.A. et al. (Apr. 1994). "Isolation Of Tumor Cell-Specific Single-Chain Fv From Immunized Mice Using Phage-Antibody Libraries And The Re-Construction Of Whole Antibodies From These Antibody Fragments," Eur. J. Immunol. 24(4):952-958.

Kim, J. et al. (Dec. 15, 2009). "Cutting Edge: Depletion of Foxp3+ Cells Leads to Induction of Autoimmunity by Specific Ablation of Regulatior T Cells in Genetically Targeted Mice," J. Immunol. 183(12):7631-7634.

Kim, J.M. et al. (Feb. 2007, e-pub. Nov. 30, 2006). "Regulatory T Cells Prevent Catastrophic Autoimmunity Throughout the Lifespan of Mice," Nat. Immunol. 8(2):191-197. Abstract Submitted.

Klussman, K. et al. (2008, e-pub. Apr. 1, 2008). "Immune Modulation Mediated by the Humanized Anti-CD70 Monoclonal Antibody SGN-70," Experimental Biology, San Diego, California, Apr. 5-9, 2008. Abstract Submitted.

Knoll, K. et al. (Nov. 1, 2000). "Targeted Therapy of Experimental Renal Cell Carcinoma with a Novel Conjugate of Monoclonal Antibody 138H11 and Calicheamicin 0111," Cancer Research 60:6089-6094.

Kobata, T. et al. (Nov. 1995). "CD27-CD70 Interactions Regulate B-Cell Activation By T Cells," PNAS 92(24):11249-11253.

Kohler, G. et al. (Aug. 7, 1975). "Continuous Culture of Fused Cells Secreting Antibody of Predefined Specificity," Nature 256:495-497.

Kostelny, S.A. et al. (Mar. 1, 1992). "Formation of a Bispecific Antibody By The Use of Leucine Zippers," J. Immunol. 148(5):1547-1553.

Kussie, P.H. et al. (1994). "A Single Engineered Amino Acid Substitution Changes Antibody Fine Specificity", J. Immunol. 152:146-152.

Köhler, G. (Apr. 1980). "Immunoglobulin Chain Loss In Hybridorna Lines," Proc. Natl. Acad.Sci. USA 77(4):2197-2199.

Landschulz, W.H. et al. (Jun. 24, 1988). "The Leucine Zipper: A Hypothetical Structure Common To A New Class of DNA Binding Proteins," Science 240(4860):1759-1764.

Larrick, J.W. et al. (Jul. 1980). "Characterization Of A Human Macrophage-Like Cell Line Stimulated in vitro: A Model Of Macrophage Functions," J. Immunology 125(1):6-12.

Law, C.-L et al. (Mar. 2009). "Novel Antibody-Based Therapeutic Agents Targeting CD70: A Potential Approach For Treating Waldenstrom's Macroglobulinemia," Clinical Lymphoma & Myeloma 9(1 ):90-93.

Law, C.-L. et al. (May 2005). "Anti-CD70 Antibody Drug Conjugates Mediate Renal Carcinoma Cell Killing Through Cytotoxic Drug Delivery Antibody-Dependent Cellular Cytotoxicity (abstract only)", Proc Amer Assoc Cancer Res. 46:6143, 3 pages.

Law, C.L. et al. "Lymphocyte Activation Antigen CD70 Expressed by Renal Cell Carcinoma Is a Potential Therapeutic Target for Anti-CD70 Antibody-Drug Conjugates," Cancer Res., 2006; 66(4):2328-2337.

Lazar et al., "Transforming Growth Factor A: Mutation Of Aspartic Acid 47 and Leucine 48 Results In Different Biological Activities," Mol. Cell. Biol. 8:1247-1252, (1988).

Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.

Lens, S.M. et al. "Control of Lymphocyte Function Through CD27-CD70 Interactions," Semin Immunol. 10(6):491-499 Abstract Submitted. (Dec. 1998).

Lens, S.M. et al. (Dec. 1996). "Phenotype and Function of Human B Cells Expressing CD70 (CD27 ligand)," Eur. J. Immunol., 26(12):2964-2971, Abstract Submitted.

Lens, S.M.A. et al. (1997). "Antigen-Presenting Cell-Derived Signals Determine Expression Levels of CD70 On Primed T Cells," Immunol. 90:38-45.

Lens, S.M.A. et al. (Dec. 1998). "Aberrant Expression and Reverse Signaling of CD70 On Malignant B Cells," Br. J. Haematol. 106(2):491-503.

Liu, A.Y. et al. (May 1987). "Chimeric Mouse-Human IGG1 Antibody That Can Mediate Lysis of Cancer Cells," Proc Natl Acad Sci 84(1):3439-3443.

Liu, A.Y. et al. (Nov. 15, 1987). "Production of a Mouse-Human Chimeric Monoclonal Antibody to CD20 With Potent Fc-Dependent Biologic Activity," J Immunol. 139(10):3521-3526.

Locksley, R.M. et al. (Feb. 23, 2001). "The TNF and TNF Receptor Superfamilies: Integrating Mammalian Biology," Cell 104(4):487-501.

Logan, J. et al. (Jun. 1984). "Adenovirus Tripartite Leader Sequence Enhances Translation Of Mrnas Late After Infection," Proc. Nati. Acad. Sci. USA 81(12):3655-3659.

MacCallum, R.M. et al. (1996). "Antibody-Antigen Interactions: Contact Analysis and Binding Site Topography," J. Mol. Biol. 262:732-745.

Manocha, M. et al. (2009). "Blocking CD27-CD70 Costimulatory Pathway Suppresses Experimental Colitis," J. Immunol 183:270-276.

Marks, J.D. et al. (1991). "By-Passing Immunization: Human Antibodies From V-Genen Libraries Displayed on Phage," J. Mol. Biol. 222:581-597.

Martin, A.C.R. et al. (Dec. 1989). "Modeling Antibody Hypervariable Loops: A Combined Algorithm," Pnas USA 86(23):9268-9272.

Mattila, P.S. et al. (Sep. 1995). "Extensive Allelic Sequence Variation In The J Region Of The Human Immunoglobulin Heavy Chain Gene Locus," Eur. J. Immunol. 25(9):2578-2582.

Maurer, D. et al. (Dec. 1990). "CD27 Expression By a Distinct Subpopulation of Human B Lymphocytes," Eur. J. Immunol. 20(12):2679-2684. Abstract Submitted.

McEarchern, J.A. et al. (Dec. 1, 2008). "Preclinical Characterization of SGN-70, A Humanized Antibody Directed Against CD70," Clin. Cancer Res. 14(23):7763-7772.

(56) References Cited

OTHER PUBLICATIONS

McEarchern, J.A. et al. (May 2005). "Engineered Anti-CD70 Antibody Variants Support Multiple Effector Functions and Exhibit Potent In Vitro and In Vivo Antitumor Activities (abstract only)," Proc Amer Assoc Cancer Res. 46:6142, 4 pages.
McEarchern, J.A. et al. (Nov. 1, 2006). "SGN-70, A Humanized Anti-CD70 Antibody, Target CD70-Expressing Hematologic Tumors," ASH, Orlando, Florida, Dec. 9-12, 2006. 108(11):2492, 5 pages. Abstract Submitted.
Merchant, A. M. et al. (Jul. 1998). "An Efficient Route To Human Bispecific IgG," Nature Biotechnology 16:677-681.
Milstein, C. et al. (Oct. 6, 1983). "Hybrid Hybridomas and Their Use In Immunohistochemistry," Nature 305:537-540.
Morrison, S.L. (1992). "In Vitro Antibodies: Strategies for Production and Application," Annual Rev Immunol 10(1):239-265. Abstract Submitted.
Morrison, S.L. (Sep. 1985). "Transfectomas Provide Novel Chimeric Antibodies," Science 229(4719):1202-1207.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Munn, D.H. et al. (Jul. 1, 1990). "Phagocytosis Of Tumor Cells By Human Monocytes Cultured In Recombinant Macrophage Colony-Stimulating Factor," J. Exp. Med. 172(1):231-237.
Murre, C. et al. (Mar. 10, 1989). "A New DNA Binding and Dimerization Motif In Immunoglobulin Enhancer Binding, daughterless, MyoD, and myc Proteins," Cell 56(5):777-783.
Nakajima, A. et al. (Feb. 1, 1997). "Roles of IL-4 and IL-12 In The Development Of Lupus In NZB/WF1 Mice," J. Immunol. 158(3):1466-1472. Abstract Submitted.
Nakajima, A. et al. (Sep. 22, 2000). "Involvement of CD70-CD27 Interactions In The Induction of Experimental Autoimmune Encephalomyelitis," J. Neuroimmunol. 109(2):188-196. Abstract Submitted.
Nicolaou, K.C. et al. (1994). "Calicheamicin 011 : A Rationally Designed Molecule with Extremely Potent and Selective DNA Cleaving Properties and Apoptosis Inducing Activity," Angew. Chem. Intl. Ed. Engl. 33(2):183-186.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
O'Shea, E.K. et al. (Jan. 27, 1989). "Evidence That The Leucine Zipper Is A Coiled Coil," Science 243(4890):538-542.
Oelke, K. et al. (Jun. 2004). "Overexpression of CD70 and Overstimulation of IgG Synthesis by Lupus T Cells and T Cells Treated With DNA Methylation Inhibitors," Arthritis & Rheumatism, 50(6):1850-1860.
Oflazoglu, E. et al. (2009). "Blocking of CD27-CD70 Pathway by Anti-CD70 Antibody Ameliorates Joint Disease in Murine Collagen-Induced Arthritis." J Immunol 183:3770-3777.
Oflazoglu, E. et al. (Apr. 2006). "In Vivo Characterization of the Mechanism of Action of c1 F6, an Anti-CD70 Antibody," Abstract No. 3732, 97th Annual Meeting of the American Association for Cancer Research, Apr. 1-5, 2006, Washington, D.C., 3 pages.
Oi, V.T. et al. (1986). "Chimeric Antibodies," Bio Techniques 4(3):214-219.
Orengo, A.M. et al. (1997). "Reciprocal Expression of CD70 and of Its Receptor, CD27, In Human Long Term-Activated T and Natural Killer (NK) Cells: Inverse Regulation By Cytokines and Role In Induction Ofcytotoxicity," Clin. Exp. Immunol., 107(3):608-613.
Oshima, H. et al. (1998). "Characterization of Murine CD70 By Molecular Cloning and mAb," Int. Immunol. 10(4):517-526.
Padlan, E.D. (1991). "A Possible Procedure for Reducing the Immunogenicity of Antibody Variable Domains While Preserving Their Ligand-Binding Properties," Mol. Immunol. 28(4/5):489-498.
Pearson, W.R. et al. (Apr. 1988). "Improved Tools For Biological Sequence Comparison," Proc. Natl. Acad. Sci. USA 85(8):2444-2448.
Peitsch et al., "Comparative Molecular Modeling Of The Fas-Ligand And Other Members Of The TNF Family," Mol. Immunol. 32(10):761-772 (1995).
Pereira, N.A. et al. (Jul. 2018). "The 'Less-is-More' in Therapeutic Antibodies: Afucosylated Anti-Cancer Antibodies With Enhanced Antibody-Dependent Cellular Cytotoxicity," MAbs 10(5):693-711.
Persic, L. et al. (Mar. 10, 1997). "An Integrated Vector System For The Eukaryotic Expression Of Antibodies Or Their Fragments After Selection From Phage Display Libraries," Gene 187(1):9-18.
Perussia, B. et al. (2000). "Assays For Antibody-Dependent Cell-Mediated Cytotoxicity (ADCC) and Reverse ADCC (Redirected Cytotoxicity) In Human Natural Killer Cells," Methods in Molecular Biology 121:179-192.
Plückthun, A. (1994) "Antibodies from *Escherichia coli*," Chapter 11 in Handbook of Experimental Pharmacology 113:269-315.
Proudfoot, N.J. (Aug. 7, 1986). "Transcriptional Interference and Termination Between Duplicated A-Globin Gene Constructs Suggests A Novel Mechanism For Gene Regulation," Nature 322:562-565.
Quan, et al. (2002). "The Rise Of Monoclonal Antibodies As Therapeutics," in Anti-IgE and Allergic Disease, Jardieu and Fick Jr., eds., Marcel Dekker, New York, NY, Chapter 20, pp. 427-469.
Ramos, F. et al. (Mar. 1999). "Myelodysplastic Syndrome: A Search for Minimal Diagnostic Criteria," Leuk. Res. 23(3):283-290.
Ranheim, E.A. et al. (1995). "Expression of CD27 and Its Ligand, CD70, On Chronic Lymphocytic Leukemia B Cells," Blood 85(12):3556-3565.
Reff, M.E. et al. (Mar./Apr. 2002). "Future of Monoclonal Antibodies in the Treatment of Hematologic Malignancies," Cancer Control. 9(2):152-166.
Reichmann, L. et al. (Mar. 1988). "Reshaping Human Antibodies for Therapy," Nature 332:323-327.
Rodrigues, M.L. et al. (Dec. 15, 1993). "Engineering Fab' Fragments For Efficient F(ab)2 Formation In *Escherichia coli* and For Improved In Vivo Stability," J. Immunology 151(12):6954-6961.
Roguska, M.A. et al. (Feb. 1994). "Humanization Of Murine Monoclonal Antibodies Through Variable Domain Resurfacing," Proc. Natl. Acad. Sci. USA 91(3):969-973.
Roman, C. et al. (Aug. 1990). "Ig/EBP-1: A Ubiquitously Expressed Immunoglobulin Enhancer Binding Protein That Is Similar To C/EBP and Heterodimerizes With C/EBP," Genes Dev. 4(8):1404-1415.
Rudikoff, S. et al. (Mar. 1982). "Single Amino Acid Substitution Altering Antigen-Binding Specificity," Proc. Natl. Acad. Sci. USA 79:1979-1983.
Rüther, U. et al. (1983). "Easy Identification of cDNA Clones," EMBO 2(10):1791-1794.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).
Sambrook, J. et al. (2001). Molecular Cloning: A Laboratory Manual Cold Spring Harbor Laboratory Press, Cold Spring Harbor,N. Y., 3rd ed., 1 page, Table of Contents.
Schnell, R. et al. (2002). "Current Strategies of Antibody-Based Treatment in Hodgkin's Disease," Annals of Oncology 13(1):57-66.
Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.
Shields, R.L. et al. (Jul. 26, 2002, e-pub. May 1, 2002). "Lack of Fucose on Human IgG1 N-Linked Oligosaccharide Improves Binding to Human FcγRIII and Antibody-dependent Cellular Toxicity," J. Biol. Chem. 277:26733-26740.
Shin, E.K. et al. (Dec. 1991). "Physical Map Of The 3' Region Of The Human Immunoglobulin Heavy Chain Locus: Clustering Of Autoantibody-Related Variable Segments In One Haplotype," EMBO J. 10(12):3641-3645.
Shu, L. et al. (Sep. 1, 1993). "Secretion Of A Single-Gene-Encoded Immunoglobulin From Myeloma Cells," Proc. Natl. Acad. Sci. USA 90(17):7995-7999.
Silence, K. et al. (Mar./Apr. 2014). "ARGX-110, A Highly Potent Antibody Targeting CD70, Eliminates Tumors Via Both Enhanced ADCC and Immune Checkpoint Blockage," mABS 6(2):523-532.

(56) References Cited

OTHER PUBLICATIONS

Skerra, A. et al. (May 20, 1988). "Assembly Of A Functional Immunoglobulin Fv Fragment In *Escherichia coli*," Science 240(4855):1038-1041.
Skolnick, J. et al. (Jan. 2000). "From Genes To Protein Structure and Function: Novel Applications of Computational Approaches In The Genomic Era," Trends in Biotechnology 18:34-39.
Smith, C.A. et al. (au 25, 1990). "A Receptor For Tumor Necrosis Factor Defines An Unusual Family of Cellular and Viral Proteins," Science 248(4958):1019-1023. Abstract Submitted.
Stella, V.J. et al. (1985). "Prodrugs: A Chemical Approach to Targeted Drug Delivery," in Directed Drug Delivery, pp. 247-267.
Studnicka, G.M. et al. (Jun. 1994). "Human-Engineered Monoclonal Antibodies Retain Full Specific Binding Activity By Preserving Non-CDR Complementarity-Modulating Residues," Protein Engineering 7(6):805-814. Abstract Submitted.
Sugita, K. et al. (Aug. 15, 1992). "Participation of the CD27 Antigen In The Regulation of IL-2-Activated Human Natural Killer Cells," J. Immunol. 149(4):1199-1203. Abstract Submitted.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Suresh, M.R. et al. (1986). "Bispecific Monoclonal Antibodies From Hybrid Hybridomas," Methods in Enzymology 121:210-228, 19 pages.
Takahashi, T. et al. (1998). "Immunologic Self-Tolerance Maintained by CD25+Cd4+ Naturally Anergic and Suppressive T Cells: Induction of Autoimmune Disease by Breaking Their Anergic/Suppressive State," Int. Immunol. 10(12):1969-1980.
Tamura, M. et al. (Feb. 2000). "Structural Correlates of an Anticarcinoma Antibody: Identification of Specificity-Determining Residues (SDRs) and Development of a Minimally Immunogenic Antibody Variant by Retention of SDRS Only," J. Immunol. 164(3):1432-1441.
Tang, Q. et al. (Mar. 2008). "The Foxp3+ Regulatory T Cell: A Jack of All Trades, Master of Regulation," Nature Immunology 9(3):239-244, 13 pages.
Tarentino, A.L. et al. (Dec. 16, 1975). "The Isolation and Structure of the Core Oligosaccharide Sequences of IgM," Biochemistry 14(25):5516-5523. Abstract Submitted.
Tesselaar, K. et al. (1997). "Characterization of Murine CD70, The Ligand of The TNF Receptor Family Member CD27," J. Immunol. 159(10):4959-4965.
Tesselaar, K. et al. (Jan. 2003, e-pub. Dec. 9, 2002), "Lethal T Cell Immunodeficiency Induced By Chronic Costimulation Via CD27-CD70 Interactions," Nature Immunol 4(1):49-54.
Thornton, A.M. et al. (Jul. 20, 1998). "CD4+CD25+ Immunoregulatory T Cells Suppress Polyclonal T Cell Activation in Vitro by Inhibiting Interleukin 2 Production," J. Exp. Med. 188(2):287-296.
Tiu, R. et al. (Aug. 2007, e-pub. Jun. 7, 2007). "Clonality of the Steam Cell Compartment During Evolution of Myelodysplastic Syndromes and Other Bone Marrow Failure Syndromes," Leukemia 21(8):1648-1657.
Torelli, A. et al. (Feb. 1994). "ADVANCE and ADAM: Two Algorithms For The Analysis Of Global Similarity Between Homologous Informational Sequences," Comput. Appl. Biosci. 10(1):3-5.
Traunecker, A. et al. (1991). "Bispecific Single Chain Molecules (Janusins) Target Cytotoxic Lymphocytes on HIV Infected Cells," EMBO J. 10(12):3655-3659.
Tsaknaridis, L. et al. (Oct. 15, 2003). "Functional Assay for Human CD4+CD25+ Treg Cells Reveals an Age-Dependent Loss of Suppressive Activity," J Neurosci Res. 74(2):296-308.
Tsuchiya, S. et al. (Aug. 1980). "Establishment and Characterization Of A Human Acute Monocytic Leukemia Cell Line (THP-1)," Int. J.Cancer 26(2):171-176.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

U.S. Appl. No. 11/833,954, filed Aug. 3, 2007, Doronina et al. (Copy not submitted herewith pursuant to the waiver of 37 C.F.R. § 1.98(a)(2)(iii) issued by the Office on Sep. 21, 2004).
U.S. Appl. No. 12/265,451, filed Nov. 5, 2008, Hsu et al. (Copy not submitted herewith pursuant to the waiver of 37 C.F.R. § 1.98(a)(2)(iii) issued by the Office on Sep. 21, 2004).
U.S. Appl. No. 60/449,055, filed Feb. 20, 2003, Law et al. (Copy not submitted herewith pursuant to the waiver of 37 C.F.R. § 1.98(a)(2)(iii) issued by the Office on Sep. 21, 2004).
Uchida, J. et al. (Jun. 21, 2004). "The Innate Mononuclear Phagocyte Network Depletes B Lymphocytes Through Fc Receptor-Dependent Mechanisms During Anti-CD20 Antibody Immunotherapy," J. Exp. Med. 199(12):1659-1669.
Umaña, P. et al. (Feb. 1999). "Engineered Glycoforms of an Antineuro- Blastoma IgG 1 With Optimized Antibody-Dependent Cellular Cytotoxic Activity," Nat. Biotechnol. 17:176-180.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Van Heeke, G. et al. (1989). "Expression of Human Asparagine Synthetase in *Escherichia coli*," J. Biol. Chem. 24:5503-5509.
Van Lier, R.A.W. et al. (Sep. 1, 1987). "Tissue Distribution and Biochemical and Functional Properties of Tp55 (CD27), A Novel T Cell Differentiation Antigen," J. Immunol. 139(5):1589-1596.
Verhoeyen, M. et al. (Mar. 25, 1988). "Reshaping Human Antibodies: Grafting An Antilysozyme Activity," Science 239(4857):1534-1536.
Vinson, C.R et al. (Nov. 17, 1989). "Scissors-Grip Model For DNA Recognition By A Family Of Leucine Zipper Proteins," Science 246(4932):911-916.
Voronova, A. et al. (Jun. 1990). "Mutations That Disrupt DNA Binding and Dimer Formation In The E47 Helix-Loop-Helix Protein Map To Distinct Domains," Proc. Natl. Acad. Sci. USA 87(12):4722-4726.
Watanabe, M. et al. (Feb. 1999). "Antibody Dependent Cellular Phagocytosis (ADCP) and Antibody Dependent Cellular Cytotoxicity (ADCC) of Breast Cancer Cells Mediated By Bispecific Antibody, MDX-210," Breast Cancer Res. Treat. 53(3):199-207.
White, C.A. et al. (2001). "Antibody-Targeted Immunotherapy For Treatment of Malignancy," Annual Review of Medicine 52:125-145. Abstract Submitted.
Williams, S.C. et al. (Sep. 1991). "A Family of C/EBP-Related Proteins Capable Of Forming Covalently Linked Leucine Zipper Dimers In Vitro," Genes Dev. 5(9):1553-1567.
Wilman, D.E.V. (1986). "Prodrugs in Cancer Chemotherapy", in Biochemical Society Transactions, 14:375-382.
Wilson, I.A. et al. (Jul. 1984). "The Structure Of An Antigenic Determinant In A Protein," Cell 37:767-778.
Winkler, K. et al. (2000). "Changing the Antigen Binding Specificity by Single Point Mutations of an Anti-p24 (HIV-1 antibody)", J. Immunol. 165(16):4505-4514.
Wischhusen, J. et al. (May 1, 2002). "Identification of CD70-Mediated Apoptosis of Immune Effector Cells as a Novel Immune Escape Pathway of Human Gliblastoma," Cancer Res. 62:2592-2599.
Witzig, T.W. (Aug. 2001). "Radioimmunotherapy For Patients With Relapsed B-Cell Non-Hodgkin Lymphoma," Cancer Chemother. Pharmacol. 48(suppl. 1):S91-S95. Abstract Submitted.
Wood, C.R. et al. (Apr. 4, 1985). "The Synthesis and in vivo Assembly of Functional Antibodies In Yeast," Nature 314(6010):446-449.
Workman, C.J. et al. (2011). "In Vivo Treg Suppression Assays," Method Molcular Biology 707:119-156, 30 pages.
Wu, H. (2003). "Simultaneous Humanization and Affinity Optimization of Monoclonal Antibodies," Methods in Mol. Biol. 207:197-212.
Wu, H. et al. (1999). "Humanization for a Murine Monoclonal Antibody by Simultaneous Optimization of Framework and CDR Residues," J. Mol. Biol. 19:294(1):151-162.
Yamane-Ohunuki, N. et al. (Sep. 5, 2004, e-pub. Aug. 6, 2004). "Establishment of FUT8 Knockout Chinese Hamster Ovary Cells: An Ideal Host Cell Line for Producing Completely Defucosylated

(56) References Cited

OTHER PUBLICATIONS

Antibodies With Enhanced Antibody-Dependent Cellular Cytotoxicity," Biotechnol. Bioeng. 87(5):614-622.
Zapata, G. et al. (1995). "Engineering Linear F(ab')2 Fragments For Efficient Production In *Escherichia coli* And Enhanced Antiproliferative Activity," Protein Engineering 8(10):1057-1062.
Zips, D. et al. (2005). "New Anticancer Agents: In Vitro and In Vivo Evaluation," In Vivo 19:1-8.
Aribi, A. et al. (Nov. 5, 2020). "A Phase 1 Study of Sea-CD70 in Myeloid Malignancies," Blood 136(Supp. 1):23-24.
Diolaiti, D. et al. (Nov. 5, 2020). "Potential of Sea-CD70 for the Treatment of Myeloid Leukemia," Blood 136(Supp. 1):23, 2 pages.
Drachman, J.G0 et al. (Nov. 6-11, 2010). "SGN-70: Phase 1a Study of a Novel Humanized Antibody Targeting CD70 for the Treatment of Autoimmune Diseases." American College of Rheumatology, Abstract No. 1273, Atlanta, Georgia, (poster), 1 page.
International Preliminary Report on Patentability, dated Jul. 5, 2022, for PCT Application No. PCT/US2020/067173, 9 pages.
International Search Report and Written Opinion, dated Apr. 9, 2021, for PCT Application No. PCT/US2020/067173, 19 pages.
Janeway, C.A. et al. (2001). "Chapter 3—Antigen Recognition by B-Cell and T-Cell Receptors," Immunobiology, pp. 93-122.
Law, C.-L. et al. (Oct. 2005). "Anti-CD70 Auristatin Conjugates with Potent and Selective Activity Against Renal Cell Carcinoma," poster presentation, 4th International Kidney Cancer Symposium, Oct. 21-23, 2005, Chicago, I, 1 page.
McEarchern, J. (2005). "Antitumor Activities of Engineered Anti-CD70 Antibody (h1F6)," Presentation by Seattle Genetics at Annual Meeting of American Association for Cancer Research Apr. 16-20, 15 pages.
McEarchern, J.A. et al. (Novemver 16, 2005). "A Humanized Anti-CD70 Monoclonal Antibody Targets CD70-Expressing Multiple Myeloma," Abstract 1591, 47th Annual Meeting and Exposition of The American Society of Hematology, Dec. 10-13, 2005, Atlanta, Georgia, Blood 106(11):1591, 2 pages.
McEarchern, J.A. et al. (Oct. 24-29, 2008). "Targeting CD70 for the Treatment of Autoimmune Disorders," ACR, San Francisco, California, Oct. 24-29, 2008 , Abstract 1845, 6 pages.
Oflazoglu, E. et al. (Jun. 7, 2008). "Inhibition of Collagen-Induced Arthritis by an Antibody Targeting CD70," FOCIS 2008, Boston, MA, 127:S80-S123, Poster, 1 page.
Riether, C. et al. (Nov. 13, 2019). "The Combination of the BCL-2 Antagonist Venetoclax With the CD70-Targeting Antibody Cusatuzumab Synergistically Eliminates Primary Human Leukemia Stem Cells," Blood 134(Supp. 1):3918, 5 pages.
Stein, H. et al. (1989). "A5-Cluster Report: CDw70," pp. 446-449 in Leucocyte Typing IV White Cell Differentiation Antigens, Knapp, eds., Oxford University Press, 6 pages.

* cited by examiner

| Probe | Analyte | $K_D$ (nM) |
|---|---|---|
| 37 C SEA h1F6 E133368-01 | hCD70 Biotin E131664-01 | 0.24 |
| 37 C WT h1F6 E133368-03 | hCD70 Biotin E131664-01 | 0.23 | h1F6 WT hFcγR 1 — 0.00066 µM (0.66 nM)
hFcγR 2a H131 — 2.6 µM
hFcγR 2a R131 — 4.5 µM
hFcγR 3a F158 — 5.3 µM

| Probe | $K_D$ (µM) | $k_a$ 1/(Ms) | $k_d$ 1/s |
|---|---|---|---|
| hFcγR 1 | 0.00066 (0.66 nM) | 7.7E+05 | 5.1E-04 |
| hFcγR 2a H131 | 2.6 | 1.0E+05 | 2.7E-01 |
| hFcγR 2a R131 | 4.5 | 7.7E+04 | 3.4E-01 |
| hFcγR 3a F158 | 5.3 | 2.7E+04 | 1.4E-01 |
| hFcγR 3a V158 | 0.86 | 4.6E+04 | 4.0E-02 |
| hFcγR 2b | 25 | 2.6E+04 | 6.7E-01 |
| hFcRN pH 6.09 | 0.017 (17 nM) | 7.2E+05 | 1.2E-02 |
| hFcRN pH 7.46 | 15 | 4.2E+04 | 6.2E-01 | h1F6 SEA hFcγR 1 — 0.00042 µM (0.42 nM)
hFcγR 2a H131 — 3.5 µM
hFcγR 2a R131 — 3.6 µM
hFcγR 3a F158 — 0.53 µM

| Probe | $K_D$ (µM) | $k_a$ 1/(Ms) | $k_d$ 1/s |
|---|---|---|---|
| hFcγR 1 | 0.00042 (0.42 nM) | 1.0E+06 | 4.2E-04 |
| hFcγR 2a H131 | 3.5 | 9.1E+04 | 3.2E-01 |
| hFcγR 2a R131 | 3.6 | 9.4E+04 | 3.4E-01 |
| hFcγR 3a F158 | 0.53 | 1.6E+05 | 8.6E-02 |
| hFcγR 3a V158 | 0.11 | 2.1E+05 | 2.2E-02 |
| hFcγR 2b | 27 | 2.5E+04 | 6.8E-01 |
| hFcRN pH 6.09 | 0.019 (19 nM) | 6.6E+05 | 1.2E-02 |
| hFcRN pH 7.46 | 16.7 | 4.3E+04 | 7.1E-01 |

FIG. 1

| $k_a$ 1/(Ms) | $k_d$ 1/s | $\chi^2$ | $K_D$ error | $k_a$ Error | $k_d$ Error |
|---|---|---|---|---|---|
| 2.6E+05 | 6.2E-05 | 1.7 | 1.24E-12 | 5.77E+02 | 2.94E-07 |
| 2.7E+05 | 6.3E-05 | 2.8 | 1.57E-12 | 7.83E+02 | 3.88E-07 | h1F6 WT

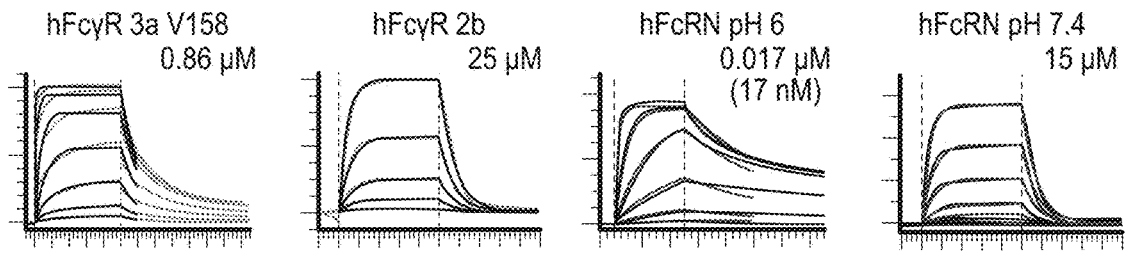

hFcγR 3a V158 0.86 µM | hFcγR 2b 25 µM | hFcRN pH 6 0.017 µM (17 nM) | hFcRN pH 7.4 15 µM

| Probe | $\chi^2$ | $K_D$ error | $k_a$ Error | $k_d$ Error |
|---|---|---|---|---|
| hFcγR 1 | 0.2 | 1.90E-12 | 1.92E+03 | 7.31E-07 |
| hFcγR 2a H131 | 0.3 | 1.53E-07 | 5.37E+03 | 6.45E-03 |
| hFcγR 2a R131 | 0.1 | 2.21E-07 | 3.55E+03 | 6.41E-03 |
| hFcγR 3a F158 | 0.1 | 8.62E-08 | 3.96E+02 | 9.22E-04 |
| hFcγR 3a V158 | 1.3 | 1.73E-08 | 8.00E+02 | 3.93E-04 |
| hFcγR 2b | 0.0 | 1.29E-06 | 1.32E+03 | 7.77E-03 |
| hFcRN pH 6.09 | 0.6 | 3.15E-10 | 1.12E+04 | 1.17E-04 |
| hFcRN pH 7.46 | 0.1 | 9.58E-07 | 2.66E+03 | 1.12E-02 | h1F6 SEA

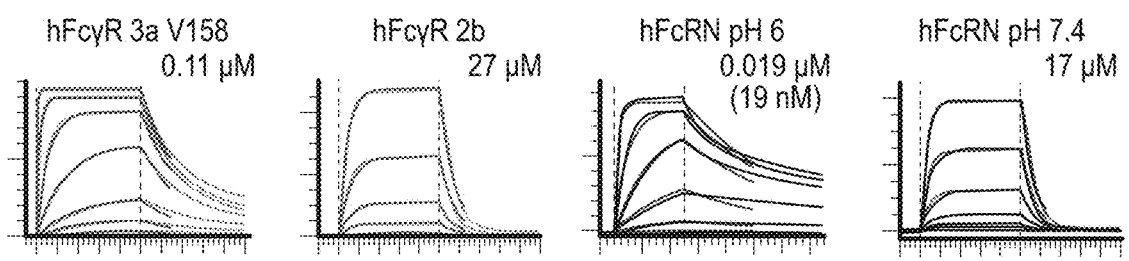

hFcγR 3a V158 0.11 µM | hFcγR 2b 27 µM | hFcRN pH 6 0.019 µM (19 nM) | hFcRN pH 7.4 17 µM

| Probe | $\chi^2$ | $K_D$ error | $k_a$ Error | $k_d$ Error |
|---|---|---|---|---|
| hFcγR 1 | 0.2 | 1.44E-12 | 2.84E+03 | 7.84E-07 |
| hFcγR 2a H131 | 0.3 | 2.28E-07 | 5.34E+03 | 9.26E-03 |
| hFcγR 2a R131 | 0.1 | 2.23E-07 | 5.19E+03 | 9.23E-03 |
| hFcγR 3a F158 | 0.2 | 7.86E-09 | 2.13E+03 | 5.99E-04 |
| hFcγR 3a V158 | 0.4 | 9.69E-10 | 1.68E+03 | 1.02E-04 |
| hFcγR 2b | 0.0 | 1.99E-06 | 1.79E+03 | 1.24E-02 |
| hFcRN pH 6.09 | 0.7 | 3.15E-10 | 9.63E+03 | 1.10E-04 |
| hFcRN pH 7.46 | 0.0 | 1.01E-06 | 2.48E+03 | 1.26E-02 |

FIG. 1 (Cont.)

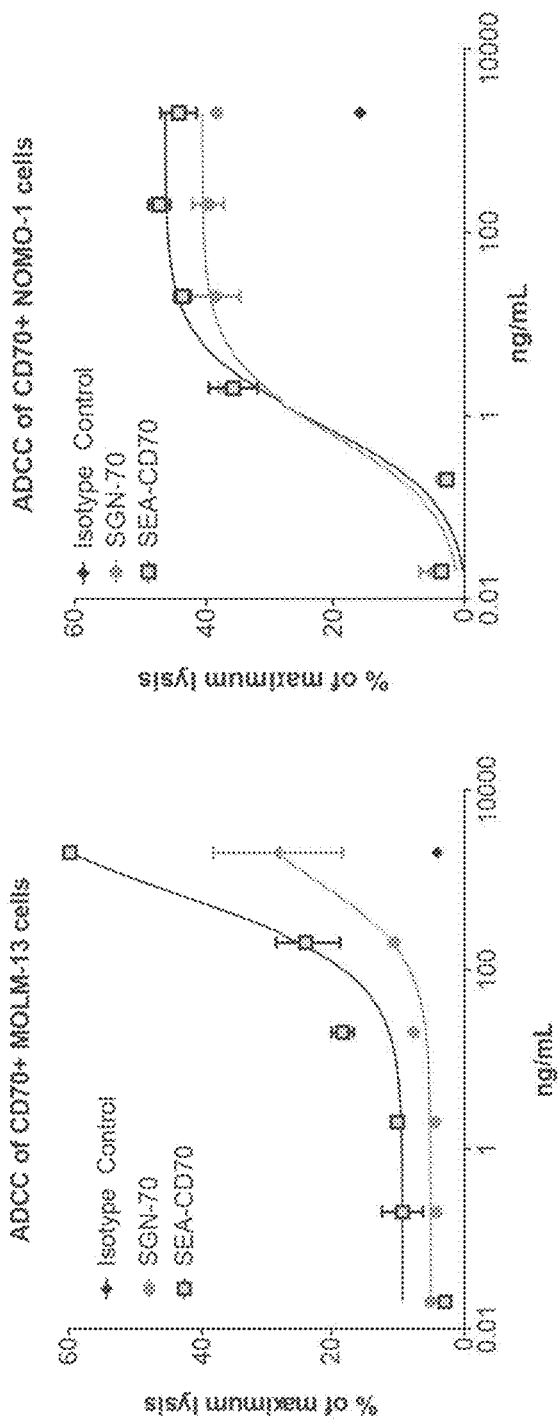
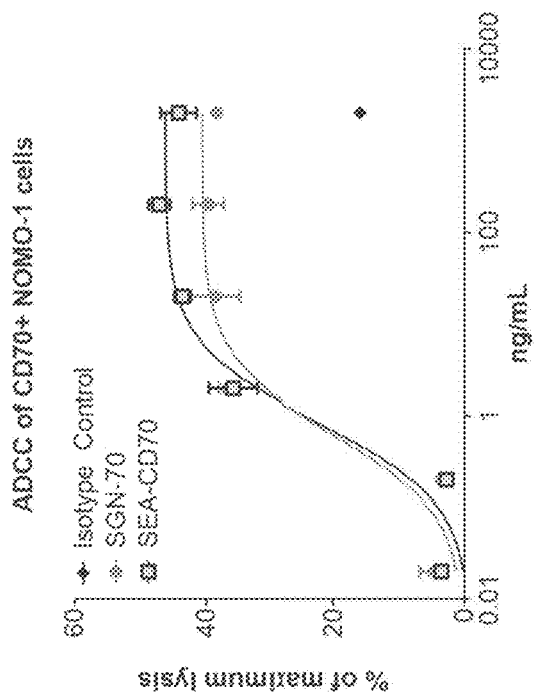
FIG. 3A
FIG. 3B

V/V FcγRIIIα donor

V/V FcγRIIIα donor

F/F FcγRIIIα donor

F/F FcγRIIIα donor

V/V FcγRIIIα donor

V/V FcγRIIIα donor

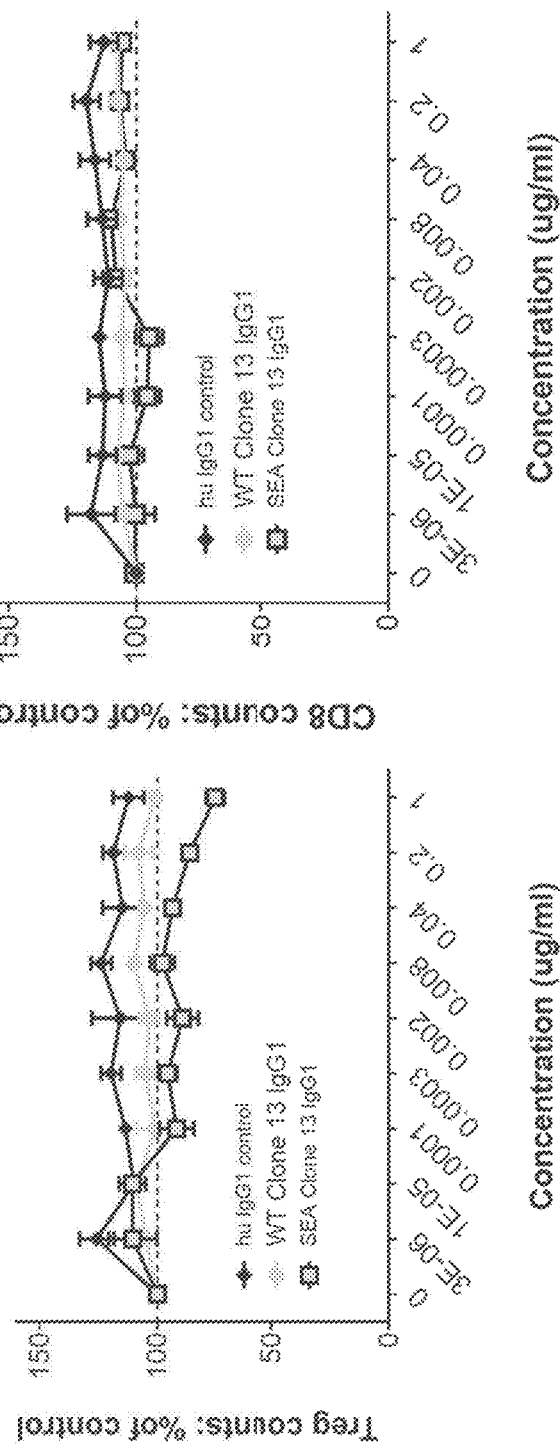
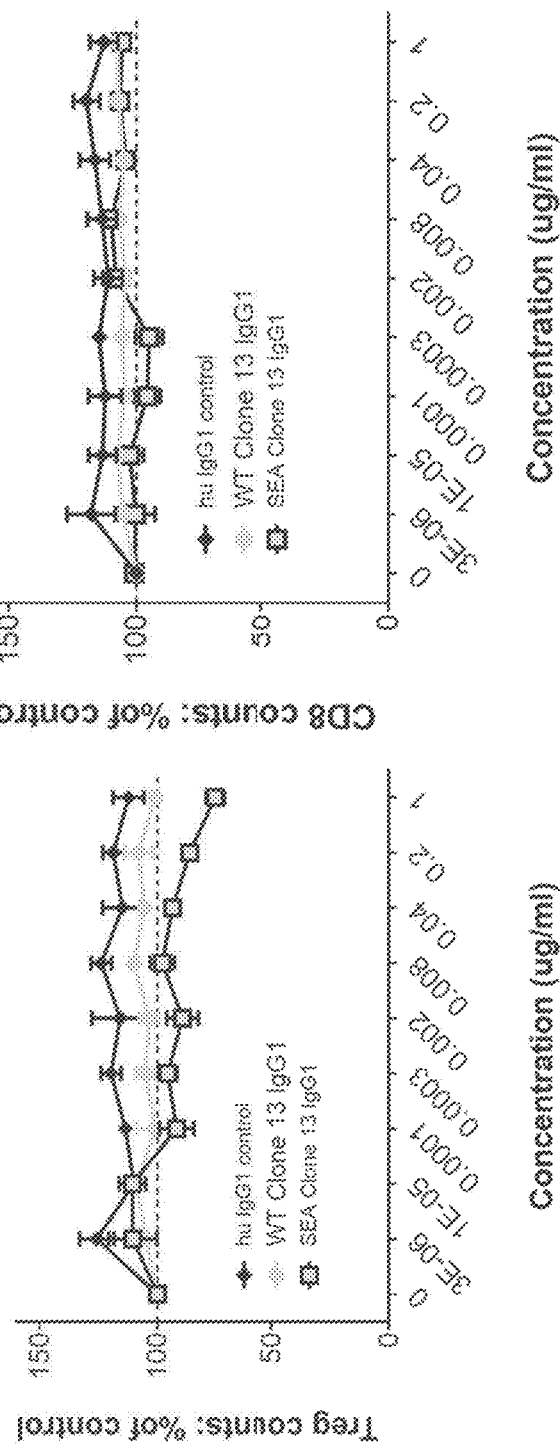
FIG. 4G
FIG. 4H

METHODS OF TREATING MYELODYSPLASTIC SYNDROME AND ACUTE MYELOID LEUKEMIA WITH NONFUCOSYLATED ANTI-CD70 ANTIBODIES

CROSS-REFERENCE TO RELATED APPLICATIONS

This application claims priority to U.S. Provisional Application No. 62/954,904 filed Dec. 30, 2019 and U.S. Provisional Application No. 63/011,906 filed Apr. 17, 2020 the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761682003100SEQLIST.TXT, date recorded: Dec. 22, 2020, size: 13 KB).

TECHNICAL FIELD

The present invention relates to methods of treating cancer, such as myeloid malignancies including myelodysplastic syndrome (MDS) and acute myeloid leukemia (AML), with nonfucosylated anti-CD70 antibodies.

BACKGROUND

CD70 is a member of the tumor necrosis factor (TNF) family of cell membrane-bound and secreted molecules that are expressed by a variety of normal and malignant cell types. The primary amino acid (AA) sequence of CD70 predicts a transmembrane type II protein with its carboxyl terminus exposed to the outside of cells and its amino terminus found in the cytosolic side of the plasma membrane (Bowman et al., 1994, *J. Immunol.* 152:1756-61; Goodwin et al., 1993, *Cell* 73:447-56). Human CD70 is composed of a 20 AA cytoplasmic domain, an 18 AA transmembrane domain, and a 155 AA extracytoplasmic domain with two potential N-linked glycosylation sites (Bowman et al., supra; Goodwin et al., supra). Specific immunoprecipitation of radioisotope-labeled CD70-expressing cells by anti-CD70 antibodies yields polypeptides of 29 and 50 kDa (Goodwin et al., supra; Hintzen et al., 1994, *J. Immunol.* 152:1762-73). Based on its homology to TNF-alpha and TNF-beta, especially in structural strands C, D, H and 1, a trimeric structure is predicted for CD70 (Petsch et al., 1995, *Mol. Immunol.* 32:761-72).

Original immunohistological studies revealed that CD70 is expressed on germinal center B cells and rare T cells in tonsils, skin, and gut (Hintzen et al., 1994, *Int. Immunol.* 6:477-80). Subsequently, CD70 was reported to be expressed on the cell surface of recently antigen-activated T and B lymphocytes, and its expression wanes after the removal of antigenic stimulation (Lens et al, 1996, *Eur. J. Immunol.* 26:2964-71; Lens et al., 1997, *Immunology* 90:38-45). Within the lymphoid system, activated natural killer cells (Orengo et al., 1997, *Clin. Exp. Immunol.* 107:608-13) and mouse mature peripheral dendritic cells (Akiba et al., 2000, *J. Exp. Med.* 191:375-80) also express CD70. In non-lymphoid lineages, CD70 has been detected on thymic medullar epithelial cells (Hintzen et al., 1994, supra; Hishima et al., 2000, *Am. J. Surg Pathol.* 24:742-46).

CD70 is not expressed on normal non-hematopoietic cells. CD70 expression is mostly restricted to recently antigen-activated T and B cells under physiological conditions, and its expression is down-regulated when antigenic stimulation ceases. Evidence from animal models suggests that CD70 may contribute to immunological disorders such as, e.g., rheumatoid arthritis (Brugnoni et al., 1997, *Immunol. Lett.* 55:99-104), psoriatic arthritis (Brugnoni et al., 1997, *Immunol. Lett.* 55:99-104), and lupus (Oelke et al., 2004, *Arthritis Rheum.* 50:1850-60). In addition to its potential role in inflammatory responses, CD70 is also expressed on a variety of transformed cells including lymphoma B cells, Hodgkin's and Reed-Sternberg cells, malignant cells of neural origin, and a number of carcinomas. Studies have shown that stem cells from acute myeloid leukemia (AML) and myelodysplastic disease (MDS) patients express both CD70 and its receptor, CD27. Interactions between this ligand-receptor pair may promote leukemia blast survival and proliferation.

Monoclonal antibodies produced in mammalian host cells can have a variety of post-translational modifications, including glycosylation. Monoclonal antibodies, such as IgG1 s, have an N-linked glycosylation site at asparagine 297 (Asn297) of each heavy chain (two per intact antibody). The glycans attached to Asn297 on antibodies are typically complex biantennary structures with very low or no bisecting N-acetylglucosamine (bisecting GlcNAc) with low amounts of terminal sialic acid and variable amounts of galactose. The glycans also usually have high levels of core fucosylation. Reduction of core fucosylation in antibodies has been shown to alter Fc effector functions, in particular Fcgamma receptor binding and ADCC activity. This observation has led to interest in the engineering cell lines so they produce antibodies with reduced core fucosylation.

Methods for engineering cell lines to reduce core fucosylation include gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knock out gene expression entirely.

Alternatives to engineering cell lines include the use of small molecule inhibitors that act on enzymes in the glycosylation pathway. Inhibitors such as catanospermine act early in the glycosylation pathway, producing antibodies with immature glycans (e.g., high levels of mannose) and low fucosylation levels. Antibodies produced by such methods generally lack the complex N-linked glycan structure associated with mature antibodies. Small molecule fucose analogs can also be used to generate recombinant antibodies that have complex N-linked glycans, but have reduced core fucosylation.

There is a need for anti-CD70 antibodies, such as anti-CD70 antibodies with reduced core fucosylation that can exert a clinically useful cytotoxic, cytostatic, or immunomodulatory effect on CD70-expressing cells, particularly without exerting undesirable effects on non-CD70-expressing cells. Such compounds would be useful therapeutic agents against cancers that express CD70.

Myeloid malignancies include Acute Myeloid leukemia (AML), Myeloproliferative disorders (MPDS), myelodysplastic syndrome (MDS) and myelodysplastic/myeloproliferative syndromes that are all clonal stem-cell (HSC) or progenitor malignant disorders (TIU et al., *Leukemia*, vol. 21(8), p: 1648-57, 2007).

MDS encompasses multiple subtypes, including MDS with single-lineage dysplasia, MDS with ring sideroblasts, MDS with multilineage dysplasia, MDS with excess blasts, MDS with isolated del(5q), and MDS, unclassifiable (ARBER et al., *Blood*, vol. 127, p: 2391-405, 2016). MDS is characterized by ineffective hematopoiesis in one or more of the lineage of the bone marrow. Early MDS mostly demonstrates excessive apoptosis and hematopoietic cell dysplasia (CLAESSENS et al., *Blood*, vol. 99, p: 1594-601, 2002; CLASESSENS et al., *Blood*, vol. 105, p: 4035-42, 2005). In about a third of MDS patients, this ineffective hematopoiesis precedes progression to secondary AML (sAML). Although some molecular events associated with specific MDS subtypes (ELBERT et al., *Nature*, vol. 451 (7176), p: 335-9, 2008) or disease transformation (BRAUN et al. *Blood*, vol. 107(3), p: 1156-65, 2006) have been identified, the underlying molecular defects are still poorly understood. No biological markers, except morphological features, are currently available for early diagnosis and prognosis.

Acute myeloid leukemia (AML) is a malignant tumor of the myeloid lineage of white blood cells. This blood stasis formation is usually fatal blood and bone marrow disease within weeks to months if left untreated. There are 30,000 AMLs in the United States and 47,000 AML estimates in the European Union (2010 prevalence data confirmed by Mattson-Jack, 2010). AML is the most prevalent form of adult acute leukemia (about 90%) and contains about 33% of new leukemia cases. The median age of patients diagnosed with AML was 67 years. In the United States, AML accounts for approximately 1.2% of cancer deaths.

AML causes non-specific symptoms such as weight loss, fatigue, fever and night sweats. AML is diagnosed by blood tests, bone marrow tests, and laboratory tests to determine AML subtypes and to determine treatment decisions.

All references cited herein, including patent applications, patent publications, and scientific literature, are herein incorporated by reference in their entirety, as if each individual reference were specifically and individually indicated to be incorporated by reference.

SUMMARY

Provided herein is a method of treating a CD70-expressing cancer in a subject, the method comprising administering to the subject a therapeutically effective amount of a nonfucosylated anti-CD70 antibody, wherein the method results in a depletion of cancer cells in the subject, wherein the method does not result in a depletion of CD70+ T regulatory cells (CD70+ Tregs) in the subject, wherein the anti-CD70 antibody comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, and wherein the cancer is selected from the group consisting of myelodysplastic syndrome (MDS) and acute myeloid leukemia (AML). In some embodiments, the anti-CD70 antibody comprises a heavy chain variable region comprising an amino acid sequence at least 85% identical to the amino acid sequence of SEQ ID NO:1 and a light chain variable region comprising an amino acid sequence at least 85% identical to the amino acid sequence of SEQ ID NO:2. In some embodiments, the anti-CD70 antibody a heavy chain variable region comprising the amino acid sequence of SEQ ID NO:1 and a light chain variable region comprising the amino acid sequence of SEQ ID NO:2. In some embodiments, the Fc domain is an antibody effector domain mediating one or more of antibody-dependent cellular cytotoxicity (ADCC), antibody-dependent cellular phagocytosis (ADCP), and complement-dependent cellular cytotoxicity (CDC). In some embodiments, the Fc domain is an antibody effector domain mediating ADCC. In some embodiments, the Fc domain is a human Fc domain. In some embodiments, the anti-CD70 antibody is vorsetuzumab. In some embodiments, the antibody is conjugated to a therapeutic agent. In some embodiments, the therapeutic agent is a chemotherapeutic agent or an immunomodulatory agent. In some embodiments, the therapeutic agent is a chemotherapeutic agent. In some embodiments, the chemotherapeutic agent is monomethyl auristatin E (MMAE) or monomethyl auristatin F (MMAF). In some embodiments, the method comprises administering a population of anti-CD70 antibodies, wherein each antibody in the population of anti-CD70 antibodies comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, wherein at least 50% of the anti-CD70 antibodies in the population of the anti-CD70 antibodies lack core fucosylation. In some embodiments, at least 70% of the anti-CD70 antibodies in the population of the anti-CD70 antibodies lack core fucosylation. In some embodiments, at least 90% of the anti-CD70 antibodies in the population of the anti-CD70 antibodies lack core fucosylation. In some embodiments, the cancer is MDS. In some embodiments, the MDS is relapsed or refractory MDS. In some embodiments, the subject experienced treatment failure after prior hypomethylating agent (HMA) therapy for the MDS. In some embodiments, the cancer is AML. In some embodiments, the AML is relapsed or refractory AML. In some embodiments, the subject received 2 prior treatment regimens to treat the AML. In some embodiments, the subject received 3 prior treatment regimens to treat the AML. In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cancer cells express CD70. In some embodiments, administering the nonfucosylated anti-CD70 antibody to the subject results in a depletion of cancer cells by at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or about 100% compared to the amount of cancer cells before administering the nonfucosylated anti-CD70 antibody to the subject. In some embodiments, administering the nonfucosylated anti-CD70 antibody to the subject results in a depletion of CD70+ Tregs of no more than about 20%, about 10%, about 9%, about 8%, about 7%, about 6%, about 5%, about 4%, about 3%, about 2%, about 1%, or about 0.1% compared to the amount of CD70+ Tregs before administering the afucosylated anti-CD70 antibody to the subject. In some embodiments, one or more therapeutic effects in the subject is improved after administration of the nonfucosylated anti-CD70 antibody relative to a baseline. In some embodiments, the one or more therapeutic effects is selected from the group consisting of: objective response rate, duration of response, time to response, progression free survival and overall survival. In some embodiments, the objective response rate is at least about 20%, at least about 25%, at least about 30%, at least about 35%, at least about 40%, at least about 45%, at least about 50%, at least about 60%, at least about 70%, or at least about 80%. In some embodiments, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the nonfucosylated anti-CD70 antibody. In some embodiments, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the nonfucosylated anti-CD70 antibody. In some embodiments, the duration of response to the anti-CD70 antibody is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the nonfucosylated anti-CD70 antibody. In some embodiments, the route of administration for the anti-CD70 antibody is intravenous. In some embodiments, the subject is a human. In some embodiments, the anti-CD70 antibody is administered in combination with azacitidine. In some embodiments, the anti-CD70 antibody is administered in combination with venetoclax. In some embodiments, the anti-CD70 antibody is administered in combination with azacitidine and venetoclax. In some embodiments, the anti-CD70 antibody is administered in combination with fluoroquinalone.

Also provided herein is a pharmaceutical composition for the treatment of a CD70-expressing cancer, the composition comprising a nonfucosylated anti-CD70 antibody, wherein the anti-CD70 antibody comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, and at least one pharmaceutically compatible ingredient, wherein the composition is for use in the method of any of the embodiments herein.

Also provided herein is a kit comprising a nonfucosylated anti-CD70 antibody, wherein the anti-CD70 antibody comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, and instructions for using the anti-CD70 antibodies in the method of any of the embodiments herein.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1 is a series of sensograms of SGN-70 (fucosylated h1F6) and SEA-CD70 (nonfucosylated h1F6) binding to various Fcγ receptors. SGN-70 is labeled as h1F6 WT and SEA-CD70 is labeled as h1F6 SEA in FIG. 1. Biolayer interferometry (BLI) was used to assess the binding kinetics and affinity of SGN-70 and SEA-CD70 to FcγR I, IIa, IIIa, IIb, and FcRN.

FIG. 3A-3B is a series of graphs showing the ADCC activity of SGN-70 and SEA-CD70 in two CD70+ AML cell lines, MOLM-13 (FIG. 3A) and NOMO-1 (FIG. 3B).

FIG. 4E-4H is a series of graphs assessing the impact of fucosylated (WT Clone 13 IgG1) or nonfucosylated (SEA Clone 13 IgG1) anti-TIGIT antibodies on Tregs and CD8 T cells in cells from donors homozygous for high affinity FcγRIIIa receptor (V/V 158) or homozygous for low affinity FcγRIIIa receptor (F/F 158).

FIG. 11A: mean tumor volume (±SEM) is reported for each treatment arm. For each treatment group, data are plotted until the first animal in each group was sacrificed for reaching a tumor size >1000 mm$^3$. FIG. 11B: Single animal growth curves for control, azacitidine+venetoclax, and SEA-CD70+azacitidine+venetoclax combination (triplet combination).

DETAILED DESCRIPTION

I. Definitions

Figure 2A:
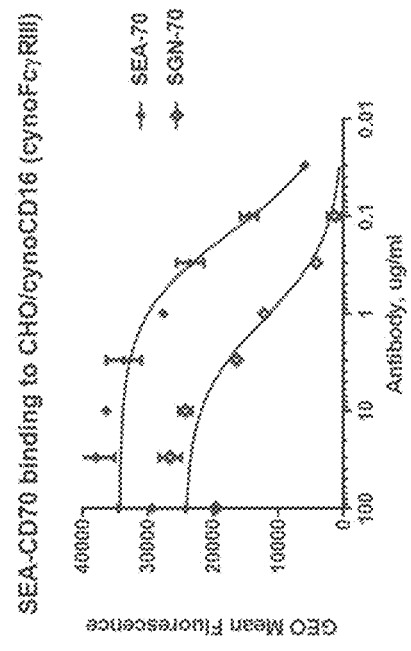
FIG. 2A-2B is a series of graphs assessing the binding of SGN-70 and SEA-CD70 (labeled as SEA-70 in FIG. 2A-2B) to the high affinity human FcγRIIIa receptor (158V) (FIG. 2A) or the cynomolgus FcγRIIIa receptor (FIG. 2B) using flow cytometry.

Unless defined otherwise, all technical and scientific terms used herein have the same meaning as commonly understood by one of ordinary skill in the art pertinent to the methods and compositions described. When trade names are used herein, applicants intend to independently include the trade name product formulation, the generic drug, and the active pharmaceutical ingredient(s) of the trade name product. As used herein, the following terms and phrases have the meanings ascribed to them unless specified otherwise.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "CD70 binding agent" and "anti-CD70 binding agent" as used herein means an anti-CD70 antibody, a derivative or a fragment of an anti-CD70 antibody, or other agent that binds to CD70 and comprises at least one CDR or variable region of a CD70 binding antibody, or a derivative thereof.

The term "specifically binds" means that the binding agent will react, in a highly selective manner, with its corresponding antigen and not with the multitude of other antigens (e.g., non-CD70 molecules).

As used herein, the term "functional" in the context of a CD70 binding agent indicates that the binding agent is capable of binding to CD70.

The terms "inhibit" or "inhibition of" as used herein means to reduce by a measurable amount, or to prevent entirely.

The term "deplete" in the context of the effect of a CD70-binding agent on CD70-expressing cells refers to a reduction in the number of or elimination of the CD70-expressing cells.

"Intact antibodies" and "intact immunoglobulins" are defined herein as heterotetrameric glycoproteins, typically of about 150,000 daltons, composed of two identical light (L) chain and two identical heavy (H) chains. Each light chain is covalently linked to a heavy chain by a disulfide bond to form a heterodimer. The heterotetramer is formed by covalent disulfide linkage between the two identical heavy chains of such heterodimers. Although the light and heavy chains are linked together by a disulfide bond, the number of disulfide linkages between the two heavy chains varies by immunoglobulin (Ig) isotype. Each heavy and light chain also has regularly spaced intrachain disulfide bridges. Each heavy chain has at the amino-terminus a variable domain ($V_H$), followed by three or four constant domains ($C_H1$, $C_H2$, $C_H3$, and/or $C_H4$), as well as a hinge (J) region between $C_H1$ and $C_H2$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (Chothia et al., 1985, J. Mol. Biol. 186: 651-663).

The term "hypervariable" refers to certain sequences within the variable domains that differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, M.D., whereas HVLs are structurally defined according to the three-dimensional structure of the variable domain, as described by Chothia and Lesk, 1987, J. Mol. Biol. 196:901-917. Where these two methods result in slightly different identifications of a CDR, the structural definition is preferred. As defined by Kabat (see Kabat et al., "Sequences of proteins of immunological interest, 5th ed., Pub. No. 91-3242, U.S. Dept. Health & Human Services, NIH, Bethesda, Md., 1991), CDR-L1 is positioned at about residues 24-34, CDR-L2, at about residues 50-56, and CDR-L3, at about residues and 89-97 in the light chain variable domain and at about 31-35 in CDR-H1, at about 50-65 in CDR-H2, and at about 95-102 in CDR-H3 in the heavy chain variable domain.

The three CDRs within each of the heavy and light chains are separated by framework regions (FRs), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains typically are not directly involved in antigen binding, but can contribute to antigen binding or mediate antibody effector function. Some FR residues can have a significant effect on antigen binding in at least three ways: by noncovalently binding directly to an epitope, by interacting with one or more CDR residues, and by affecting the interface between the heavy and light chains. The constant domains mediate various Ig effector functions, such as participation of the antibody in antibody dependent cellular cytotoxicity (ADCC), complement dependent cytotoxicity (CDC) and/or antibody dependent cellular phagocytosis (ADCP).

The light chains of vertebrate immunoglobulins are assigned to one of two clearly distinct classes, kappa (k) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., IgG1, IgG2, IgG3, IgG4, IgA, and IgA2. The heavy chain constant domains that correspond to the different classes of immunoglobulins are called α, δ, ε, γ, and μ, respectively. The subunit structures and three-dimensional configurations of the classes of native immunoglobulins are well known.

The terms "antibody", "anti-CD70 antibody", "humanized anti-CD70 antibody", and "variant humanized anti-CD70 antibody" are used herein in the broadest sense and specifically encompass full-length and native antibodies, monoclonal antibodies (including full-length monoclonal antibodies), polyclonal antibodies, multispecific antibodies (e.g., bispecific antibodies), and antibody or antigen-binding fragments thereof, such as variable domains and other portions of antibodies that exhibit a desired biological activity, e.g., CD70 binding.

The term "monoclonal antibody" (mAb) refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Köhler et al., 1975, *Nature* 256: 495, or recombinant DNA methods known in the art (see, e.g., U.S. Pat. No. 4,816,567). In another example, monoclonal antibodies can also be isolated from phage antibody libraries, using techniques described in Clackson et al., 1991, *Nature* 352: 624-628, and Marks et al., 1991, *J. Mol. Biol.* 222:581-597.

In contrast, the antibodies in a preparation of polyclonal antibodies are typically a heterogeneous population of immunoglobulin isotypes and/or classes and also exhibit a variety of epitope specificity.

The term "chimeric" antibody, as used herein, is a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence. Chimeric antibodies include fragments of such antibodies, provided that the antibody fragment exhibits the desired biological activity of its parent antibody, for example binding to the same epitope (see, e.g., U.S. Pat. No. 4,816, 567; and Morrison et al., 1984, *Proc. Natl. Acad Sci. USA* 81:6851-6855). Methods for producing chimeric antibodies are known in the art. (See, e.g., Morrison, 1985. *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

The terms "antibody fragment", "anti-CD70 antibody fragment", "humanized anti-CD70 antibody fragment", and "variant humanized anti-CD70 antibody fragment" refer to a portion of a full-length anti-CD70 antibody in which a variable region or a functional capability is retained, for example, specific CD70 epitope binding. Examples of antibody fragments include, but are not limited to, a Fab, Fab', F(ab')$_2$, Fd, Fv, scFv and scFv-Fc fragment, diabody, triabody, tetrabody, linear antibody, single-chain antibody, and other multispecific antibodies formed from antibody fragments. (See Holliger and Hudson, 2005, *Nat. Biotechnol.* 23:1126-1136.)

A "single-chain Fv" or "scFv" antibody fragment is a single chain Fv variant comprising the $V_H$ and $V_L$ domains of an antibody, in which the domains are present in a single polypeptide chain and which is capable of recognizing and binding antigen. The scFv polypeptide optionally contains a polypeptide linker positioned between the $V_H$ and $V_L$ domains that enables the scFv to form a desired three-dimensional structure for antigen binding (see, e.g., Pluckthun, 1994, In *The Pharmacology of Monoclonal Antibodies*, Vol. 113, Rosenburg and Moore eds., Springer-Verlag, New York, pp. 269-315).

The term "diabody" refers to small antibody fragment having two antigen-binding sites. Each fragment contains a heavy chain variable domain ($V_H$) concatenated to a light chain variable domain ($V_L$) to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 404 097; WO 93/11161; and Hollinger et al., 1993, *Proc. Natl. Acad. Sci. USA* 90:6444-6448.

The term "linear antibody" refers to antibodies that comprises a pair of tandem Fd segments ($V_H$-$C_H$1-$V_H$-$C_H$1) that form a pair of antigen binding regions. Linear antibodies can be bispecific or monospecific, as described in Zapata et al., 1995, *Protein Eng.* 8(10):1057-1062.

A "humanized antibody" refers to an immunoglobulin amino acid sequence variant or fragment thereof which is capable of binding to a predetermined antigen and which comprises a variable region polypeptide chain having framework regions having substantially the amino acid sequence of a human immunoglobulin and a CDR(s) having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and typically two, variable domains in which all or substantially all of the CDR regions correspond to those of a non-human immunoglobulin and all or substantially all of the framework regions are those of a human immunoglobulin sequence, such as from, for example, a consensus or germline sequence. The humanized antibody optionally also will comprise at least a portion of an immunoglobulin Fc domain, typically that of a human immunoglobulin. For example, the antibody may contain both the light chain as well as at least the variable domain of a heavy chain. The antibody also may include the $C_H1$, hinge (J), $C_H2$, $C_H3$, and/or $C_H4$ regions of the heavy chain, as appropriate.

The humanized antibody can be selected from any class of immunoglobulins, including IgM, IgG, IgD, IgA and IgE, and any isotype, including $IgG_1$, $IgG_2$, $IgG_3$ and $IgG_4$. The constant region or domain can include, for example, a complement fixing constant domain where it is desired that the humanized antibody exhibit cytotoxic activity (e.g., $IgG_1$). Where such cytotoxic activity is not desirable, the constant domain may be of another class (e.g., $IgG_2$). The humanized antibody may comprise sequences from more than one class or isotype, and selecting particular constant domains to optimize desired effector functions is within the ordinary skill in the art.

The FR and CDR regions of the humanized antibody need not correspond precisely to the parental sequences, e.g., the import CDR or the consensus FR may be altered by substitution, insertion or deletion of at least one residue so that the CDR or FR residue at that site does not correspond to either the consensus or the import antibody. Such mutations typically will not be extensive. Usually, at least 75% of the humanized antibody residues will correspond to those of the parental FR and CDR sequences, more often at least 90%, and most often greater than 95%.

The term "antibody effector function(s)" as used herein refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD70 targeted cell. Without intending to be bound by any particular theory, Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, 4$^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). Clq of the complement system binds to the Fc regions of antibodies when they are complexed with antigens. Binding of Clq to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N. Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

"Immune cell" as used herein refers to a cell of hematopoietic lineage involved in regulating an immune response. In typical embodiments, an immune cell is a T lymphocyte, a B lymphocyte, an NK cell, a monocyte/macrophage, or a dendritic cell.

"Effector cell" as used herein refers to a cell that expresses a surface receptor for the Fc domain of an immunoglobulin (FcR). For example, cells that express surface FcR for IgGs including FcγRIII (CD16), FcγRII (CD32) and FcγRIII (CD64) can act as effector cells. Such effector cells include monocytes, macrophages, natural killer (NK) cells, neutrophils and eosinophils.

A "therapeutic agent" is an agent that exerts a cytotoxic, cytostatic, and/or immunomodulatory effect on cancer cells, activated immune cells or other target cell population.

Examples of therapeutic agents include cytotoxic agents, chemotherapeutic agents, cytostatic agents, and immunomodulatory agents.

A "cytotoxic effect" refers to the depletion, elimination and/or the killing of a target cell. A "cytotoxic agent" refers to an agent that has a cytotoxic effect on a cell. The term is intended to include radioactive isotopes (such as $I^{131}$, $I^{125}$, $Y^{90}$ and $Re^{186}$), chemotherapeutic agents, and toxins such as enzymatically active toxins of bacterial, fungal, plant, or animal origin, and fragments thereof. Such cytotoxic agents can be coupled to an antibody, e.g., a humanized anti-CD70 antibody, and used, for example, to treat a patient indicated for therapy with the antibody. In one embodiment, "cytotoxic agent" includes monoclonal antibodies, e.g., antibodies used in combination with the humanized antibodies described herein.

A "chemotherapeutic agent" is a chemical compound useful in the treatment of cancer. Examples of chemotherapeutic agents include alkylating agents such a thiotepa and cyclosphosphamide (CYTOXAN™); alkyl sulfonates such as busulfan, improsulfan, and piposulfan; aziridines such as benzodopa, carboquone, meturedopa, and uredopa; ethylenimines and methylamelamines including altretamine, triethylenemelamine, triethylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues) and derivatives thereof; cryptophycines (particularly cryptophycin 1 and cryptophycin 8); dolastatin, auristatins (including analogues monomethyl-auristatin E and monomethyl-auristatin F (see, e.g., U.S. Published Application No. 2005-0238649, published Oct. 27, 2005, incorporated herein in its entirety); duocarmycin (including the synthetic analogues, KW-2189 and CBI-TMI); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calicheamicin gamma1I and calicheamicin phiI1, see for example, *Agnew, Chem. Intl. Ed. Engl.*, 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, 1986, "Prodrugs in Cancer Chemotherapy", In *Biochemical Society Transactions*, 14, pp. 375-382, 615th Meeting Belfast; and Stella et al., 1985, "Prodrugs: A Chemical Approach to Targeted Drug Delivery, In: "*Directed Drug Delivery*, Borchardt et al., (ed.), pp. 247-267, Humana Press. Useful prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

A "cytostatic effect" refers to the inhibition of cell proliferation. A "cytostatic agent" refers to an agent that has a cytostatic effect on a cell, thereby inhibiting the growth and/or expansion of a specific subset of cells.

The term "immunomodulatory effect" as used herein refers to a stimulation (immunostimulatory) or inhibition (immunosuppressive) of the development or maintenance of an immunologic response. Inhibition can be effected by, for example, by elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). An "immunomodulatory agent" refers to an agent that has an immunomodulatory effect on a cell. In some embodiments, an immunomodulatory agent has a cytotoxic or cytostatic effect on an immune cell that promotes an immune response.

The term "label" refers to a detectable compound or composition that is conjugated directly or indirectly to the antibody. The label may itself be detectable (e.g., radioisotope labels or fluorescent labels) or, in the case of an enzymatic label, may catalyze chemical alteration of a substrate compound or composition that is detectable. Labeled anti-CD70 antibody can be prepared and used in various applications including in vitro and in vivo diagnostics.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "control sequences" refers to polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-CD70 binding agent in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers canbe used to link the DNA sequences.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide typically having at least 20 contiguous or at least 50 contiguous amino acids of the polypeptide. A "derivative" is a polypeptide or fragment thereof having one or more non-conservative or conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof. "Antibody" includes the antibody in situ within recombinant cells since at least one component of the antibody's natural environment will not be present.

In certain embodiments, the antibody will be purified (1) to greater than 95% by weight of antibody as determined by the Lowry method, and in other aspects to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The term "heterologous," in the context of a polypeptide, means from a different source (e.g., a cell, tissue, organism, or species) as compared with another polypeptide, so that the two polypeptides are different. Typically, a heterologous polypeptide is from a different species.

In the context of immunoglobulin polypeptides or fragments thereof, "conservative substitution" means one or more amino acid substitutions that do not substantially reduce specific binding (e.g., as measured by the $K_D$) of the immunoglobulin polypeptide or fragment thereof to an antigen (i.e., substitutions that increase binding affinity, that do not significantly alter binding affinity, or that reduce binding affinity by no more than about 40%, typically no more than about 30%, more typically no more than about 20%, even more typically no more than about 10%, or most typically no more than about 5%, as determined by standard binding assays such as, e.g., ELISA).

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (e.g., as determined using one of the methods set forth infra).

The terms "similarity" or "percent similarity" in the context of two or more polypeptide sequences refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or 95% identical, or conservatively substituted, to the second amino acid sequence when compared to an equal number of amino acids as the number contained in the first sequence, or when compared to an alignment of polypeptides that has been aligned by, e.g., one of the methods set forth infra.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

In the context of anti-CD70 antibodies, or derivatives thereof, a protein that has one or more polypeptide regions substantially identical or substantially similar to one or more antigen-binding regions (e.g., a heavy or light chain variable region, or a heavy or light chain CDR) of an anti-CD70 antibody retains specific binding to an epitope of CD70 recognized by the anti-CD70 antibody, as determined using any of various standard immunoassays known in the art or as referred to herein.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers. It is also understood that all progeny may not be precisely identical in DNA content, due to deliberate or naturally occurring mutations. Mutant progeny that have the same function or biological activity as screened for in the originally transformed cell are included. Where distinct designations are intended, it will be clear from the context.

The term "subject" for purposes of treatment refers to any animal, particularly an animal classified as a mammal, including humans, domesticated and farm animals, and zoo, sports, or pet animals, such as dogs, horses, cats, cows, and the like. Preferably, the subject is human.

A "disorder", as used herein, and the terms "CD70-associated disorder" and "CD70-associated disease" refer to any condition that would benefit from treatment with an anti-CD70 binding agent, as described herein. A "CD70-associated disorder" and "CD70-associated disease" typically express CD70, or a fragment thereof, on the cell surface. This includes chronic and acute disorders or diseases including those pathological conditions that predispose the mammal to the disorder in question. Non-limiting examples or disorders to be treated herein include cancer, myeloid malignancies, hematological malignancies, benign and malignant tumors, leukemias and lymphoid malignancies, carcinomas, and inflammatory, angiogenic and immunologic disorders. Specific examples of disorders are disclosed infra.

The terms "treatment" and "therapy", and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder, thereby preventing or removing all signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein.

As used herein, the terms "prevention" or "prevent" refer to administration of an anti-CD70 binding agent to a subject before the onset of a clinical or diagnostic symptom of a CD70-expressing cancer or immunological disorder (e.g., administration to an individual with a predisposition or at a high risk of acquiring the CD70-expressing cancer or immunological disorder) to (a) block the occurrence or onset of the CD70-expressing cancer or immunological disorder, or one or more of clinical or diagnostic symptoms thereof, (b) inhibit the severity of onset of the CD70-expressing cancer or immunological disorder, or (c) to lessen the likelihood of the onset of the CD70-expressing cancer or immunological disorder.

The term "intravenous infusion" refers to introduction of an agent, e.g., a therapeutic agent, into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent, e.g., a therapeutic agent, under the skin of an animal or human patient, typically within a pocket between the skin and underlying tissue, by relatively slow, sustained delivery from a drug receptacle. Pinching or drawing the skin up and away from underlying tissue may create the pocket.

The term "package insert" is used to refer to instructions customarily included in commercial packages of therapeutic products, that contain information about the indications, usage, administration, contraindications and/or warnings concerning the use of such therapeutic products.

A "liposome" is a small vesicle composed of various types of lipids, phospholipids and/or surfactant which is useful for delivery of a drug (such as an antibody) to a mammal. The components of the liposome are commonly arranged in a bilayer formation, similar to the lipid arrangement of biological membranes.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "effective amount" refers to the amount of an anti-CD70 binding agent (e.g., an antibody or derivative or other binding agent) that is sufficient to inhibit the occurrence or ameliorate one or more clinical or diagnostic symptoms of a CD70-expressing cancer or immunological disorder in a subject. An effective amount of an agent is administered according to the methods described herein in an "effective regimen." The term "effective regimen" refers to a combination of amount of the agent and dosage frequency adequate to accomplish treatment or prevention of a CD70-expressing cancer or immunological disorder.

The term "therapeutically effective amount" is used to refer to an amount of a therapeutic agent having beneficial patient outcome, for example, a growth arrest effect or deletion of the cell. In one aspect, the therapeutically effective amount has apoptotic activity, or is capable of inducing cell death. In another aspect, the therapeutically effective amount refers to a target serum concentration that has been shown to be effective in, for example, slowing disease progression. Efficacy can be measured in conventional ways, depending on the condition to be treated. For example, in neoplastic diseases or disorders characterized by cells expressing CD70, efficacy can be measured by assessing the time to disease progression (TTP), or determining the response rates (RR).

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PES" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of corn ete response (CR) rate and partial response (PR) rate.

As used herein, "overall survival" or "OS" refers to the percentage of individuals in a group who are likely to be alive after a particular duration of time.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:

Is fatal or life-threatening (as used in the definition of a serious adverse event, "life-threatening" refers to an event in which the patient was at risk of death at the time of the event; it does not refer to an event which hypothetically might have caused death if it was more severe.

Results in persistent or significant disability/incapacity

Constitutes a congenital anomaly/birth defect

Is medically significant, i.e., defined as an event that jeopardizes the patient or may require medical or surgical intervention to prevent one of the outcomes listed above. Medical and scientific judgment must be exercised in deciding whether an AE is "medically significant"

Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD70-binding agent is administered.

The phrase "pharmaceutically acceptable salt," as used herein, refers to pharmaceutically acceptable organic or inorganic salts of an anti-CD70 binding agent or therapeutic agent. The anti-CD70 binding agent or therapeutic agent contains at least one amino group, and accordingly acid addition salts can be formed with this amino group or other suitable groups. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and an anti-CD70 binding agent and/or therapeutic agent. Examples of solvents that form pharmaceutically acceptable solvates include, but are not limited to, water, isopropanol, ethanol, methanol, DMSO, ethyl acetate, acetic acid, and ethanolamine.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleunine-dolaproine-phenylalanine.

The abbreviations "fk" and "phe-lys" refer to the linker phenylalanine-lysine.

The terms "Treg" or "regulatory T cell" refer to $CD4^+$ T cells that suppresses CD4+CD25+ and CD8+ T cell proliferation and/or effector function, or that otherwise downmodulate an immune response. Notably, Treg may downregulate immune responses mediated by Natural Killer cells, Natural Killer T cells as well as other immune cells.

The terms "regulatory T cell function" or "a function of Treg" are used interchangeably to refer to any biological function of a Treg that results in a reduction in $CD4+CD25^+$ or $CD8^+$ T cell proliferation or a reduction in an effector T cell-mediated immune response. Treg function can be measured via techniques established in the art. Non-limiting examples of useful in vitro assays for measuring Treg function include Transwell suppression assays as well as in vitro assays in which the target conventional T cells (Tconv) and Tregs purified from human peripheral blood or umbilical cord blood (or murine spleens or lymph nodes) are optionally activated by anti-$CD3^+$ anti-CD28 coated beads (or antigen-presenting cells (APCs) such as, e.g., irradiated splenocytes or purified dendritic cells (DCs) or irradiated PBMCs) followed by in vitro detection of conventional T cell proliferation by measuring incorporation of radioactive nucleotides (such as, e.g., [H]-thymidine) or fluorescent nucleotides, or by Cayman Chemical MTT Cell Proliferation Assay Kit, or by monitoring the dilution of a green fluorochrome ester CFSE or Seminaphtharhodafluor (SNARE-1) dye by flow cytometry). Other common assays measure T cell cytokine responses. Useful in vivo assays of Treg function include assays in animal models of diseases in which Tregs play an important role, including, e.g., (1) homeostasis model (using na'ive homeostatically expanding CD4$^+$ T cells as target cells that are primarily suppressed by Tregs), (2) inflammatory bowel disease (IBD) recovery model (using Th1 T cells (Th17) as target cells that are primarily suppressed by Tregs), (3) experimental autoimmune encephalomyelitis (EAE) model (using Th1 7 and Th1 T cells as target cells that are primarily suppressed by Tregs), (4) B16 melanoma model (suppression of antitumor immunity) (using CD8$^+$ T cells as target cells that are primarily suppressed by Tregs), (5) suppression of colon inflammation in adoptive transfer colitis where na'ive CD4$^+$CD45RB$^M$ Tconv cells are transferred into RagV mice, and (6) Foxp3 rescue model (using lymphocytes as target cells that are primarily suppressed by Tregs). According to one protocol, all of the models require mice for donor T cell populations as well as Rag1$^{-/-}$ or Foxp3 mice for recipients. For more details on various useful assays see, e.g., Collison and Vignali, In Vitro Treg Suppression Assays, Chapter 2 in Regulatory T Cells: Methods and Protocols, Methods in Molecular Biology, Kassiotis and Liston eds., Springer, 2011, 707:21-37; Workman et al, In Vivo Treg Suppression Assays, Chapter 9 in Regulatory T Cells: Methods and Protocols, Methods in Molecular Biology, Kassiotis and Liston eds., Springer, 2011, 119-156; Takahashi et al, Mt. Immunol, 1998, 10: 1969-1980; Thornton et al, J. Exp. Med., 1998, 188:287-296; Collison et al, J. Immunol, 2009, 182:6121-6128; Thornton and Shevach, J. Exp. Med., 1998, 188:287-296; Asseman et al, J. Exp. Med., 1999, 190:995-1004; Dieckmann et al, J. Exp. Med., 2001, 193: 1303-1310; Belkaid, Nature Reviews, 2007, 7:875-888; Tang and Bluestone, Nature Immunology, 2008, 9:239-244; Bettini and Vignali, Curr. Opin. Inuttunol, 2009, 21:612-618; Dannull et al, J Clin Invest, 2005, 115(12):3623-33; Tsaknaridis, et al, J Neurosci Res., 2003, 74:296-308.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Anti-CD70 Antibodies

The invention provides anti-CD70 antibodies, such as humanized antibodies derived from the mouse antibody 1F6. 1F6 is a murine immunoglobulin G1 (IgG1) monoclonal antibody against CD70. 1F6 and humanized 1F6 variants are described in U.S. Pat. No. 8,067,546 and International Patent Publication WO 2006/113909. In some embodiments, the anti-CD70 antibody is nonfucosylated.

The binding affinity of humanized forms of the mouse 1F6 antibody (i.e., dissociation constant, K$_D$) is preferably within a factor of five or a factor of two of that of the mouse antibody 1F6 for human CD70. Humanized 1F6 antibodies specifically bind to human CD70 in native form and/or recombinantly expressed from Chinese hamster ovary (CHO) cells as does the mouse antibody from which they were derived. Preferred humanized 1F6 antibodies have an affinity the same as or greater than (i.e., greater than beyond margin of error in measurement) that of 1F6 for human CD70 (e.g., 1.1-5 fold, 1.1 to 3 fold, 1.5 to 3-fold, 1.7 to 2.3-fold or 1.7-2.1-fold the affinity or about twice the affinity of 1F6). Preferred humanized 1F6 antibodies bind to the same epitope and/or compete with 1F6 for binding to human CD70.

In some embodiments, antibodies of the invention inhibit cancer (e.g., growth of cells, metastasis and/or lethality to the organisms) as shown on cancerous cells propagating in culture, in an animal model or clinical trial. Animal models can be formed by implanting CD70-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections.

Once established within a host, these tumor models can be applied to evaluate the therapeutic efficacies of the anti-CD70 antibodies, or conjugated forms thereof, as described in the Examples.

Generally, anti-CD70 antibodies of the disclosure bind CD70, e.g., human CD70, and exert cytostatic and cytotoxic effects on malignant cells, such as cancer cells. Anti-CD70 antibodies of the disclosure are preferably monoclonal, and may be multispecific, human, humanized or chimeric antibodies, single chain antibodies, Fab fragments, F(ab') fragments, fragments produced by a Fab expression library, and CD70 binding fragments of any of the above. In some embodiments, the anti-CD70 antibodies of the disclosure specifically bind CD70. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the anti-CD70 antibodies are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a V$_L$ or V$_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-CD70 antibodies or antigen-binding fragments thereof are human, murine (e.g., mouse and rat), donkey, sheep, rabbit, goat, guinea pig, camelid, horse, or chicken.

The anti-CD70 antibodies of the present disclosure may be monospecific, bispecific, trispecific or of greater multi specificity. Multispecific antibodies may be specific for different epitopes of CD70 or may be specific for both CD70 as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

The anti-CD70 antibodies of the present disclosure may be humanized antibodies. In some embodiments, the anti-CD70 antibodies of the present disclosure are humanized antibodies of the mouse antibody 1F6. Humanized versions of 1F6 are described in U.S. Pat. No. 8,067,546. A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon $V_H$1-2 (also referred to in the literature as HV1-2) (Shin et al, 1991, EMBO J. 10:3641-3645) and for the hinge region ($J_H$), exon $J_H$-6 (Mattila et al, 1995, Eur. J. Immunol. 25:2578-2582). For the light chain, a preferred acceptor sequence is exon VK2-30 (also referred to in the literature as KV2-30) and for the hinge region exon JK-4 (Hieter et al, 1982, J. Biol. Chem. 257:1516-1522). Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:
   (1) noncovalently binds antigen directly,
   (2) is adjacent to a CDR region,
   (3) otherwise interacts with a CDR region (e.g. is within about 6 A of a CDR region); or
   (4) mediates interaction between the heavy and light chains.

Anti-CD70 antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementarity determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

CDR sequences of the anti-CD70 antibodies and of the anti-CD70 antibody-drug conjugates described herein are according to the Kabat numbering scheme as described in Kabat et al. (1991), "Sequences of Proteins of Immunological Interest," 5th Ed. Public Health Service, National Institutes of Health, Bethesda, Md., unless specified otherwise.

In one aspect, provided herein is an anti-CD70 antibody comprising a heavy chain variable region comprising the three CDRs of SEQ ID NO:1 and a light chain variable region comprising the three CDRs of SEQ ID NO:2, wherein the CDRs of the anti-CD70 antibody are defined by the Kabat numbering scheme. In some embodiments, the anti-CD70 antibody further comprises an Fc domain. In some embodiments, the anti-CD70 antibody is nonfucosylated.

An anti-CD70 antibody described herein may comprise any suitable framework variable domain sequence, provided that the antibody retains the ability to bind CD70 (e.g., human CD70). As used herein, heavy chain framework regions are designated "HC-FR1-FR4," and light chain framework regions are designated "LC-FR1-FR4."

In some embodiments of the anti-CD70 antibodies described herein, the heavy chain variable domain comprises the amino acid sequence of (SEQ ID NO: 1)
QVQLVQSGAEVKKPGASVKVSCKASGYTFTNYGMNWVRQAPGQGLKWMG

WINTYTGEPTYADAFKGRVTMTRDTSISTAYMELSRLRSDDTAVYYCAR

DYGDYGMDYWGQGTTVTVSS and the light chain variable domain comprises the amino acid sequence of

```
                                                 (SEQ ID NO: 2)
DIVMTQSPDSLAVSLGERATINCRASKSVSTSGYSFMHWYQQKPGQPPK

LLIYLASNLESGVPDRFSGSG SGTDFTLTISSLQAEDVAVYYCQHSRE

VPWTFGQGTKVEIK.
```

In some embodiments of the anti-CD70 antibodies described herein, the heavy chain variable domain comprises the amino acid sequence of

```
                                                 (SEQ ID NO: 1)
QVQLVQSGAEVKKPGASVKVSCKASGYTFTNYGMNWVRQAPGQGLKWMG

WINTYTGEPTYADAFKGRVTMTRDTSISTAYMELSRLRSDDTAVYYCAR

DYGDYGMDYWGQGTTVTVSS
``` and the light chain variable domain comprises the amino acid sequence of

```
                                                 (SEQ ID NO: 7)
DIVMTQSPDSLAVSLGERATINCRASKSVSTSGYSFMHWYQQKPGQPPK

LLIYLASNLESGVPDRFSGSG SGTDFTLTISSLQAEDVAVYYCQHSRE

VPWTFGQGTKVEIKR.
```

In one aspect, provided herein is an anti-CD70 antibody comprising a heavy chain variable domain comprising the amino acid sequence of SEQ ID NO:1 or comprising a light chain variable domain comprising the amino acid sequence of SEQ ID NO:2. In some embodiments, the N-terminal glutamine of the heavy chain variable domain is cyclized to form pyroglutamic acid. In one aspect, provided herein is an anti-CD70 antibody comprising a heavy chain variable domain comprising the amino acid sequence of SEQ ID NO:1 and comprising a light chain variable domain comprising the amino acid sequence of SEQ ID NO:2. In some embodiments, the N-terminal glutamine of the heavy chain variable domain is cyclized to form pyroglutamic acid.

In one aspect, provided herein is an anti-CD70 antibody comprising a heavy chain variable domain comprising the amino acid sequence of SEQ ID NO:1 or comprising a light chain variable domain comprising the amino acid sequence of SEQ ID NO:7. In some embodiments, the N-terminal glutamine of the heavy chain variable domain is cyclized to form pyroglutamic acid. In one aspect, provided herein is an anti-CD70 antibody comprising a heavy chain variable domain comprising the amino acid sequence of SEQ ID NO:1 and comprising a light chain variable domain comprising the amino acid sequence of SEQ ID NO:7. In some embodiments, the N-terminal glutamine of the heavy chain variable domain is cyclized to form pyroglutamic acid.

In some embodiments, provided herein is an anti-CD70 antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:1. In some embodiments, the N-terminal glutamine of the heavy chain variable domain is cyclized to form pyroglutamic acid. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:1 contains substitutions (e.g., conservative substitutions), insertions, or deletions relative to the reference sequence and retains the ability to bind to a CD70 (e.g., human CD70). In certain embodiments, a total of 1 to 10 amino acids have been substituted, inserted and/or deleted in SEQ ID NO:1. In certain embodiments, substitutions, insertions, or deletions (e.g., 1, 2, 3, 4, or 5 amino acids) occur in regions outside the CDRs (i.e., in the FRs). In some embodiments, the anti-CD70 antibody comprises a heavy chain variable domain sequence of SEQ ID NO:1 including post-translational modifications of that sequence. In some embodiments, the N-terminal glutamine of the heavy chain variable domain is cyclized to form pyroglutamic acid.

In some embodiments, provided herein is an anti-CD70 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:2. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:2 contains substitutions (e.g., conservative substitutions), insertions, or deletions relative to the reference sequence and retains the ability to bind to a CD70 (e.g., human CD70). In certain embodiments, a total of 1 to 10 amino acids have been substituted, inserted and/or deleted in SEQ ID NO:2. In certain embodiments, substitutions, insertions, or deletions (e.g., 1, 2, 3, 4, or 5 amino acids) occur in regions outside the CDRs (i.e., in the FRs). In some embodiments, the anti-CD70 antibody comprises a light chain variable domain sequence of SEQ ID NO:2 including post-translational modifications of that sequence.

In some embodiments, provided herein is an anti-CD70 antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:5 contains substitutions (e.g., conservative substitutions), insertions, or deletions relative to the reference sequence and retains the ability to bind to a CD70 (e.g., human CD70). In certain embodiments, a total of 1 to 10 amino acids have been substituted, inserted and/or deleted in SEQ ID NO:7. In certain embodiments, substitutions, insertions, or deletions (e.g., 1, 2, 3, 4, or 5 amino acids) occur in regions outside the CDRs (i.e., in the FRs). In some embodiments, the anti-CD70 antibody comprises a light chain variable domain sequence of SEQ ID NO:7 including post-translational modifications of that sequence.

In some embodiments, provided herein is an anti-CD70 antibody comprising a heavy chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence

```
                                             (SEQ ID NO: 3)
QVQLVQSGAE VKKPGASVKV SCKASGYTFT NYGMNWVRQA

PGQGLKWMGW INTYTGEPTY ADAFKGRVTM TRDTSISTAY

MELSRLRSDD TAVYYCARDY GDYGMDYWGQ GTTVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKKVEPKS CDKTHTCPPC PAPELLGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSRDELT

KNQVSLTCLV KGFYPSDIAV EWESNGQPEN NYKTTPPVLD

SDGSFFLYSK LTVDKSRWQQ GNVFSCSVMH EALHNHYTQK

SLSLSPGK.
```

In certain embodiments, a heavy chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:3 contains substitutions (e.g., conservative substitutions), insertions, or deletions relative to the reference sequence and retains the ability to bind to a CD70 (e.g., human CD70). In certain embodiments, a total of 1 to 10 amino acids have been substituted, inserted and/or deleted in SEQ ID NO:3. In certain embodiments, substitutions, insertions, or deletions (e.g., 1, 2, 3, 4, or 5 amino acids) occur in regions outside the CDRs (i.e., in the FRs). In some embodiments, the anti-CD70 antibody comprises a heavy chain sequence of SEQ ID NO:3 including post-translational modifications of that sequence.

In some embodiments, provided herein is an anti-CD70 antibody comprising a light chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of

```
                                             (SEQ ID NO: 4)
DIVMTQSPDS LAVSLGERAT INCRASKSVS TSGYSFMHWY

QQKPGQPPKL LIYLASNLES GVPDRFSGSG SGTDFTLTIS

SLQAEDVAVY YCQHSREVPW TFGQGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC.
```

In certain embodiments, a light chain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:4 contains substitutions (e.g., conservative substitutions), insertions, or deletions relative to the reference sequence and retains the ability to bind to a CD70 (e.g., human CD70). In certain embodiments, a total of 1 to 10 amino acids have been substituted, inserted and/or deleted in SEQ ID NO:4. In certain embodiments, substitutions, insertions, or deletions (e.g., 1, 2, 3, 4, or 5 amino acids) occur in regions outside the CDRs (i.e., in the FRs). In some embodiments, the anti-CD70 antibody comprises a light chain sequence of SEQ ID NO:4 including post-translational modifications of that sequence.

In some embodiments, the anti-CD70 antibody comprises a heavy chain variable domain as in any of the embodiments provided above, and a light chain variable domain as in any of the embodiments provided above. In one embodiment, the antibody comprises the heavy chain variable domain sequence of SEQ ID NO:1 and the light chain variable domain sequence of SEQ ID NO:2, including post-translational modifications of those sequences. In some embodiments, the N-terminal glutamine of the heavy chain variable domain is cyclized to form pyroglutamic acid.

In some embodiments, the anti-CD70 antibody comprises: i) an amino acid sequence having at least 85% sequence identity to a heavy chain variable region comprising the amino acid sequence of SEQ ID NO:1, and ii) an amino acid sequence having at least 85% sequence identity to a light chain variable region comprising the amino acid sequence of SEQ ID NO:2. In some embodiments, the N-terminal glutamine of the heavy chain variable domain is cyclized to form pyroglutamic acid.

In some embodiments, the anti-CD70 antibody is a monoclonal antibody.

In some embodiments, the anti-CD70 antibody comprises a heavy chain variable region comprising the three CDRs or a light chain variable region comprising the three CDRs of an anti-CD70 antibody described in U.S. Pat. Nos. 8,067,546, 8,562,987, 9,428,585, 9,701,752, US 2009/0148942, US 2012/0045436, US 2014/0178936, US 2017/0022282 or International Patent Publication WO 2006/113909. In some embodiments, the anti-CD70 antibody comprises a heavy chain variable region comprising the three CDRs and a light chain variable region comprising the three CDRs of an anti-CD70 antibody described in U.S. Pat. Nos. 8,067,546, 8,562,987, 9,428,585, 9,701,752, US 2009/0148942, US 2012/0045436, US 2014/0178936, US 2017/0022282 or International Patent Publication WO 2006/113909. In some embodiments, the CDRs are defined by the Kabat numbering scheme.

In some embodiments, the anti-CD70 antibody comprises a heavy chain variable region or a light chain variable region of an anti-CD70 antibody described in U.S. Pat. Nos. 8,067,546, 8,562,987, 9,428,585, 9,701,752, US 2009/0148942, US 2012/0045436, US 2014/0178936, US 2017/0022282 or International Patent Publication WO 2006/113909. In some embodiments, the anti-CD70 antibody comprises a heavy chain variable region and a light chain variable region of an anti-CD70 antibody described in U.S. Pat. Nos. 8,067,546, 8,562,987, 9,428,585, 9,701,752, US 2009/0148942, US 2012/0045436, US 2014/0178936, US 2017/0022282 or International Patent Publication WO 2006/113909.

In some embodiments, the anti-CD70 antibody is an anti-CD70 antibody, such as a humanized 1F6 variant, as described in U.S. Pat. Nos. 8,067,546, 8,562,987, 9,428,585, 9,701,752, US 2009/0148942, US 2012/0045436, US 2014/0178936, US 2017/0022282 or International Patent Publication WO 2006/113909.

In some embodiments, the anti-CD70 antibody comprises a heavy chain variable region comprising the three CDRs or a light chain variable region comprising the three CDRs of the anti-CD70 antibody vorsetuzumab. In some embodiments, the anti-CD70 antibody comprises a heavy chain variable region comprising the three CDRs and a light chain variable region comprising the three CDRs of the anti-CD70 antibody vorsetuzumab. In some embodiments, the CDRs are defined by the Kabat numbering scheme.

In some embodiments, the anti-CD70 antibody comprises a heavy chain variable region or a light chain variable region of the anti-CD70 antibody vorsetuzumab. In some embodiments, the anti-CD70 antibody comprises a heavy chain variable region and a light chain variable region of the anti-CD70 antibody vorsetuzumab.

In some embodiments, the anti-CD70 antibody is vorsetuzumab.

Anti-CD70 antibodies of the present invention may also be described or specified in terms of their binding affinity to CD70 (e.g., human CD70). Preferred binding affinities include those with a dissociation constant or $K_D$ less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

In some embodiments, the anti-CD70 antibody comprises a heavy chain variable domain as in any of the embodiments provided above, and a light chain variable domain as in any of the embodiments provided above. In one embodiment, the antibody comprises a heavy chain constant region comprising the amino acid sequence of

```
                                         (SEQ ID NO: 5)
AS TKGPSVFPLA PSSKSTSGGT

AALGCLVKDY FPEPVTVSWN SGALTSGVHT FPAVLQSSGL

YSLSSVVTVP SSSLGTQTYI CNVNHKPSNT KVDKKVEPKS

CDKTHTCPPC PAPELLGGPS VFLFPPKPKD TLMISRTPEV

TCVVVDVSHE DPEVKFNWYV DGVEVHNAKT KPREEQYNST

YRVVSVLTVL HQDWLNGKEY KCKVSNKALP APIEKTISKA

KGQPREPQVY TLPPSRDELT KNQVSLTCLV KGFYPSDIAV

EWESNGQPEN NYKTTPPVLD SDGSFFLYSK LTVDKSRWQQ

GNVFSCSVMH EALHNHYTQK SLSLSPGK
``` and a light chain constant region comprising the amino acid sequence of

```
                                         (SEQ ID NO: 6)
TVAAPSVF IFPPSDEQLK SGTASVVCLL NNFYPREAKV

QWKVDNALQS GNSQESVTEQ DSKDSTYSLS STLTLSKADY

EKHKVYACEV THQGLSSPVT KSFNRGEC,
``` including post-translational modifications of those sequences.

The antibodies also include derivatives that are modified, i.e., by the covalent attachment of any type of molecule to the antibody such that covalent attachment does not prevent the antibody from binding to CD70 or from exerting a cytostatic or cytotoxic effect on cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The CD70-binding agent can optionally include an antibody effector domain that mediates or stimulates an ADCC, ADCP and/or CDC response against a CD70-expressing target cell. The effector domain(s) can be, for example, an Fc domain or domains of an Ig molecule. Such a CD70-binding agent can exert a cytotoxic or cytostatic effect on CD70-expressing cancer cells, or exert a cytotoxic, cytostatic, or immunomodulatory effect on activated lymphocytes or dendritic cells, for example, in the treatment of a CD70-expressing cancer or an immunological disorder, respectively. Typically, the CD70-binding agent recruits and/or activates cytotoxic white blood cells (e.g., natural killer (NK) cells, phagocytic cells (e.g., macrophages), and/or serum complement components).

The anti-CD70 antibody can be a humanized antibody, a single chain antibody, an scFv, a diabody, an Fab, a minibody, an scFv-Fc, an Fv, or the like. In some embodiments, a CD70 antigen-binding region can be joined to an effector domain or domains such as, for example, the hinge-$C_H2$-$C_H3$ domains of an immunoglobulin, or a portion or fragment of an effector domain(s) having effector function. Antigen-binding antibody fragments, including single-chain antibodies, can comprise, for example, the variable region(s) in combination with the entirety or a portion of an effector domain (e.g., a $C_H2$ and/or $C_H3$ domain alone or in combination with a $C_H1$, hinge and/or $C_L$ domain). Also, antigen-binding fragments can comprise any combination of effector domains. In some embodiments, the anti-CD70 antibody can be a single chain antibody comprising a CD70-binding variable region joined to hinge-$C_H2$-$C_H3$ domains.

The effector domains of the anti-CD70 antibody can be from any suitable human immunoglobulin isotype. For example, the ability of human immunoglobulin to mediate CDC and ADCC/ADCP is generally in the order of IgM≈IgG1≈IgG3>IgG2>IgG4 and IgG1≈4G3>IgG2/IgM/IgG4, respectively. A CD70-binding polypeptide can be expressed as a recombinant fusion protein comprising of the appropriate constant domains to yield the desired effector function(s). Upon binding to target cells, the anti-CD70 antibodies or derivatives can trigger in vitro and in vivo target cell destruction through an antibody effector function, such as ADCC, CDC, and ADCP.

The CD70-binding agent optionally can be conjugated to a therapeutic agent, such as a cytotoxic, cytostatic or immunomodulatory agent. Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like. In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netrop sin, epothilone A and B, estramustine, cryptophysins, cemadotin, maytansinoids, discodermolide, eleutherobin, and mitoxantrone. In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. Patent Application Publication Nos. 20030083263 and 20050009751), International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414. In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin). Examples of anti-tubulin agents include, but are not limited to, taxanes (e.g., Taxol® (paclitaxel), Taxotere® (docetaxel), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131).

In some embodiments, an anti-CD70 antibody can be chimeric, comprising a human or non-human Fc region or portion thereof. For example, the antibody can include an Fc domain or portion of non-human origin, e.g., rodent (e.g., mouse or rat), donkey, sheep, rabbit, goat, guinea pig, camelid, horse, chicken or monkey (e.g., macaque, rhesus or the like).

An anti-CD70 binding agent, such as an antibody, can be monospecific, bispecific, trispecific, or of greater multispecificity. Multispecific antibodies may be specific for different epitopes of CD70 and/or may be specific for both CD70 as well as for a heterologous protein. (See, e.g., PCT Publications WO 93/17715, WO 92/08802, WO 91/00360, and WO 92/05793; Tutt et al., 1991, J. Immunol. 147:60-69; U.S. Pat. Nos. 4,474,893; 4,714,681; 4,925,648; 5,573,920; and U.S. Pat. No. 5,601,819; Kostelny et al., 1992, J. Immunol. 148:1547-1553.) Multispecific antibodies, including bispecific and trispecific antibodies, useful for practicing the methods described herein are antibodies that immunospecifically bind to both CD70 (including but not limited to antibodies that have the CDRs of the monoclonal antibody 1F6) and a second cell surface receptor or receptor complex that mediates ADCC, ADCP, and/or CDC, such as CD16/FcγRIII, CD64/FcγRI, killer inhibitory or activating receptors, or the complement control protein CD59. In some embodiments, the binding of the portion of the multispecific antibody to the second cell surface molecule or receptor complex may enhance the effector functions of the anti-CD70 antibody or other CD70 binding agent.

The antibodies can be generated by methods known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988); and Hammerling et al., In *Monoclonal Antibodies and T-Cell Hybridomas*, pp. 563-681 (Elsevier, N.Y., 1981). Examples of phage display methods that can be used to make the anti-CD70 antibodies include, e.g., those disclosed in Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Jardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01134; PCT Publications WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which some have the correct bispecific structure. Similar procedures are disclosed in International Publication No. WO 93/08829, and in Traunecker et al., 1991, EMBO J. 10:3655-59.

According to a different approach, antibody variable domains with the desired binding specificities (antibody-antigen combining sites) are fused to immunoglobulin constant domain sequences. The fusion typically is with an immunoglobulin heavy chain constant domain, comprising at least part of the hinge, $C_H2$, and $C_H3$ regions. In some embodiments, the fusion includes a first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (see, e.g., International Publication No. WO 94/04690, which is incorporated herein by reference in its entirety).

For further discussion of bispecific antibodies see, for example, Suresh et al., 1986, *Methods in Enzymology* 121: 210; Rodrigues et al., 1993, *J. Immunology* 151:6954-61; Carter et al., 1992, *Bio/Technology* 10:163-67; Carter et al., 1995, *J. Hematotherapy* 4:463-70; Merchant et al., 1998, *Nature Biotechnology* 16:677-81. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example in International Publication WO 83/03679 and European Patent Publication No. EPA 0 217 577, both of which are incorporated herein by reference.

In some embodiments, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; Riechmann et al., 1988, *Nature* 332: 323.) Antibodies can be humanized using a variety of techniques known in the art including, for example, CDR-grafting (see, e.g., EP 0 239 400; PCT Publication WO 91/09967; U.S. Pat. Nos. 5,225,539; 5,530,101; and 5,585, 089), veneering or resurfacing (see, e.g., EP 0 592 106; EP 0 519 596; Padlan, 1991, *Molecular Immunology* 28(4/5): 489-498; Studnicka et al., 1994, *Protein Engineering* 7(6): 805-814; Roguska et al., 1994, *Proc. Natl. Acad. Sci. USA* 91:969-973), and chain shuffling (see, e.g., U.S. Pat. No. 5,565,332) (all of these references are incorporated by reference herein).

Humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 0 012 023; Berter et al., 1988, *Science* 240:1041-43; Liu et al., 1987, *Proc. Natl. Acad. Sci. USA* 84:3439-43; Liu et al., 1987, *J. Immunol.* 139:3521-26; Sun et al., 1987, *Proc. Natl. Acad. Sci. USA* 84:214-18; Nishimura et al., 1987, *Cancer. Res.* 47:999-1005; Wood et al., 1985, *Nature* 314:446-449; Shaw et al., 1988, *J. Natl. Cancer Inst.* 80:1553-59; Morrison, 1985, *Science* 229: 1202-07; Oi et al., 1986, *BioTechniques* 4:214; U.S. Pat. No. 5,225,539; Jones et al., 1986, *Nature* 321:552-25; Verhoeyan et al., 1988, *Science* 239:1534; and Beidler et al., 1988, *J. Immunol.* 141:4053-60; each of which is incorporated herein by reference in its entirety.

As set forth supra, a CD70 binding agent can be a derivative of an anti-CD70 antibody. Generally, an anti-CD70 antibody derivative comprises an anti-CD70 antibody (including e.g., an antigen-binding fragment or conservatively substituted polypeptides) and at least one polypeptide region or other moiety heterologous to the anti-CD70 antibody. For example, an anti-CD70 antibody can be modified, e.g., by the covalent attachment of any type of molecule. Typical modifications include, e.g., glycosylation, acetylation, pegylation, phosphorylation, amidation, derivatization by known protecting/blocking groups, proteolytic cleavage, linkage to a cellular ligand (e.g., an albumin-binding molecule) or other protein, and the like. Any of numerous chemical modifications may be carried out by known techniques, including, but not limited to specific chemical cleavage, acetylation, formylation, metabolic synthesis of tunicamycin, etc.

In some embodiments, the covalent attachment does not interfere with effector function, e.g., prevent the antibody derivative from specifically binding to CD70 via the antigen-binding region or region derived therefrom, or the effector domains(s) from specifically binding Fc receptor.

In some embodiments, the antibody derivative is a multimer, such as, for example, a dimer, comprising one or more monomers, where each monomer includes (i) an antigen-binding region of an anti-CD70 antibody, or a polypeptide region derived therefrom (such as, e.g., by conservative substitution of one or more amino acids), and (ii) a multimerizing (e.g., dimerizing) polypeptide region, such that the antibody derivative forms multimers (e.g., homodimers) that specifically bind to CD70. In typical embodiments, an antigen-binding region of an anti-CD70 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunological disorders or CD70-expressing cancers, the derivative is subjected to conditions that allow formation of a homodimer or heterodimer. A heterodimer, as used herein, may comprise identical dimerization domains but different CD70 antigen-binding regions, identical CD70 antigen-binding regions but different dimerization domains, or different CD70 antigen-binding regions and dimerization domains.

Typical dimerization domains are those that originate from transcription factors. In one embodiment, the dimerization domain is that of a basic region leucine zipper ("bZIP") (see Vinson et al., 1989, *Science* 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See, e.g., Landschultz et al., 1988, *Science* 240:1759-64; Baxevanis and Vinson, 1993, *Curr. Op. Gen. Devel.* 3:278-285; O'Shea et al., 1989, *Science* 243:538-542.) In another embodiment, the dimerization domain is that of a basic-region helix-loop-helix ("bHLH") protein. (See, e.g., Murre et al., 1989, *Cell* 56:777-783. See also Davis et al., 1990, *Cell* 60:733-746; Voronova and Baltimore, 1990, *Proc. Natl. Acad. Sci. USA* 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0 367 166; and WO 96/04388.)

Heterodimers are known to form between Fos and Jun (Bohmann et al., 1987, *Science* 238:1386-1392), among members of the ATF/CREB family (Hai et al., 1989, *Genes Dev.* 3:2083-2090), among members of the C/EBP family (Cao et al., 1991, *Genes Dev.* 5:1538-52; Williams et al., 1991, *Genes Dev.* 5:1553-67; Roman et al., 1990, *Genes Dev.* 4:1404-15), and between members of the ATF/CREB and Fos/Jun families (Hai and Curran, 1991, *Proc. Natl. Acad. Sci. USA* 88:3720-24). Therefore, when a CD70-binding protein is administered to a subject as a heterodimer comprising different dimerization domains, any combination of the foregoing may be used.

In other embodiments, an anti-CD70 antibody derivative is an anti-CD70 antibody conjugated to a second antibody (an "antibody heteroconjugate") (see, e.g., U.S. Pat. No. 4,676,980). Heteroconjugates useful for practicing the present methods comprise an antibody that binds to CD70 (e.g., an antibody that has the CDRs and/or heavy chains of the monoclonal antibody 1F6) and an antibody that binds to a surface receptor or receptor complex that mediates ADCC, phagocytosis, and/or CDC, such as CD16/FcgRIII, CD64/FcgRI, killer cell activating or inhibitory receptors, or the complement control protein CD59. In a typical embodiment, the binding of the portion of the multispecific antibody to the second cell surface molecule or receptor complex enhances the effector functions of an anti-CD70 antibody. In other embodiments, the antibody can be a therapeutic agent. Suitable antibody therapeutic agents are described herein.

In some embodiments, any of the anti-CD70 antibodies described herein is nonfucosylated.

In some embodiments, provided herein is a population of anti-CD70 antibodies comprising a plurality of anti-CD70 antibodies as described herein, wherein the anti-CD70 antibodies in the population of anti-CD70 antibodies have reduced core fucosylation. In some embodiments, at least 20% of antibodies in the population of anti-CD70 antibodies lack core fucosylation. In some embodiments, at least 30% of antibodies in the population of anti-CD70 antibodies lack core fucosylation. In some embodiments, at least 40% of antibodies in the population of anti-CD70 antibodies lack core fucosylation. In some embodiments, at least 50% of antibodies in the population of anti-CD70 antibodies lack core fucosylation. In some embodiments, at least 60% of antibodies in the population of anti-CD70 antibodies lack core fucosylation. In some embodiments, at least 70% of antibodies in the population of anti-CD70 antibodies lack core fucosylation. In some embodiments, at least 80% of antibodies in the population of anti-CD70 antibodies lack core fucosylation. In some embodiments, at least 90% of antibodies in the population of anti-CD70 antibodies lack core fucosylation. In some embodiments, at least 95% of antibodies in the population of anti-CD70 antibodies lack core fucosylation. In some embodiments, at least 98% of antibodies in the population of anti-CD70 antibodies lack core fucosylation. In some embodiments, at least 99% of antibodies in the population of anti-CD70 antibodies lack core fucosylation. In some embodiments, at least 99.5% of antibodies in the population of anti-CD70 antibodies lack core fucosylation. In some embodiments, substantially none (i.e., less than 0.5%) of the antibodies in the population of anti-CD70 antibodies have core fucosylation. In some embodiments, all of the antibodies in the population of anti-CD70 antibodies lack core fucosylation.

As described in U.S. Pat. No. 10,196,445, modification of antibody glycosylation can be accomplished by, for example, expressing the antibody in a host cell with altered glycosylation machinery. Cells with altered glycosylation machinery have been described and can be used as host cells in which to express recombinant antibodies of this disclosure to thereby produce an antibody with altered glycosylation. For example, the cell lines Ms704, Ms705, and Ms709 lack the fucosyltransferase gene, FUT8 (α-(1,6) fucosyltransferase (see U.S. Pat. App. Publication No. 20040110704; Yamane-Ohnuki et al. (2004) *Biotechnol. Bioeng.* 87: 614), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB210 (ATCC CRL 1662), PCT Publication WO 03/035835 describes a variant CHO cell line, Lec13, with reduced ability to attach fucose to Asn(297)-linked carbohydrates, also resulting in hypofucosylation of antibodies expressed in that host cell. See also Shields et ail. (2002) *J. Biol. Chem.* 277:26733. Antibodies with a modified glycosylation profile can also be produced in chicken eggs, as described in PCT Publication No. WO 2006/089231. Alternatively, antibodies with a modified glycosylation profile can be produced in plant cells, such as Lemna. See e.g. U.S. Publication No, 2012/0276086. PCT Publication No, WO 99/54342 describes cell lines engineered to express glycoprotein-modifying glycosyl transferases (e.g., beta(1,4)-N-acetylglucosaminyltransferase III (Gram)) such that antibodies expressed in the engineered cell lines exhibit increased bisecting GlcNac structures which results in increased ADCC activity of the antibodies. See also Umaña et al. (1999) *Nat. Biotech.* 17:176. Alternatively, the fucose residues of the antibody may be cleaved off using E fucosidase enzyme. For example, the enzyme alpha-L-fucosidase removes fucosyl residues from antibodies. Tarentino a al. (1975) *Biochem.* 14:5516, Antibodies with reduced core fucosylation can be prepared by producing the antibodies in cell lines that have been engineered to reduce core fucosylation using gene knock-outs, gene knock-ins, or RNAi. Small molecule inhibitors that act on enzymes in the glycosylation pathway can also be used to generate antibodies with reduced core fucosylation. Such methods are described in U.S. Pat. No. 8,163,551. In some embodiments, anti-CD70 antibodies as described herein with reduced core fucosylation are generated by culturing a host cell expressing the antibodies in a culture medium comprising an effective amount of a fucose analog that reduces the incorporation of fucose into complex N-glycoside-linked sugar chains of antibodies or antibody derivatives produced by host cell. See U.S. Pat. No. 8,163,551.

Methods of producing nonfucosylated antibodies are also described in Pereira et al. (2018) *MAbs* 10(5):693-711.

In some embodiments, the anti-CD70 antibody or derivative thereof competitively inhibits binding of mAb 1F6 to CD70, as determined by any method known in the art for determining competitive binding (such as e.g., the immunoassays described herein). In typical embodiments, the antibody competitively inhibits binding of 1F6 to CD70 by at least 50%, at least 60%, at least 70%, or at least 75%. In other embodiments, the antibody competitively inhibits binding of 1F6 to CD70 by at least 80%, at least 85%, at least 90%, or at least 95%.

Antibodies can be assayed for specific binding to CD70 by any of various known methods. Immunoassays which can be used include, for example, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well-known in the art. (See, e.g., Ausubel et al., eds., *Short Protocols in Molecular Biology* (John Wiley and Sons, Inc., New York, 4th ed. 1999); Harlow and Lane, *Using Antibodies: A Laboratory Manual* (Cold Spring Harbor Laboratory Press, Cold Spring Harbor, N.Y., 1999.)

Further, the binding affinity of an antibody to CD70 and the off-rate of an antibody CD70 interaction can be determined by competitive binding assays. One example of a competitive binding assay is a radioimmunoas say comprising the incubation of labeled CD70 (e.g., $^3$H or $^{125}$I) with the antibody of interest in the presence of increasing amounts of unlabeled CD70, and the detection of the antibody bound to the labeled CD70. The affinity of the antibody for CD70 and the binding off-rates can then be determined from the data by Scatchard plot analysis. Competition with a second antibody (such as e.g., mAb 1F6) can also be determined using radioimmunoassays. In this case, CD70 is incubated with the antibody of interest conjugated to a labeled compound (e.g., $^3$H or $^{125}$I) in the presence of increasing amounts of an unlabeled second antibody. Alternatively, the binding affinity of an antibody to CD70 and the on- and off-rates of an antibody-CD70 interaction can be determined by surface plasmon resonance. In some embodiments, the anti-CD70 antibodies or derivatives thereof can be targeted to and accumulate on the membrane of a CD70-expressing cell.

Anti-CD70 antibodies and derivatives thereof can be produced by methods known in the art for the synthesis of proteins, typically, e.g., by recombinant expression techniques. Recombinant expression of an antibody or derivative thereof that binds to CD70 typically includes construction of an expression vector containing a nucleic acid that encodes the antibody or derivative thereof. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD70 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD70 antibody. In typical embodiments for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD70 antibody or derivative thereof. Typically, eukaryotic cells, particularly for whole recombinant anti-CD70 antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of anti-CD70 antibodies and derivatives thereof (see, e.g., Foecking et al., 1986, *Gene* 45:101; Cockett et al., 1990, *Bio/Technology* 8:2).

Other host-expression systems include, for example, plasmid-based expression systems in bacterial cells (see, e.g., Ruther et al., 1983, *EMBO* 1,2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of recombinant anti-CD70 antibody or derivative thereof or other CD70 binding agent. For example, cell lines that stably express the anti-CD70 antibody or derivative thereof can be engineered by transformation of host cells with DNA controlled by appropriate expression control elements (e.g., promoter and enhancer sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley and Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally, e.g., Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD70 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see Crouse et al., 1983, *Mol. Cell. Biol.* 3:257).

Where the anti-CD70 antibody comprises both a heavy and a light chain or derivatives thereof, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an anti-CD70 antibody or derivative thereof has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD70 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, *Cell* 37:767), and the "flag" tag.

Once an anti-CD70 antibody or derivative thereof is produced, its ability to exert a cytostatic or cytotoxic effect on CD70-expressing cancer cells or an immunomodulatory effect on a CD70-expressing immune cell is determined by the methods described infra or as known in the art.

To minimize activity of the anti-CD70 antibody outside the activated immune cells or CD70-expressing cancer cells, an antibody that specifically binds to cell membrane-bound CD70, but not to soluble CD70, can be used, so that the anti-CD70 antibody is concentrated at the cell surface of the activated immune cell or CD70-expressing cancer cell.

Typically, the anti-CD70 antibody or derivative is substantially purified (e.g., substantially free from substances that limit its effect or produce undesired side-effects). In some embodiments, the anti-CD70 antibody or derivative is at least about 40% pure, at least about 50% pure, or at least about 60% pure. In some embodiments, the anti-CD70 antibody or derivative is at least about 60-65%, 65-70%, 70-75%, 75-80%, 80-85%, 85-90%, 90-95%, or 95-98% pure. In some embodiments, the anti-CD70 antibody or derivative is approximately 99% pure.

III. Methods of Treatment

The invention provides methods of treating CD70-expressing cancers, such as myeloid malignancies, in a subject comprising administering to the subject a therapeutically effective amount of an anti-CD70 antibody, such as a nonfucosylated anti-CD70 antibody, as described herein. Myeloid malignancies include Acute Myeloid leukemia (AML), Myeloproliferative disorders (MPDS), myelodysplastic syndrome (MDS) and myelodysplastic/myeloproliferative syndromes that are all clonal stem-cell (HSC) or progenitor malignant disorders. In some embodiments, the cancer is MDS. In some embodiments, the cancer is AML. MDS encompasses multiple subtypes, including MDS with single-lineage dysplasia. AIDS with ring sideroblasts, MDS with multilineage dysplasia, MDS with excess blasts, MDS with isolated del(5q), and MDS, unclassifiable. MDS is characterized by ineffective hematopoiesis in one or more of the lineage of the bone marrow. Early MDS mostly demonstrate excessive apoptosis and hematopoietic cell dysplasia. In about a third of AIDS patients, this ineffective hematopoiesis precedes progression to secondary AMI, (sAML). AML is a malignant tumor of the myeloid lineage of white blood cells. In some embodiments, the method comprises administering a therapeutically effective amount of an nonfucosylated anti-CD70 antibody to the subject, wherein the anti-CD70 antibody comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain. In some embodiments, the method comprises administering a population of anti-CD70 antibodies to the subject, wherein at least 30% of the anti-CD70 antibodies in the population of the anti-CD70 antibodies lack core fucosylation. In some embodiments, the method comprises administering a population of anti-CD70 antibodies to the subject, wherein at least 40% of the anti-CD70 antibodies in the population of the anti-CD70 antibodies lack core fucosylation. In some embodiments, the method comprises administering a population of anti-CD70 antibodies to the subject, wherein at least 50% of the anti-CD70 antibodies in the population of the anti-CD70 antibodies lack core fucosylation. In some embodiments, the method comprises administering a population of anti-CD70 antibodies to the subject, wherein at least 60% of the anti-CD70 antibodies in the population of the anti-CD70 antibodies lack core fucosylation. In some embodiments, the method comprises administering a population of anti-CD70 antibodies to the subject, wherein at least 70% of the anti-CD70 antibodies in the population of the anti-CD70 antibodies lack core fucosylation. In some embodiments, the method comprises administering a population of anti-CD70 antibodies to the subject, wherein at least 80% of the anti-CD70 antibodies in the population of the anti-CD70 antibodies lack core fucosylation. In some embodiments, the method comprises administering a population of anti-CD70 antibodies to the subject, wherein at least 90% of the anti-CD70 antibodies in the population of the anti-CD70 antibodies lack core fucosylation. In some embodiments, the method comprises administering a population of anti-CD70 antibodies to the subject, wherein at least 95% of the anti-CD70 antibodies in the population of the anti-CD70 antibodies lack core fucosylation. In some embodiments, the method comprises administering a population of anti-CD70 antibodies to the subject, wherein at least 98% of the anti-CD70 antibodies in the population of the anti-CD70 antibodies lack core fucosylation. In some embodiments, the method comprises administering a population of anti-CD70 antibodies to the subject, wherein at least 99% of the anti-CD70 antibodies in the population of the anti-CD70 antibodies lack core fucosylation. In some embodiments, the method comprises administering a population of anti-CD70 antibodies to the subject, wherein at least 99.5% of the anti-CD70 antibodies in the population of the anti-CD70 antibodies lack core fucosylation. In some embodiments, the anti-CD70 antibody is administered in combination with a hypomethylating agent (HMA). In some embodiments, the HMA is azacitidine. In some embodiments, the anti-CD70 antibody is administered in combination with a BH3-mimetic. In some embodiments, the anti-CD70 antibody is administered in combination with venetoclax (VENCLEXTA®). In some embodiments, the anti-CD70 antibody is administered in combination with an HMA and a BH3-mimetic. In some embodiments, the anti-CD70 antibody is administered in combination with an HMA and venetoclax. In some embodiments, the anti-CD70 antibody is administered in combination with azacitidine and a BH3-mimetic. In some embodiments, the anti-CD70 antibody is administered in combination with azacitidine and a venetoclax.

In some embodiments, provided herein is a method of treating a CD70-expressing MDS in a subject comprising administering a therapeutically effective amount of an anti-CD70 antibody described herein. In some embodiments, the anti-CD70 antibody is nonfucosylated. In some embodiments, the MDS is relapsed or refractory MDS. In some embodiments, the MDS is relapsed MDS. In some embodiments, the MDS is refractory MDS. In some embodiments, the subject experienced treatment failure after prior hypomethylating agent (HMA) therapy for the MDS. A HMA (also known as a demethylating agent) is a drug that inhibits DNA methylation. In some embodiments, the HMA is a DNA methyltransferase inhibitor. In some embodiments, the HMA is azacitidine. In some embodiments, the HMA is decitabine.

In some embodiments, provided herein is a method of treating a CD70-expressing AML in a subject comprising administering a therapeutically effective amount of an anti-CD70 antibody described herein. In some embodiments, the anti-CD70 antibody is nonfucosylated. In some embodiments, the AML is relapsed or refractory AML. In some embodiments, the AML is relapsed AML. In some embodiments, the AML is refractory AML. In some embodiments, the subject received 1 prior treatment regimen to treat the AML. In some embodiments, the subject received 2 prior treatment regimens to treat the AML. In some embodiments, the subject received 3 prior treatment regimens to treat the AML.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cancer cells from the subject express CD70. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the cancer cells from the subject express CD70. In some embodiments, the percentage of cells that express CD70 is determined using immunohistochemistry (IHC). In some embodiments, the percentage of cells that express CD70 is determined using flow cytometry. In some embodiments, the percentage of cells that express CD70 is determined using an enzyme-linked immunosorbent assay (ELISA).

In one aspect, a method of treating cancer with an anti-CD70 antibody as described herein results in an improvement in one or more therapeutic effects in the subject after administration of the antibody relative to a baseline. In some embodiments, the one or more therapeutic effects is the objective response rate, the duration of response, the time to response, progression free survival, overall survival, or any combination thereof. In one embodiment, the one or more therapeutic effects is stable disease. In one embodiment, the one or more therapeutic effects is partial response. In one embodiment, the one or more therapeutic effects is complete response. In one embodiment, the one or more therapeutic effects is the objective response rate. In one embodiment, the one or more therapeutic effects is the duration of response. In one embodiment, the one or more therapeutic effects is the time to response. In one embodiment, the one or more therapeutic effects is progression free survival. In one embodiment, the one or more therapeutic effects is overall survival. In one embodiment, the one or more therapeutic effects is cancer regression.

In one embodiment of the methods or uses or product for uses provided herein, response to treatment with an anti-CD70 antibody as described herein may include the following criteria (Cheson criteria):

| Term | Definition (all criteria must be met unless otherwise specified)a |
|---|---|
| Morphologic complete remission (CR) | Absolute neutrophil count (ANC) ≥ 1000/μL and platelets ≥ 100,000/μL without transfusions and/or exogenous growth factor support (i.e., no transfusion or exogenous growth factor within 7 days of assessment).<br>Bone marrow with < 5% blasts<br>No evidence of extramedullary disease |

| Term | Definition (all criteria must be met unless otherwise specified)a |
| --- | --- |
| Morphologic complete remission with incomplete blood count recovery (CRi) | CRi(p)<br>(morphologic CR with incomplete platelet recovery)<br>Bone marrow with < 5% blasts<br>Platelets < 100,000/μL or ≥ 100,000/μL if subject transfused in last 7 days<br>ANC ≥ 1000/μL without exogenous growth factor support<br>No evidence of extramedullary disease<br>CRi(n)<br>(morphologic CR with incomplete neutrophil recovery)<br>Bone marrow with <5% blasts<br>ANC < 1000/μL or ANC ≥ 1000/μL with use of exogenous growth factors in last 7 days<br>Platelets ≥ 100,000/μL without transfusions in last 7 days<br>No evidence of extramedullary disease |
| Morphologic complete remission with partial hematologic recovery (CRh) | Bone marrow with < 5% blasts ANC > 500/μL and platelets ≥ 50,000/μL without transfusions and/or exogenous growth factor support in last 7 days without qualifying as full CR<br>No evidence of extramedullary disease |
| Morphologic leukemia free state (mLFS) | Bone marrow with < 5% blasts<br>No evidence of extramedullary disease<br>Criteria for blood count recovery not met for CR, CRi, or CRh |
| Partial remission (PR) | ANC ≥ 1000/μL and platelets ≥ 100,000/μL without transfusions and/or exogenous growth factor support (i.e., no transfusion or exogenous growth factor within 7 days of assessment).<br>Bone marrow with 5% to 25% blasts and at least a 50% decrease in bone marrow blast percent from baseline<br>No evidence of extramedullary disease |
| Antileukemic Effect | >25% reduction of bone marrow blasts relative to baseline and criteria for PR not met |
| Stable Disease (SD) | Absence of CR, CRi, CRh, mLFS, PR, or antileukemic effect. Criteria for progressive disease (PD) not met |
| Progressive Disease (PD) | >25% absolute rise in bone marrow blast percent from baseline or appearance of new extramedullary disease after 4 or more cycles of treatment. In subjects with baseline bone marrow blasts > 75%, a 25% proportional (instead of absolute) increase in bone marrow blasts is considered PD. |
| Relapse from CR/CRi/CRh | Reappearance of blasts in the blood (unless consistent with regenerating bone marrow), or bone marrow (>5%), or in any extramedullary site after achieving CR, CRi or CRh | aModified from the Revised Recommendations of the International Working Group for Diagnosis, Standardization of Response Criteria, Treatment Outcomes, and Reporting Standards for Therapeutic Trials in Acute Myeloid Leukemia (Cheson BD, Bennett JM, Kopecky KJ, Buchner T, Willman CL, Estey EH, Schiffer CA, Doehner H, Tallman MS, Lister TA, Lo-Coco F, Willemze R, Biondi A, Hiddemann W, Larson RA, Lowenberg B, Sanz MA, Head DR, Ohno R, Bloomfield CD (2003). Revised recommendations of the International Working Group for Diagnosis, Standardization of Response Criteria, Treatment Outcomes, and Reporting Standards for Therapeutic Trials in Acute Myeloid Leukemia. J Clin Oncol 21(24): 4642-9).

In one embodiment of the methods or uses or product for uses provided herein, response to treatment with an anti-CD70 antibody as described herein may include the following criteria (Cheson criteria):

| Category | Response criteria (responses must last at least 4 weeks) |
| --- | --- |
| Complete remission | Bone marrow ≤ 5% myeloblasts with normal maturation of all cell lines*<br>Persistent dysplasia will be noted*†<br>Peripheral blood‡<br>Hgb ≥ 11 g/dL<br>Platelets ≥ 100 × 10$_9$/L<br>Neutrophils ≥ 1.0 × 10$_9$/L†<br>Blasts 0% |
| Partial remission | All CR criteria if abnormal before treatment except:<br>Bone marrow blasts decreased by ≥ 50% over pretreatment but still > 5%<br>Cellularity and morphology not relevant |
| Marrow CR† | Bone marrow: ≤ 5% myeloblasts and decrease by ≥ 50% over pretreatment†<br>Peripheral blood: if HI responses, they will be noted in addition to<br>Marrow CR† |
| Stable disease | Failure to achieve at least PR, but no evidence of progression for > 8 weeks |
| Failure | Death during treatment or disease progression characterized by worsening of cytopenias, increase in percentage of bone marrow blasts, or progression to a more advanced MDS FAB subtype than pretreatment |
| Relapse after CR or PR | At least 1 of the following:<br>Return to pretreatment bone marrow blast percentage<br>Decrement of ≥ 50% from maximum remission/response levels in granulocytes or platelets<br>Reduction in Hgb concentration by ≥ 1.5 g/dL or transfusion dependence |

| Category | Response criteria (responses must last at least 4 weeks) |
| --- | --- |
| Cytogenetic response | Complete<br>Disappearance of the chromosomal abnormality without appearance of new ones<br>Partial<br>At least 50% reduction of the chromosomal abnormality |
| Disease progression | For subjects with:<br>Less than 5% blasts: ≥ 50% increase in blasts to > 5% blasts<br>5%-10% blasts: ≥ 50% increase in blasts to > 10% blasts<br>10%-20% blasts ≥ 50% increase in blasts to > 20% blasts<br>20%-30% blasts ≥ 50% increase in blasts to > 30% blasts<br>Any of the following:<br>At least 50% decrement from maximum remission/response in granulocytes or platelets<br>Reduction in Hgb by ≥ 2 g/dL<br>Transfusion dependence |
| Survival | Endpoints:<br>Overall: death from any cause<br>Event free: failure or death from any cause<br>PFS: disease progression or death from MDS<br>DFS: time to relapse<br>Cause-specific death: death related to MDS |

Deletions to IWG response criteria are not shown.
To convert hemoglobin from grams per deciliter to grams per liter, multiply grams per deciliter by 10. MDS indicates myelodysplastic syndromes; Hgb, hemoglobin; CR, complete remission; HI, hematologic improvement; PR, partial remission; FAB, French-American-British; PFS, progression-free survival; DFS, disease-free survival.
*Dysplastic changes should consider the normal range of dysplastic changes (modification). (Ramos F, Fernandez-Ferrero S, Suarez D, et al. Myelodysplastic syndrome: a search for minimal diagnostic criteria. Leuk Res. 1999;23:283-290)
†Modification to IWG response criteria.
‡In some circumstances, protocol therapy may require the initiation of further treatment (e.g., consolidation, maintenance) before the 4-week period. Such subjects can be included in the response category into which they fit at the time the therapy is started. Transient cytopenias during repeated chemotherapy courses should not be considered as interrupting durability of response, as long as they recover to the improved counts of the previous course. (Cheson BD, Greenberg PL, Bennett JM, Lowenberg B, Wijermans PW, Nimer SD, Pinto A, Beran M, de Witte TM, Stone RM, Mittelman M, Sanz GF, Gore SD, Schiffer CA, Kantarjian H (2006). Clinical application and proposal for modification of the International Working Group (IWG) response criteria in myelodysplasia. Blood 108(2): 419-25).

| Hematologic Improvement[a] | Response criteria (responses must last at least 8 weeks)[b] |
| --- | --- |
| Erythroid response (pretreatment, < 11 g/dL) | Hgb increase by ≥ 1.5 g/dL<br>Relevant reduction of units of RBC transfusions by an absolute number of at least 4 RBC transfusion per 8 week compared with the pretreatment transfusion number in the previous 8 weeks. Only RBC transfusions given for a Hgb of ≤ 9.0 g/dL pretreatment will count in the RBC transfusion response evaluation |
| Platelet response (pretreatment, < 100 × 10$^9$/L) | Absolute increase of ≥ 30 × 10$^9$/L for subjects starting with > 20 × 10$^9$/L platelets<br>Increase from < 20 × 10$^9$/L to > 20 × 10$^9$/L and by at least 100%[b] |
| Neutrophil response (pretreatment, < 1.0 × 10$_9$/L) | At least 100% increase and an absolute increase > 0.5 × 10$^9$/L[b] |
| Progression or relapse after HI[c] | At least 1 of the following:<br>At least 50% decrement from maximum response levels in granulocytes or platelets<br>Reduction in Hgb by ≥ 1.5 g/dL<br>Transfusion dependence |

RBC = red blood cell
[a]Pretreatment counts average of at least 2 measurements (not influenced by transfusions) ≥ 1 week apart (modification).
[b]Modification to IWG response criteria.
[c]In the absence of another explanation, such as acute infection, repeated courses of chemotherapy (modification), gastrointestinal bleeding, hemolysis, and so forth. It is recommended that 2 kinds of erythroid and platelet responses be reported overall as well as by the individual response pattern (Cheson 2006)

In one embodiment of the methods or uses or product for uses provided herein, the effectiveness of treatment with an anti-CD70 antibody as described herein is assessed by measuring the objective response rate. In some embodiments, the objective response rate is the proportion of patients with tumor size reduction of a predefined amount and for a minimum period of time. In some embodiments the objective response rate is based upon Cheson criteria. In one embodiment, the objective response rate is at least about 20%, at least about 25%, at least about 30%, at least about 35%, at least about 40%, at least about 45%, at least about 50%, at least about 60%, at least about 70%, or at least about 80%. In one embodiment, the objective response rate is at least about 20%-80%. In one embodiment, the objective response rate is at least about 30%-80%. In one embodiment, the objective response rate is at least about 40%-80%. In one embodiment, the objective response rate is at least about 50%-80%. In one embodiment, the objective response rate is at least about 60%-80%. In one embodiment, the objective response rate is at least about 70%-80%. In one embodiment, the objective response rate is at least about 80%. In one embodiment, the objective response rate is at least about 85%. In one embodiment, the objective response rate is at least about 90%. In one embodiment, the objective response rate is at least about 95%. In one embodiment, the objective response rate is at least about 98%. In one embodiment, the objective response rate is at least about 99%. In one embodiment, the objective response rate is at least 20%, at least 25%, at least 30%, at least 35%, at least 40%, at least 45%, at least 50%, at least 60%, at least 70%, or at least 80%. In one embodiment, the objective response rate is at least 20%-80%. In one embodiment, the objective response rate is at least 30%-80%. In one embodiment, the objective response rate is at least 40%-80%. In one embodiment, the objective response rate is at least 50%-80%. In one embodiment, the objective response rate is at least 60%-80%. In one embodiment, the objective response rate is at least 70%-80%. In one embodiment, the objective response rate is at least 80%. In one embodiment, the objective response rate is at least 85%. In one embodiment, the objective response rate is at least 90%. In one embodiment, the objective response rate is at least 95%. In one embodiment, the objective response rate is at least 98%. In one embodiment, the objective response rate is at least 99%. In one embodiment, the objective response rate is 100%.

In one embodiment of the methods or uses or product for uses described herein, response to treatment with an anti-CD70 antibody as described herein is assessed by measuring the time of progression free survival after administration of the anti-CD70 antibody described herein. In some embodiments, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-CD70 antibody described herein. In some embodiments, the subject exhibits progression-free survival of at least about 6 months after administration of the anti-CD70 antibody described herein. In some embodiments, the subject exhibits progression-free survival of at least about one year after administration of the anti-CD70 antibody described herein. In some embodiments, the subject exhibits progression-free survival of at least about two years after administration of the anti-CD70 antibody described herein. In some embodiments, the subject exhibits progression-free survival of at least about three years after administration of the anti-CD70 antibody described herein. In some embodiments, the subject exhibits progression-free survival of at least about four years after administration of the anti-CD70 antibody described herein. In some embodiments, the subject exhibits progression-free survival of at least about five years after administration of the anti-CD70 antibody described herein. In some embodiments, the subject exhibits progression-free survival of at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-CD70 antibody described herein. In some embodiments, the subject exhibits progression-free survival of at least 6 months after administration of the anti-CD70 antibody described herein. In some embodiments, the subject exhibits progression-free survival of at least one year after administration of the anti-CD70 antibody described herein. In some embodiments, the subject exhibits progression-free survival of at least two years after administration of the anti-CD70 antibody described herein. In some embodiments, the subject exhibits progression-free survival of at least three years after administration of the anti-CD70 antibody described herein. In some embodiments, the subject exhibits progression-free survival of at least four years after administration of the anti-CD70 antibody described herein. In some embodiments, the subject exhibits progression-free survival of at least five years after administration of the anti-CD70 antibody described herein.

In one embodiment of the methods or uses or product for uses described herein, response to treatment with an anti-CD70 antibody described herein is assessed by measuring the time of overall survival after administration of the anti-CD70 antibody described herein. In some embodiments, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-CD70 antibody described herein. In some embodiments, the subject exhibits overall survival of at least about 6 months after administration of the anti-CD70 antibody described herein. In some embodiments, the subject exhibits overall survival of at least about one year after administration of the anti-CD70 antibody described herein. In some embodiments, the subject exhibits overall survival of at least about two years after administration of the anti-CD70 antibody described herein. In some embodiments, the subject exhibits overall survival of at least about three years after administration of the anti-CD70 antibody described herein. In some embodiments, the subject exhibits overall survival of at least about four years after administration of the anti-CD70 antibody described herein. In some embodiments, the subject exhibits overall survival of at least about five years after administration of the anti-CD70 antibody described herein. In some embodiments, the subject exhibits overall survival of at least 1 month, at least 2 months, at least 3 months, at least 4 months, at least 5 months, at least 6 months, at least 7 months, at least 8 months, at least 9 months, at least 10 months, at least 11 months, at least about 12 months, at least eighteen months, at least two years, at least three years, at least four years, or at least five years after administration of the anti-CD70 antibody described herein. In some embodiments, the subject exhibits overall survival of at least 6 months after administration of the anti-CD70 antibody described herein. In some embodiments, the subject exhibits overall survival of at least one year after administration of the anti-CD70 antibody described herein. In some embodiments, the subject exhibits overall survival of at least two years after administration of the anti-CD70 antibody described herein. In some embodiments, the subject exhibits overall survival of at least three years after administration of the anti-CD70 antibody described herein. In some embodiments, the subject exhibits overall survival of at least four years after administration of the anti-CD70 antibody described herein. In some embodiments, the subject exhibits overall survival of at least five years after administration of the anti-CD70 antibody described herein.

In one embodiment of the methods or uses or product for uses described herein, response to treatment with an anti-CD70 antibody described herein is assessed by measuring the duration of response to the anti-CD70 antibody described herein after administration of the anti-CD70 antibody described herein. In some embodiments, the duration of response to the anti-CD70 antibody described herein is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-CD70 antibody described herein. In some embodiments, the duration of response to the anti-CD70 antibody described herein is at least about 6 months after administration of the anti-CD70 antibody described herein. In some embodiments, the duration of response to the anti-CD70 antibody described herein is at least about one year after administration of the anti-CD70 antibody described herein. In some embodiments, the duration of response to the anti-CD70 antibody described herein is at least about two years after administration of the anti-CD70 antibody described herein. In some embodiments, the duration of response to the anti-CD70 antibody described herein is at least about three years after administration of the anti-CD70 antibody described herein. In some embodiments, the duration of response to the anti-CD70 antibody described herein is at least about four years after administration of the anti-CD70 antibody described herein. In some embodiments, the duration of response to the anti-CD70 antibody described herein is at least about five years after administration of the anti-CD70 antibody described herein. In some embodiments, the duration of response to the anti-CD70 antibody described herein is at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-CD70 antibody described herein. In some embodiments, the duration of response to the anti-CD70 antibody described herein is at least 6 months after administration of the anti-CD70 antibody described herein. In some embodiments, the duration of response to the anti-CD70 antibody described herein is at least one year after administration of the anti-CD70 antibody described herein. In some embodiments, the duration of response to the anti-CD70 antibody described herein is at least two years after administration of the anti-CD70 antibody described herein. In some embodiments, the duration of response to the anti-CD70 antibody described herein is at least three years after administration of the anti-CD70 antibody described herein. In some embodiments, the duration of response to the anti-CD70 antibody described herein is at least four years after administration of the anti-CD70 antibody described herein. In some embodiments, the duration of response to the anti-CD70 antibody described herein is at least five years after administration of the anti-CD70 antibody described herein.

In some embodiments of the methods or uses or product for uses described herein, administering an anti-CD70 antibody described herein, such as a nonfucosylated anti-CD70 antibody, to a subject results in a depletion of cancer cells in the subject. In some embodiments, administering an anti-CD70 antibody described herein, such as a nonfucosylated anti-CD70 antibody, results in a depletion of cancer cells by at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or about 100% compared to the amount of cancer cells before administering the anti-CD70 antibody to the subject. In some embodiments, the cancer cells are depleted by at least about 5% compared to the amount of cancer cells before administering the anti-CD70 antibody to the subject. In some embodiments, the cancer cells are depleted by at least about 10% compared to the amount of cancer cells before administering the anti-CD70 antibody to the subject. In some embodiments, the cancer cells are depleted by at least about 20% compared to the amount of cancer cells before administering the anti-CD70 antibody to the subject. In some embodiments, the cancer cells are depleted by at least about 30% compared to the amount of cancer cells before administering the anti-CD70 antibody to the subject. In some embodiments, the cancer cells are depleted by at least about 40% compared to the amount of cancer cells before administering the anti-CD70 antibody to the subject. In some embodiments, the cancer cells are depleted by at least about 50% compared to the amount of cancer cells before administering the anti-CD70 antibody to the subject. In some embodiments, the cancer cells are depleted by at least about 60% compared to the amount of cancer cells before administering the anti-CD70 antibody to the subject. In some embodiments, the cancer cells are depleted by at least about 70% compared to the amount of cancer cells before administering the anti-CD70 antibody to the subject. In some embodiments, the cancer cells are depleted by at least about 80% compared to the amount of cancer cells before administering the anti-CD70 antibody to the subject. In some embodiments, the cancer cells are depleted by at least about 90% compared to the amount of cancer cells before administering the anti-CD70 antibody to the subject. In some embodiments, the cancer cells are depleted by at least about 95% compared to the amount of cancer cells before administering the anti-CD70 antibody to the subject. In some embodiments, the cancer cells are depleted by at least about 99% compared to the amount of cancer cells before administering the anti-CD70 antibody to the subject. In some embodiments, the cancer cells are depleted by about 100% compared to the amount of cancer cells before administering the anti-CD70 antibody to the subject. In some embodiments, administering an anti-CD70 antibody described herein, such as a nonfucosylated anti-CD70 antibody, results in a depletion of cancer cells by at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least about 80%, at least about 90%, at least 95%, or 100% compared to the amount of cancer cells before administering the anti-CD70 antibody to the subject. In some embodiments, the cancer cells are depleted by at least 5% compared to the amount of cancer cells before administering the anti-CD70 antibody to the subject. In some embodiments, the cancer cells are depleted by at least 10% compared to the amount of cancer cells before administering the anti-CD70 antibody to the subject. In some embodiments, the cancer cells are depleted by at least 20% compared to the amount of cancer cells before administering the anti-CD70 antibody to the subject. In some embodiments, the cancer cells are depleted by at least 30% compared to the amount of cancer cells before administering the anti-CD70 antibody to the subject. In some embodiments, the cancer cells are depleted by at least 40% compared to the amount of cancer cells before administering the anti-CD70 antibody to the subject. In some embodiments, the cancer cells are depleted by at least 50% compared to the amount of cancer cells before administering the anti-CD70 antibody to the subject. In some embodiments, the cancer cells are depleted by at least 60% compared to the amount of cancer cells before administering the anti-CD70 antibody to the subject. In some embodiments, the cancer cells are depleted by at least 70% compared to the amount of cancer cells before administering the anti-CD70 antibody to the subject. In some embodiments, the cancer cells are depleted by at least 80% compared to the amount of cancer cells before administering the anti-CD70 antibody to the subject. In some embodiments, the cancer cells are depleted by at least 90% compared to the amount of cancer cells before administering the anti-CD70 antibody to the subject. In some embodiments, the cancer cells are depleted by at least 95% compared to the amount of cancer cells before administering the anti-CD70 antibody to the subject. In some embodiments, the cancer cells are depleted by at least 99% compared to the amount of cancer cells before administering the anti-CD70 antibody to the subject. In some embodiments, the cancer cells are depleted by 100% compared to the amount of cancer cells before administering the anti-CD70 antibody to the subject.

In some embodiments of the methods or uses or product for uses described herein, administering an anti-CD70 antibody described herein, such as a nonfucosylated anti-CD70 antibody, to a subject does not result in a depletion of CD70+ T regulatory cells (CD70+ Tregs) in the subject. In some embodiments, administering an anti-CD70 antibody described herein, such as a nonfucosylated anti-CD70 antibody, results in a depletion of CD70+ Tregs of no more than about 50%, about 40%, about 30%, about 20%, about 10%, about 9%, about 8%, about 7%, about 6%, about 5%, about 4%, about 3%, about 2%, about 1%, or about 0.1% compared to the amount of CD70+ Tregs before administering the anti-CD70 antibody to the subject. In some embodiments, the CD70+ Tregs are depleted by no more than about 50% compared to the amount of CD70+ Tregs before administering the anti-CD70 antibody to the subject. In some embodiments, the CD70+ Tregs are depleted by no more than about 40% compared to the amount of CD70+ Tregs before administering the anti-CD70 antibody to the subject. In some embodiments, the CD70+ Tregs are depleted by no more than about 30% compared to the amount of CD70+ Tregs before administering the anti-CD70 antibody to the subject. In some embodiments, the CD70+ Tregs are depleted by no more than about 20% compared to the amount of CD70+ Tregs before administering the anti-CD70 antibody to the subject. In some embodiments, the CD70+ Tregs are depleted by no more than about 10% compared to the amount of CD70+ Tregs before administering the anti-CD70 antibody to the subject. In some embodiments, the CD70+ Tregs are depleted by no more than about 5% compared to the amount of CD70+ Tregs before administering the anti-CD70 antibody to the subject. In some embodiments, the CD70+ Tregs are depleted by no more than about 1% compared to the amount of CD70+ Tregs before administering the anti-CD70 antibody to the subject. In some embodiments, the CD70+ Tregs are depleted by no more than about 0.1% compared to the amount of CD70+ Tregs before administering the anti-CD70 antibody to the subject. In some embodiments, administering an anti-CD70 antibody described herein, such as a nonfucosylated anti-CD70 antibody, results in a depletion of CD70+ Tregs of no more than 50%, 40%, 30%, 20%, 10%, 9%, 8%, 7%, 6%, 5%, 4%, 3%, 2%, 1%, or 0.1% compared to the amount of CD70+Tregs before administering the anti-CD70 antibody to the subject. In some embodiments, the CD70+ Tregs are depleted by no more than 50% compared to the amount of CD70+ Tregs before administering the anti-CD70 antibody to the subject. In some embodiments, the CD70+Tregs are depleted by no more than 40% compared to the amount of CD70+ Tregs before administering the anti-CD70 antibody to the subject. In some embodiments, the CD70+ Tregs are depleted by no more than 30% compared to the amount of CD70+ Tregs before administering the anti-CD70 antibody to the subject. In some embodiments, the CD70+ Tregs are depleted by no more than 20% compared to the amount of CD70+ Tregs before administering the anti-CD70 antibody to the subject. In some embodiments, the CD70+ Tregs are depleted by no more than 10% compared to the amount of CD70+ Tregs before administering the anti-CD70 antibody to the subject. In some embodiments, the CD70+ Tregs are depleted by no more than 5% compared to the amount of CD70+ Tregs before administering the anti-CD70 antibody to the subject. In some embodiments, the CD70+ Tregs are depleted by no more than 1% compared to the amount of CD70+ Tregs before administering the anti-CD70 antibody to the subject. In some embodiments, the CD70+ Tregs are depleted by no more than 0.1% compared to the amount of CD70+ Tregs before administering the anti-CD70 antibody to the subject.

In some embodiments, the fucosylated anti-CD70 antibody depletes CD70+ Tregs in a subject to a greater extent than the nonfucosylated form of an anti-CD70 antibody comprising the same heavy and light chain amino acid sequences. In some embodiments, the fucosylated anti-CD70 antibody depletes CD70+ Tregs in a subject to a greater extent than the nonfucosylated form of an anti-CD70 antibody comprising the same heavy and light chain amino acid sequences when the subject is homozygous for the high affinity FcγRIIIa receptor (V/V 158). In some embodiments, the fucosylated anti-CD70 antibody depletes CD70+ Tregs in a subject to the same extent as the nonfucosylated form of an anti-CD70 antibody comprising the same heavy and light chain amino acid sequences when the subject is homozygous for the low affinity FcγRIIIa receptor (F/F 158). In some embodiments, neither the fucosylated anti-CD70 antibody nor the nonfucosylated form of an anti-CD70 antibody comprising the same heavy and light chain amino acid sequences deplete CD8 T cells when the subject is homozygous for the high affinity FcγRIIIa receptor (V/V 158). In some embodiments, neither the fucosylated anti-CD70 antibody nor the nonfucosylated form of an anti-CD70 antibody comprising the same heavy and light chain amino acid sequences deplete CD8 T cells when the subject is homozygous for the low affinity FcγRIIIa receptor (F/F 158).

IV. Assays for Cytotoxic, Cytostatic, and Immunomodulatory Activities

Methods of determining whether an antibody mediates effector function against a target cell are known. Illustrative examples of such methods are described infra.

For determining whether an anti-CD70 antibody mediates antibody-dependent cellular cytotoxicity against activated immune cells or CD70-expressing cancer cells, an assay that measures target cell death in the presence of antibody and effector immune cells may be used. An assay used to measure this type of cytotoxicity can be based on determination of $^{51}$Cr release from metabolically-labeled targets cells after incubation in the presence of effector cells and target-specific antibody (see, e.g., Perussia and Loza, 2000, *Methods in Molecular Biology* 121:179-92; and "$^{51}$Cr Release Assay of Antibody-Dependent Cell-Mediated Cytotoxicity (ADCC)" in *Current Potocols in Immunology*, Coligan et al. eds., Wileyand Sons, 1993). For example, activated immune cells (e.g., activated lymphocytes) or CD70-expressing cancer cells labeled with $Na_2^{51}CrO_4$ and plated at a density of 5,000 cells per well of a 96-well plate can be treated with varying concentrations of anti-CD70 antibody for 30 minutes then mixed with normal human peripheral blood mononuclear cells (PB MC) for 4 hours. The membrane disruption that accompanies target cell death releases $^{51}$Cr into the culture supernatant which may be collected and assessed for radioactivity as a measure of cytotoxic activity. Other assays to measure ADCC may involve nonradioactive labels or be based on induced release of specific enzymes. For example, a non-radioactive assay based on time-resolved fluorometry is commercially available (Delphia, Perkin Elmer). This assay is based on loading target cells with an acetoxymethyl ester of fluorescence enhancing ligand (BATDA) that penetrates the cell membrane then hydrolyses to form a membrane impermeable hydrophilic ligand (TDA). When mixed with target specific antibody and PBMC effector cells, TDA is released from lysed cells and is available to form a highly fluorescent chelate when mixed with Europium. The signal, measured with a time-resolved fluorometer, correlates with the amount of cell lysis.

To determine whether an anti-CD70 antibody mediates antibody-dependent cellular phagocytosis against activated immune cells or CD70-expressing cancer cells, an assay that measures target cell internalization by effector immune cells (e.g., fresh cultured macrophages or established macrophage-like cell line) may be used (see, e.g., Munn and Cheung, 1990, *J. Exp. Med.* 172:231-37; Keler et al., 2000, *J. Immunol.* 164:5746-52; Akewanlop et al., 2001, *Cancer Res.* 61:4061-65). For example, target cells may be labeled with a lipophilic membrane dye such as PKH67 (Sigma), coated with target-specific antibody, and mixed with effector immune cells for 4-24 hours. The effector cells may then be identified by counterstaining with a fluorochrome-labeled antibody specific for a phagocytic cell surface marker (e.g., CD14) and the cells analyzed by two-color flow cytometry or fluorescence microscopy. Dual-positive cells represent effector cells that have internalized target cells. For these assays, effector cells may be monocytes derived from PBMC that have been differentiated into macrophages by culture for 5-10 days with M-CSF or GM-CSF (see, e.g., Munn and Cheung, supra). Human macrophage-like cell lines U937 (Larrick et al., 1980, *J. Immunology* 125:6-12) or THP-1 (Tsuchiya et al., 1980, *Int. J. Cancer* 26:171-76) which are available from ATCC may be used as an alternative phagocytic cell source.

Methods of determining whether an antibody mediates complement-dependent cytotoxicity upon binding to target cells are also known. The same methods can be applied to determine whether anti-CD70 antibody mediates CDC on activated immune cells or CD70-expressing cancer cells. Illustrative examples of such methods are described infra.

The source of active complement can either be normal human serum or purified from laboratory animal including rabbits. In a standard assay, an anti-CD70 antibody is incubated with CD70-expressing activated immune cells (e.g., activated lymphocytes) or CD70-expressing cancer cells in the presence of complement. The ability of such an anti-CD70 antibody to mediate cell lysis can be determined by several readouts. In one example, a $Na^{51}CrO_4$ release assay is used. In this assay, target cells are labeled with $Na^{51}CrO_4$. Unincorporated $Na^{51}CrO_4$ is washed off and cells are plated at a suitable density, typically between 5,000 to 50,000 cells/well, in a 96-well plate. Incubation with the anti-CD70 antibody in the presence of normal serum or purified complement typically last for 2-6 hours at 37° C. in a 5% $CO_2$ atmosphere. Released radioactivity, indicating cell lysis, is determined in an aliquot of the culture supernatant by gamma ray counting. Maximum cell lysis is determined by releasing incorporated $Na^{51}CrO_4$ by detergent (0.5-1% NP-40 or Triton X-100) treatment. Spontaneous background cell lysis is determined in wells where only complement is present without any anti-CD70 antibodies. Percentage cell lysis is calculated as (anti-CD70 antibody-induced lysis—spontaneous lysis)/maximum cell lysis). The second readout is a reduction of metabolic dyes, e.g., Alamar Blue, by viable cells. In this assay, target cells are incubated with anti-CD70 antibodies with complement and incubated as described above. At the end of incubation, 1/10 volume of Alamar Blue (Biosource International, Camarillo, Calif.) is added. Incubation is continued for up to 16 hours at 37° C. in a 5% $CO_2$ atmosphere. Reduction of Alamar Blue as an indication of metabolically active viable cells is determined by fluorometric analysis with excitation at 530 nm and emission at 590 nm. The third readout is cellular membrane permeability to propidium iodide (PI). Formation of pores in the plasma membrane as a result of complement activation facilitates entry of PI into cells where it will diffuse into the nuclei and bind DNA. Upon binding to DNA, PI fluorescence in the 600 nm significantly increases. Treatment of target cells with anti-CD70 antibodies and complement is carried out as described above. At end of incubation, PI is added to a final concentration of 5 μg/ml. The cell suspension is then examined by flow cytometry using a 488 nm argon laser for excitation. Lysed cells are detected by fluorescence emission at 600 nm.

V. Pharmaceutical Compositions Comprising Anti-CD70 Antibodies and Administration Thereof A composition comprising an anti-CD70 antibody can be administered to a subject having or at risk of having a CD70-expressing cancer. The invention further provides for the use of an anti-CD70 antibody in the manufacture of a medicament for prevention or treatment of a CD70-expressing cancer. The term "subject" as used herein means any mammalian patient to which a CD70-binding agent can be administered, including, e.g., humans and non-human mammals, such as primates, rodents, and dogs. Subjects specifically intended for treatment using the methods described herein include humans. The antibodies can be administered either alone or in combination with other compositions in the prevention or treatment of the CD70-expressing cancer.

Various delivery systems are known and can be used to administer the anti-CD70 antibody. Methods of introduction include but are not limited to intradermal, intramuscular, intraperitoneal, intravenous, subcutaneous, intranasal, epidural, and oral routes. The anti-CD70 antibody can be administered, for example by infusion or bolus injection (e.g., intravenous or subcutaneous), by absorption through epithelial or mucocutaneous linings (e.g., oral mucosa, rectal and intestinal mucosa, and the like) and can be administered together with other biologically active agents such as chemotherapeutic agents. Administration can be systemic or local. In one embodiment, the anti-CD70 antibody described herein is administered parenterally. Parenteral administration refers to modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In some embodiments, the route of administration of an anti-CD70 antibody described herein is intravenous injection or infusion. In some embodiments, the route of administration of an anti-CD70 antibody described herein is intravenous infusion.

In specific embodiments, the anti-CD70 antibody composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-CD70 antibody does not absorb are used.

An anti-CD70 antibody can be administered as pharmaceutical compositions comprising a therapeutically effective amount of the antibody and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-CD70 antibody in lyophilized form and (b) a second container containing a pharmaceutically acceptable diluent (e.g., sterile water) for injection. The pharmaceutically acceptable diluent can be used for reconstitution or dilution of the lyophilized anti-CD70 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-CD70 antibody that is effective in the treatment or prevention of the CD70-expressing cancer can be determined by standard clinical techniques. In addition, in vitro assays may optionally be employed to help identify optimal dosage ranges. The precise dose to be employed in the formulation will also depend on the route of administration, and the stage of the CD70-expressing cancer, and should be decided according to the judgment of the practitioner and each patient's circumstances. Effective doses may be extrapolated from dose-response curves derived from in vitro or animal model test systems.

For example, toxicity and therapeutic efficacy of the anti-CD70 antibody can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-CD70 antibody that exhibits a large therapeutic index is preferred. Where an anti-CD70 antibody exhibits toxic side effects, a delivery system that targets the anti-CD70 antibody to the site of affected tissue can be used to minimize potential damage to non-CD70-expressing cells and, thereby, reduce side effects.

The data obtained from the cell culture assays and animal studies can be used in formulating a range of dosage for use in humans. The dosage of the anti-CD70 antibody typically lies within a range of circulating concentrations that include the $ED_{50}$ with little or no toxicity. The dosage may vary within this range depending upon the dosage form employed and the route of administration utilized. For an anti-CD70 antibody used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD70 antibody administered to a patient with a CD70-expressing cancer is about 0.1 mg/kg to 100 mg/kg of the subject's body weight. More typically, the dosage administered to a subject is 0.1 mg/kg to 50 mg/kg of the subject's body weight, even more typically 1 mg/kg to 30 mg/kg, 1 mg/kg to 20 mg/kg, 1 mg/kg to 15 mg/kg, 1 mg/kg to 12 mg/kg, 1 mg/kg to 10 mg/kg, or 1 mg/kg to 7.5 mg/kg of the subject's body weight. In some embodiments, the dose of an anti-CD70 antibody is 1.5 mg/kg. In some embodiments, the dose is 5 mg/kg. In some embodiments, the dose is 10 mg/kg. In some embodiments, the dose is 20 mg/kg. Generally, human antibodies have a longer half-life within the human body than antibodies from other species due to the immune response to the foreign proteins. Thus, lower dosages of anti-CD70 antibody comprising humanized or chimeric antibodies and less frequent administration is often possible.

A dose of an anti-CD70 antibody can be administered, for example, daily, once per week (weekly), twice per week, thrice per week, four times per week, five times per week, biweekly, monthly or otherwise as needed.

In some embodiments, the dosage of an anti-CD70 antibody corresponds to a sub-optimal dosage (i.e., below the $EC_{50}$ for the anti-CD70 antibody. For example, the dosage of an anti-CD70 antibody can comprise a dosage selected from the lowest 25%, lowest 15%, lowest 10% or lowest 5% of the therapeutic window. As used herein, the term "therapeutic window" refers to the range of dosage of a drug or of its concentration in a bodily system that provides safe and effective therapy.

In some embodiments, the dosage of an anti-CD70 antibody is from about 0.05 mg/kg to about 1 mg/kg, or about 0.1 mg/kg to about 0.9 mg/kg, or about 0.15 to about 0.75 mg/kg of the subject's body weight. Such a dosage can be administered from 1 to about 15 times per week. Each dose can be the same or different. For example, a dosage of about 0.15 mg/kg of an anti-CD70 antibody can be administered from 1 to 10 times per four day, five day, six day or seven day period.

In some embodiments, the pharmaceutical compositions comprising the anti-CD70 antibody can further comprise a therapeutic agent (e.g., a non-conjugated cytotoxic or immunomodulatory agent such as, for example, any of those described herein). The anti-CD70 binding agent also can be co-administered in combination with one or more therapeutic agents for the treatment or prevention of CD70-expressing cancers. For example, combination therapy can include a therapeutic agent (e.g., a cytostatic, cytotoxic, or immunomodulatory agent, such as an unconjugated cytostatic, cytotoxic, or immunomodulatory agent such as those conventionally used for the treatment of cancers). Combination therapy can also include, e.g., administration of an agent that targets a receptor or receptor complex other than CD70 on the surface of activated lymphocytes, dendritic cells or CD70-expressing cancer cells. An example of such an agent includes a second, non-CD70 antibody that binds to a molecule at the surface of an activated lymphocyte, dendritic cell or CD70-expressing cancer cell. Another example includes a ligand that targets such a receptor or receptor complex. Typically, such an antibody or ligand binds to a cell surface receptor on activated lymphocytes, dendritic cell or CD70-expressing cancer cell and enhances the cytotoxic or cytostatic effect of the anti-CD70 antibody by delivering a cytostatic or cytotoxic signal to the activated lymphocyte, dendritic cell or CD70-expressing cancer cell. Such combinatorial administration can have an additive or synergistic effect on disease parameters (e.g., severity of a symptom, the number of symptoms, or frequency of relapse). Another example includes a hypomethylating agent (HMA). In some embodiments, the HMA is azacitidine (VIDAZA®). Another example includes a BH3-mimetic. Another example includes venetoclax (VENCLEXTA®). In some embodiments, the pharmaceutical composition comprises an anti-CD70 antibody, an HMA and a BH3-mimetic. In some embodiments, the pharmaceutical composition comprises an anti-CD70 antibody, an HMA and venetoclax. In some embodiments, the pharmaceutical composition comprises an anti-CD70 antibody, azacitidine and a BH3-mimetic. In some embodiments, the pharmaceutical composition comprises an anti-CD70 antibody, azacitidine and a venetoclax.

With respect to therapeutic regimens for combinatorial administration, in a specific embodiment, an anti-CD70 antibody is administered concurrently with a therapeutic agent. In another specific embodiment, the therapeutic agent is administered prior or subsequent to administration of the anti-CD70 antibody, by at least an hour and up to several months, for example at least an hour, five hours, 12 hours, a day, a week, a month, or three months, prior or subsequent to administration of the anti-CD70 antibody. In some embodiments, the subject is monitored following administration of the anti-CD70 antibody, and optionally the therapeutic agent.

VI. Articles of Manufacture and Kits

In another aspect, an article of manufacture or kit is provided which comprises an anti-CD70 antibody described herein. The article of manufacture or kit may further comprise instructions for use of the anti-CD70 antibody described herein in the methods of the invention. Thus, in certain embodiments, the article of manufacture or kit comprises instructions for the use of an anti-CD70 antibody described herein in methods for treating cancer (e.g., myeloid malignancies) in a subject comprising administering to the subject an effective amount of an anti-CD70 antibody described herein. In some embodiments, the cancer is MDS. In some embodiments, the cancer is AML. In some embodiments the cancer is a relapsed or refractory cancer. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-CD70 antibody is a first medicament, and which article or kit further comprises instructions on the label or package insert for treating the subject with the second medicament, in an effective amount. In some embodiments, the label or package insert indicates that the first and second medicaments are to be administered sequentially or simultaneously.

In some embodiments, the anti-CD70 antibody described herein is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Evaluation of SEA-CD70 Binding to Fcγ Receptors

In vivo, monocytes, macrophages, neutrophils, dendritic cells, and NK cells can mediate ADCP (antibody-dependent cell-mediated phagocytosis) and ADCC (antibody-dependent cell-mediated cytoxicity via FcγRI, FcγRIIa, and FcγRIIIa. While all three receptors can participate in ADCP, FcγRIIIa is believed to be the predominant Fcy receptor involved in ADCC. Nonfucosylation of $IgG_1$ antibodies results in higher affinity binding to FcγRIIIa and b, and thus can increase ADCC and ADCP activity.

SEA-CD70 (nonfucosylated hIF6) is a humanized, non-fucosylated monoclonal antibody targeting CD70, being developed by Seattle Genetics for patients with refractory and/or relapsed acute myeloid leukemia (AML) or myelodysplastic syndrome (MDS), for which no current standard of care exists. SEA-CD70 is a humanized monoclonal IgG1 antibody which binds CD70. SEA-CD70 is a nonfucosylated antibody that binds with higher affinity to FcγRIIIa than the fucosylated parent antibody SGN-70 (hIF6) and elicits increased targeted killing of CD70 positive cells via CDC, ADCP, and amplified ADCC.

Biolayer interferometry (BLI) was used to assess the binding kinetics of SGN-70 and SEA-CD70 to FcγR I, IIa, IIIa, IIb, and FcRN. FIG. 1 shows sensograms of SGN-70 (labeled as h1F6 WT) and SEA-70 (labeled as h1F6 SEA) binding to FcγRI, IIa, IIIa, IIb, and FcRN.

SGN-70 and SEA-CD70 binding kinetics with human FcγRI, FcγRIIa H131, FcγRIIa R131, FcγRIIIa F158, and FcγRIIIa V158 were assessed by BLI. Parameters are listed Table 1. Biotinylated avi-tagged human FcγR-monomeric Fc N297A LALA-PG and Fc receptor neonatal (FcRN) monomeric Fc N297A IHH fusion proteins (designed and expressed at Seattle Genetics) were loaded onto high precision streptavidin biosensors (ForteBio) to responses between 0.3 to 1 nm following a 100 second sensor check in Buffer A (0.1% bovine serum albumin [BSA], 0.02% Tween20, 1× phosphate-buffered saline [PBS] pH 7.4). After another baseline measurement, titrated antibodies were associated for 600, 10, 100, 50, and 10 seconds and dissociated for 1000, 50, 100, 500, and 50 seconds in Buffer B (1% casein, 0.2% Tween20, 1×PBS pH 7.4) for FcγRI, IIa, IIIa, FcRN pH 6, and FcRN pH 7.4, respectively. Prior to analysis, the references were subtracted in each assay. All the sensorgrams were processed with a Y-axis alignment at the start of association and an inter-step dissociation correction. A 1:1 Langmuir isotherm global fit model was used to fit the curves.

TABLE 1

Parameters for BLI Binding Protocol for SGN-70 and SEA-CD70

| Biosensor: | | SAX | |
|---|---|---|---|
| Probes (immobilized): | hCD64 P2 mFc.67 N297A LALA-PG avi E143815 | (40 µg/mL, 750 s load) | Fitting association 600 s. Dissociation 1000 s. |
| | hFcgR 2a H131 mFc.67 N297A LALAPG avi biotin E142954 | (4 µg/mL, 400 s load) | Fitting association 10 s. Dissociation 3 s. |
| | hFcgR 2a R131 mFc.67 N297A LALAPG avi biotin E142954 | (4 µg/mL, 400 s load) | Fitting association 10 s. Dissociation 3 s. |
| | hFcgR 2b mFc.67 N297A LALAPG avi biotin E142954 | (1 µg/mL), 400 s load) | Fitting association 10 s. Dissociation 10 s. |
| | hFcgR 3a F158 mFc.67 N297A LALAPG avi biotin E142954 | (2 µg/mL, 400 s load) | Fitting association 100 s. Dissociation 20 s. |
| | hFcgR 3a V158 mFc.67 N297A LALAPG avi biotin E142954 | (2 µg/mL, 400 s load) | Fitting association 100 s. Dissociation 10 s. |
| | hFcRN mFc.67 N297A IHH avi biotin E143815-01 | (5 µg/mL, 400 s load) | Fitting association 50 s. Dissociation 50 s for pH 6 (10 s & 3-4 s for pH 7.4) |
| Analyte (titrated): | h1F6 WT | E133368-02 | |
| | h1F6 SEA | E133368-01 | |
| Immobilizing buffer: | 0.1% BSA; 0.02% Tween20; 1× PBS pH 7.4 | | |
| Kinetic buffer: | 1% Casein; 0.2% Tween20; 1× PBS pH 7.4 (hFcγR's); 1% BSA, 0.2% Tween20, phosphate-citrate buffer pH 6.09 (hFcRN pH 6), phosphate-citrate buffer pH 7.46 (hFcRN pH 7.4) | | |
| Fitting parameters: | Global (group, full) 1:1; Rmax sensor unlinked | (reference subtracted prior to analysis) | |

BLI = biolayer interferometry; BSA = bovine serum albumin; FcRN = Fc receptor neonatal; PBS = phosphate-buffered saline; s = seconds.

Human CD70 affinities were determined by BLI using the parameters recited in Table 2. Baseline measurements in Buffer A (0.1% BSA, 0.02% Tween20, 1×PBS pH 7.4) were taken before and after immobilization of the antibodies at 6 µg/mL for 57 seconds with AHC (anti-Fc) biosensors purchased from ForteBio. After a second baseline was taken in Buffer B (1% casein, 0.2% Tween20, 1×PBS pH 7.4), the titrated hCD70 analyte was associated for 600 seconds and dissociated for 1000 seconds in Buffer B. The hCD70 antigen was purchased from R&D (Cat. No. 9328-CL, Lot No. DGSR0217071) and biotinylated using a 1.5-fold molar excess of EZ-Link N-hydroxysuccinimidobiotin purchased from Thermo Fisher Scientific (Cat. No. 20217, Lot No. SI249775).

TABLE 2

Parameters for BLI Binding Protocol for Human CD70

| Biosensor: | ACH (anti-Fc) | | |
|---|---|---|---|
| Probes (immobilized): | hCD70 Biotin E131664-01 | (6 μg/mL, 57 s load) | Fitting association 600 s. Dissociation 1000 s. |
| Analyte (titrated): | h1F6 WT | E133368-03 | 33.3, 11.1, 3.7, 1.2, 0.4, 0.1 nM |
|  | h1F6 SEA | E133368-01 | 33.3, 11.1, 3.7, 1.2, 0.4, 0.1 nM |
| Immobilizing buffer: | 0.1% BSA; 0.02% Tween20; 1× PBS pH 7.4 | | |
| Kinetic buffer: | 1% Casein; 0.2% Tween20; 1× PBS pH 7.4 | | |
| Fitting parameters: | Global (group, full) 1:1; Rmax sensor unlinked | (reference subtracted prior to analysis) | |

BSA = bovine serum albumin; PBS = phosphate-buffered saline; s = seconds.

SEA-CD70 and SGN-70 have similar on and off rate binding to hFcγRI and IIa. However, SEA-CD70 exhibited much higher binding affinity to FcγRIIIA than SGN-70. The BLI experiment was conducted to look at the on and off rate for SEA-CD70 and SGN-70 and binding affinity to FcγRI, FcγRIIa (H/H high affinity and R/R low affinity alleles), and FcγRIIIa (F/F low affinity and V/V high affinity alleles). Binding kinetics to FcRn was also performed and SEA-CD70 and SGN-70 were found to bind with similar kinetics and affinities.

Biolayer interferometry (BLI) was used to assess the binding kinetics of SGN-70 and SEA-CD70 to the high affinity FcγRIIIa (158V) receptor variant (Table 3). The nonfucosylated backbone of SEA-CD70 exhibited an 8-fold increase in binding affinity for the FcγRIIIa (158V) receptor. Biotinylated avi-tagged human FcγR-monomeric Fc N297A LALA-PG and FcRN monomeric Fc N297A IHH fusion proteins (designed and expressed at Seattle Genetics) were loaded onto high precision streptavidin biosensors (ForteBio) to responses between 0.3 and 1 nm following a 200 to 300 second sensor check in Buffer A (0.1% BSA, 0.02% Tween20, 1×PBS pH 7.4). After a second baseline, titrated SEA-CD70 or SGN-70 antibodies were associated until the top concentrated reached equilibrium and dissociated until the response was close to baseline. Prior to analysis, the references were subtracted in each assay. All the sensograms were processed with a Y-axis alignment at the start of association and an inter-step dissociation correction. A 1:1 Langmuir isotherm global fit model was used to fit the curves.

Figure 2B:
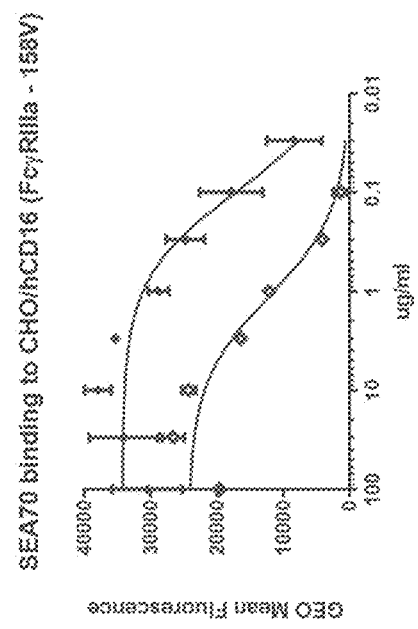

Example 2: SGN-70 and SEA-CD70 Binding to hFcγRIIIa and cFcγRIIIa by Flow Cytometry While BLI methodology is used to assess receptor affinity by monitoring binding kinetics, it is primarily set to monitor monovalent binding. To add to BLI data sets, flow cytometry was also performed (FIGS. 2A and 2B). CHO cells were transformed to overexpress the high affinity human FcγRIIIa receptor (158V) (FIG. 2A) or cynomolgus FcγRIIIa receptor (FIG. 2B) and binding of the nonfucosylated antibody SEA-CD70 (labeled as SEA-70) or the parent fucosylated antibody SGN-70 was performed. As observed in the BLI experiments, the nonfucosylated antibody SEA-CD70 bound with higher affinity than SGN-70 to both the human and cynomolgus FcγRIIIa.

The CHO-FcγRIIIa binding assay was conducted as follows:

1. Thaw cells: Cells were thawed on 11 Jun. 2019, and cultured in culture medium for 1 week to recover from freeze-thaw.

| Data Vi-CELL XR2.04, Beckman Coulter, Inc. | | | | | |
|---|---|---|---|---|---|
| Sample ID | Dilution factor | Sample date | Viable cells | Viable cells/mL (×10$^6$) | Average diameter (microns) |
| CHO-FcγRIIIa | 1.0 | 20 Jun. 2019, 12:17:42 PM | 1584 | 1.81 | 18.17 |
| CHO-cynoFcγIII | 1.0 | 20 Jun. 2019, 12:18:57 PM | 1241 | 1.42 | 15.30 |

TABLE 3

Kinetic Parameters of SGN-70 and SEA-CD70 FcγRIIIa Binding by BLI

| | Antibody | $K_D$ (M) | $k_{on}$ (1/Ms) | $k_{off}$ (1/s) | $X^2$ | $K_D$ error | $k_{on}$ error | $k_{off}$ error |
|---|---|---|---|---|---|---|---|---|
| hFcγRIII a V158 | SGN-70 | $8.60 \times 10^{-7}$ | $4.6 \times 10^4$ | $4.0 \times 10^{-2}$ | 1.3 | $1.73 \times 10^{-8}$ | $8.00 \times 10^2$ | $3.93 \times 10^{-4}$ |
| | SEA-CD70 | $1.10 \times 10^{-7}$ | $2.1 \times 10^5$ | $2.2 \times 10^{-2}$ | 0.4 | $9.69 \times 10^{-10}$ | $1.68 \times 10^3$ | $1.02 \times 10^{-4}$ |

$K_D$ = equilibrium dissociation constant; $k_{off}$ = off-rate constant; $k_{on}$ = on-rate constant.

2. Wash: 60 million cells were washed 1× in PBS in 50-mL tubes. Cells were counted again and resuspended at 2.2×10⁶/mL. Then 0.1 mL was pipetted per well
3. Make 10× dilutions of antibody: The 10× dilutions were prepared (3 mg/mL, 1 mg/mL, 0.3 mg/mL, 0.1 mg/mL, 0.03 mg/mL, 0.01 mg/mL, 0.003 mg/mL, 0.001 mg/mL, and 0.0003 mg/mL in the dilution plate).

| Antibody | Lot No. | Concentration (mg/mL) | 15 wells (3 × 5) with 330 μL of 3000 μg/mL | Volume buffer (PBS) | 15 wells (3 × 5) with 330 μL of 1000 μg/mL | Volume buffer (PBS) |
|---|---|---|---|---|---|---|
| SGN-70 | GZG002 | 25 | 0.040 | 0.290 | 0.013 | 0.317 |
| SEA-CD70 | 145567 | 25 | 0.040 | 0.290 | 0.013 | 0.317 |
| SGN-h00 | E12057-01 | 10.4 | 0.095 | 0.235 | 0.032 | 0.298 |
| SEA-h00 | 1913-020A | 10 | 0.099 | 0.231 | 0.033 | 0.297 |

PBS = phosphate-buffered saline.

4. Aspirate: Wash was aspirated in wells and 100 μL of the corresponding antibody dilutions was pipetted with a multichannel pipet. The corresponding concentrations were 300, 100, 30, 10, 3, 1, 0.03, 0.01, 0.003, 0.001, and 0.0003 μg/mL in triplicate. The concentrations were decreased vertically down the 96-well round bottom plate.
5. Vortex: After tapping hard on each side of plates, a vortexer was used to lightly mix. The plate was then incubated at 4° C. for 1 hour.
6. Centrifuge: The cells were centrifuged, aspirated, and washed in 200 μL of 1× BD stain buffer per well. Cells were resuspended by vortexing the plate on a vortexer after aspiration of the last wash.
7. Prepare antibody: Anti-human IgG-PE (Jackson, Cat. No. 109-116-170) was prepared by diluting 1 mg/mL concentrate 1:50 to yield 33 μg/mL saturating concentration. The antibody mixture was mixed well by tapping the sides of the plate. The mixture was incubated for 30 minutes in the dark in the refrigerator (4° C.).
8. Wash: The mixture was centrifuged. The supernatant was then aspirated. Each well was washed with 200 μL of 2× BD Stain buffer.
9. Analyze samples: Samples were analyzed by flow cytometry in high throughput sampler (HTS) mode on the Attune. Median fluorescence intensity (MFI) was graphed (geomean), and equilibrium dissociation constant ($K_D$) for each was calculated in PRIZM Example 3: ADCC of SEA-CD70 and SGN-70 in AML CD70+ Cells Although SGN-70 does not directly induce apoptosis in CD70 positive target cells, SEA-CD70 does mediate effector functions that potentially result in the elimination of target positive cells. In standard ADCC assays using PBMC as a source of natural killer (NK) cells, SEA-CD70 induced lysis of two CD70 positive AML cell lines in a dose-dependent fashion, while no lysis was achieved with nonbinding control human IgG. These experiments demonstrated that that SEA-CD70 has antibody dependent cellular cytotoxicity activity which is higher than SGN-CD70 antibody.

ADCC activity was evaluated using two CD70+AML cell lines as an ADCC target (FIGS. 3A and 3B). The AML cell lines, MOLM-13 (FIG. 3A) and NOMO-1 (FIG. 3B), were labeled and mixed with titrations of test antibodies or isotype control. Effector cells were isolated from cryopreserved normal donor PBMC using the EasySep Human NK Cell Enrichment Kit (Stem Cell Technologies). Effector cells were added at an effector-to-target cell ratio of 10:1 with 25,000:250,000. After a 4-h incubation, the percent specific cell lysis was calculated.

AML cell lines were grown in appropriate growth medium while incubating at 37° C. in 5% $CO_2$. Suspended cells were counted using ViCell XR cell counter. The required volume of cells was mixed with fresh growth medium and plated at seeding densities of 0.5 M/mL.

The following protocol was used to assess ADCC activity:
1. Two vials of huPBMCs were thawed in the 37° C. waterbath and resuspended in 1% FBS-RPMI media. Cells were spun down and then NK cells were isolated using the EasySep human NK cell enrichment kit following the manufacturer's protocol.
2. Antibody titrations were made using SGN-70 and SEA-CD70 antibodies with starting concentration of 2 μg/mL (working concentration 6 μg/mL) and diluted from 10× to 20 pg/mL in 1% FBS-RPMI media.
3. Target tumor cells (MOLM-3 or NOMO-1) were plated at 50 μL/well in 1% FBS-RPMI into 96 well round bottom plate. Then, antibody dilutions and isotype control were plated at 50 μL/well into the same plate. Then, isolated NK effector cells were plated at 50 μL/well at 1:10 ratio of Tumor:NK cells in 1% FBS-RPMI media into the same 96-well round bottom plate.
4. Control wells were added and brought up to 150 μL total volume with media.
5. The test plate was incubated for 4 hours at 37° C. in an incubator with 5% $CO_2$. When there was 45 minutes left of the incubation, 15 μL/well of Lysis Solution was added to Max Lysis control wells and put back into incubator for the remainder of the 4-hour incubation.
6. Test plate was spun down for 4 min at 250×g in the centrifuge and 50 μL of supernatant from each well was transferred into a new flat bottom clear plate.
7. CytoTox 96 Reagents was added at 50 μL/well and incubated for 30 min at room temperature in the dark. Then, Stop Solution was added 50 μL/well to all wells.
8. Absorbance per well was measured using the SpectraMax 190 plate reader at 490 nm and the acquired values were converted to text file and exported to Excel and into GraphPad Prism for further data analysis.
9. Cytotoxicity is reported with background subtraction and as percent of maximum lysis achieved by Lysis Solution treatment.

Example 4: SGN-70 and SEA-CD70 Impact on Regulatory T Cells

Figure 4A:
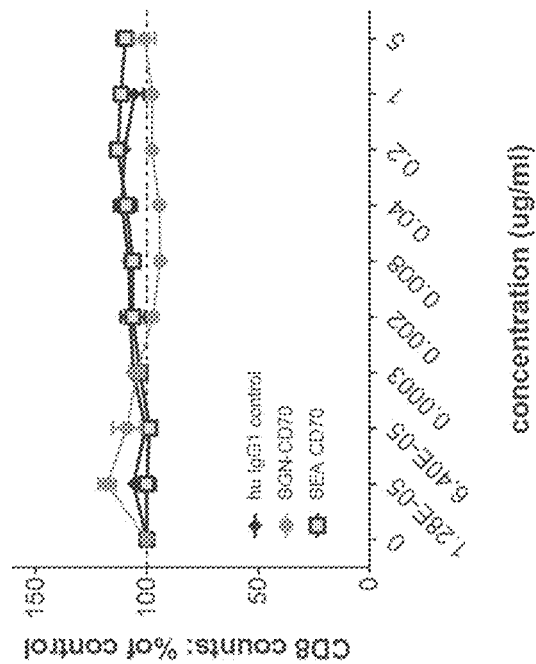
FIG. 4A-4D is a series of graphs assessing the impact of SGN-70 (labeled as SGN-CD70 in FIGS. 4A-4D) and SEA-CD70 on CD70+ Tregs and CD8 T cells in cells from donors homozygous for high affinity FcγRIIIa receptor (V/V 158) or homozygous for low affinity FcγRIIIa receptor (F/F 158).
Figure 4B:
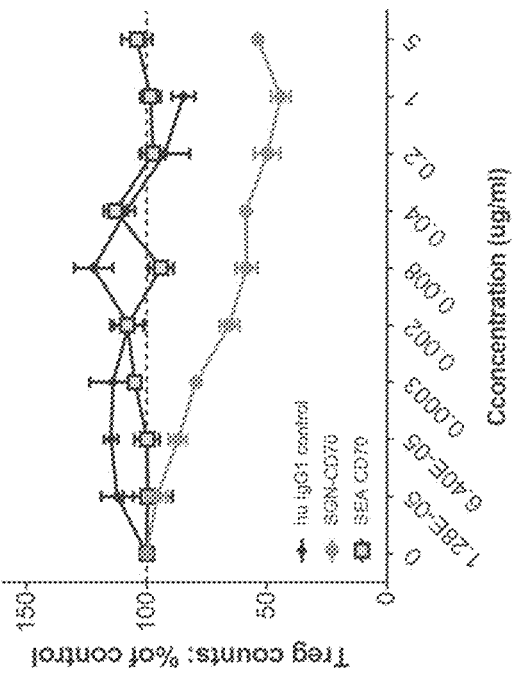
Figure 4C:
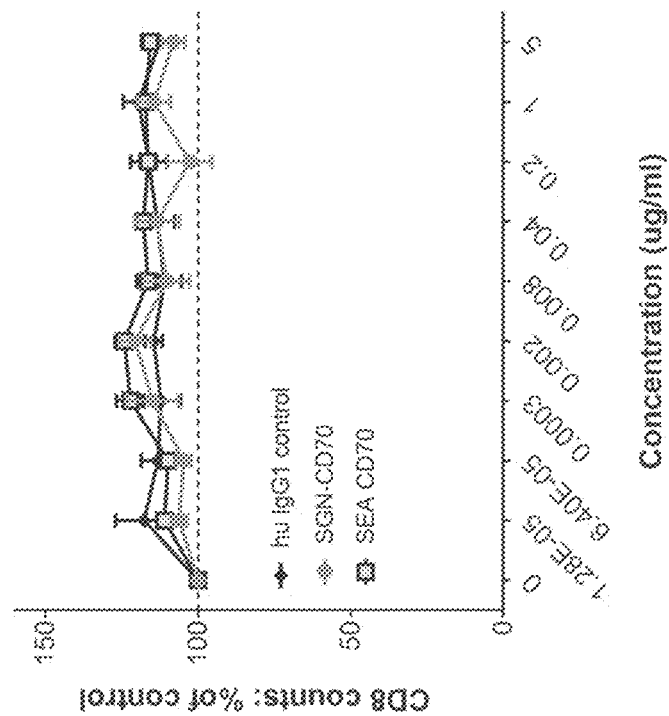
Figure 4D:
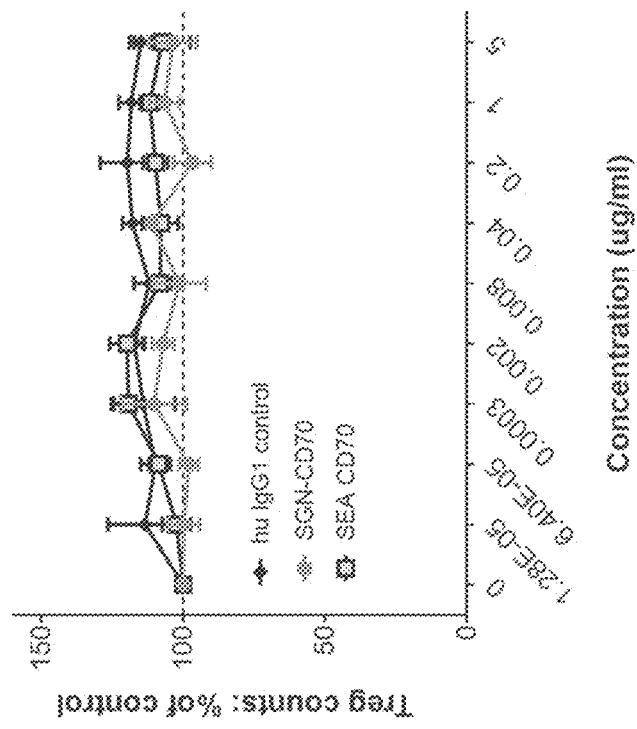
Figure 4F:
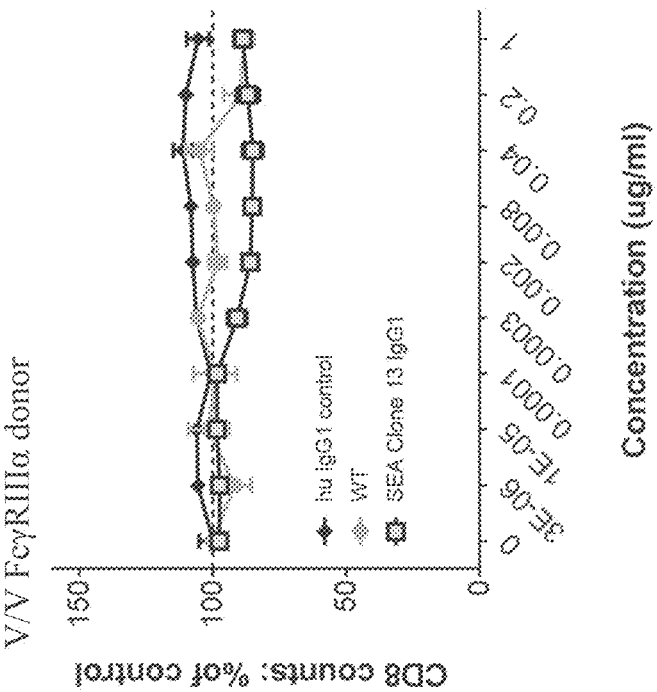
Figure 4E:
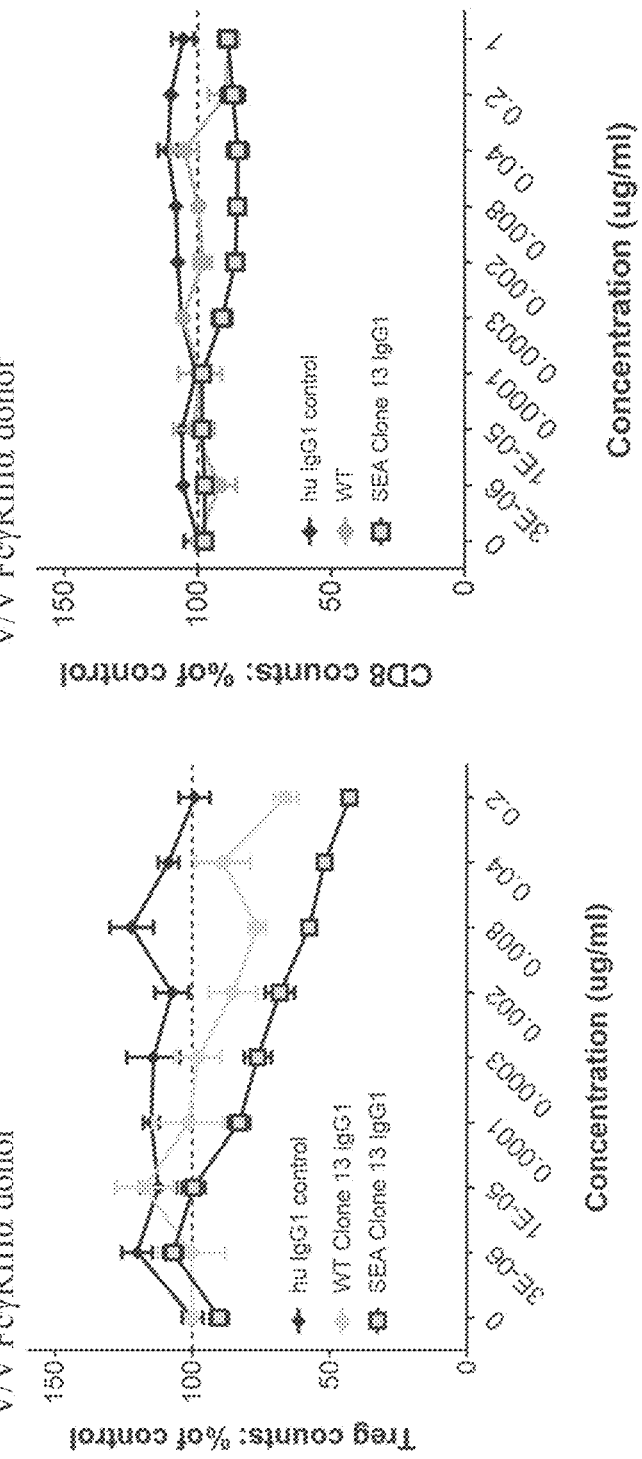

To evaluate the effect of SEA-CD70 on depletion of CD70+ T cells, PBMCs containing naïve, memory, and Treg subsets were treated with increasing concentrations of SGN-70 or SEA-CD70 for 24 hours. At the end of the experiment cells were stained with Zombie Aqua Viability Dye and total viable Treg naïve and memory CD4 and CD8 T cell numbers were assessed. Depletion assessment was performed with a donor homozygous for the low affinity FcγRIIIa receptor (F/F 158) (FIGS. 4C and 4D) or homozygous for the high affinity FcγRIIIa receptor (V/V 158) (FIGS. 4A and 4B). Fucosylated (WT Clone 13 IgG1) and nonfucosylated (SEA Clone 13 IgG1) antibodies targeting TIGIT were used as positive controls (FIG. 4E-4H). Neither CD70 targeting antibody induced T regulatory cell depletion in the low affinity F/F 158 donor (FIG. 4C). The fucosylated anti-CD70 antibody (labeled as SGN-CD70) resulted in T regulatory cell depletion when a V/V high affinity donor was used, however, surprisingly, the nonfucosylated antibody SEA-CD70, while having increased ADCC activity on CD70+ AML cell lines, did not induce Treg cell depletion (FIG. 4A). Neither fucosylated nor nonfucosylated anti-CD70 antibodies depleted CD8+ cells, whether a V/V high affinity donor (FIG. 4B) or a low affinity donor (FIG. 4D) was used.

In contrast to what was observed for the CD70 targeting antibodies, nonfucosylated anti-TIGIT antibody (labeled as SEA Clone 13 IgG1) depleted Treg cells to a greater extent than fucosylated anti-TIGIT antibody (labeled as WT Clone 13 IgG1) when either a V/V high affinity donor (FIG. 4E) or a low affinity donor (FIG. 4G) was used.

The lack of depletion of Tregs by SEA-CD70 compared to SGN-70 is surprising not only in view of the results comparing fucosylated and nonfucosylated anti-TIGIT antibodies, but also in view of publications reporting the activity of other nonfucosylated antibodies. For example, US 2019/0284287 demonstrates that a nonfucosylated anti-CD25 antibody has greater ADCC activity resulting in greater lysis and depletion of induced Tregs (iTregs) than the corresponding fucosylated anti-CD25 antibody. Similarly, U.S. Pat. No. 10,196,445 demonstrates that a nonfucosylated anti-CTLA4 antibody results in lysis and depletion of Tregs, while the corresponding fucosylated anti-CTLA4 antibody does not.

It has been shown that depletion of Tregs can have negative, and even potentially fatal, consequences. For example, it has been demonstrated that depleting Tregs using diphtheria toxin leads to severe autoimmune disorders in two mouse models. See Kim et al. (2009) *J. Immunol.* 183:7631-7634. Furthermore, acute ablation of the Treg cell population can result in terminal autoimmune disease. See Kim et al. (2007) *Nat. Immunol.* 8(2):191-7.

Example 5: A Phase I Clinical Study of SEA-CD70 in Patients with Myeloid Malignancies This is a phase 1, open-label, multicenter, dose-escalation, and cohort expansion study designed to evaluate the safety, tolerability, pharmacokinetics (PK), and antitumor activity of SEA-CD70 in adults with myeloid malignancies. The safety and efficacy of SEA-CD70 in patients with myeloid malignancies, such as myelodysplastic syndrome (MDS) and acute myeloid leukemia (AML) are evaluated herein. This trial evaluates what side effects occur and whether SEA-CD70 is an effective treatment for MDS and AML.

The study has three parts with a total enrollment of 60 subjects. Part A is a dose escalation cohort designed to identify the maximum tolerated dose (MTD) or recommended expansion dose of SEA-CD70 monotherapy in subjects with relapsed/refractory MDS, such as after failing treatment with hypomethylating agents (HMA-failure). Part B is an expansion cohort designed to evaluate the safety and tolerability of SEA-CD70 monotherapy in subjects with relapsed/refractory MDS, such as after HMA-failure. Part C is an expansion cohort designed to evaluate the safety and tolerability of SEA-CD70 monotherapy in subjects with relapsed/refractory AML. Subjects enrolled in the trial are 18 years and include both male and female subjects. SEA-CD70 will be administered on Days 1 and 15 of each treatment cycle. All treatment components are administered intravenously. Inclusion criteria and exclusion criteria for subjects enrolled in the trial are shown in Table 4.

TABLE 4

List of inclusion and exclusion criteria

| | |
|---|---|
| Inclusion Criteria | Part A Inclusion Criteria |
| | Subjects with cytologically/histologically confirmed myelodysplastic syndrome (MDS) according to the World Health Organization (WHO) classification with the following:<br>5%-20% bone marrow blasts.<br>MDS that is relapsed or refractory and must not have other therapeutic options known to provide clinical benefit in MDS available.<br>Treatment failure after prior hypomethylating agent (HMA) therapy for MDS, defined as one of the following:<br>Progression (per 2006 International Working Group [IWG] criteria) at any time after initiation of HMA therapy.<br>Lack of response (failure to achieve complete remission [CR], partial response [PR], or hematologic improvement [HI] per 2006 IWG criteria) after at least 6 cycles of azacitidine or 4 cycles of decitabine.<br>Relapse after achievement of CR, PR, or HI (per 2006 IWG criteria).<br>Intolerance of HMA (Grade 3 or higher non-hematologic toxicity leading to treatment discontinuation).<br>Subjects with isolated 5q-/5q- syndrome must have progressed, failed, relapsed, or not tolerated lenalidomide in addition to HMA.<br>Must be off all treatments for MDS for ≥ 4 weeks; growth factors and transfusions are allowed before and during the study as clinically indicated<br>Eastern Cooperative Oncology Group (ECOG) performance status of 0-1 |
| | Part B Inclusion Criteria |
| | Subjects with cytologically/histologically confirmed MDS according to the WHO classification with the following:<br>5%-20% bone marrow blasts.<br>MDS that is relapsed or refractory and must not have other therapeutic options known to provide clinical benefit in MDS available.<br>Treatment failure after prior HMA therapy for MDS defined as one of the following:<br>Progression (per 2006 IWG criteria) at any time after initiation of HMA therapy.<br>Lack of response (failure to achieve CR, PR, or HI per 2006 IWG criteria) after at least 6 cycles of azacitidine or 4 cycles of decitabine.<br>Relapse after achievement of CR, PR, or HI (per 2006 IWG criteria).<br>Intolerance of HMA (Grade 3 or higher non-hematologic toxicity leading to treatment discontinuation).<br>Subjects with isolated 5q-/5q- syndrome must have progressed, failed, relapsed, or not tolerated lenalidomide in addition to HMA.<br>Must be off all treatments for MDS (including HMAs) for ≥ 4 weeks; growth factors (e.g., G-CSF, erythropoietin and thrombopoietin) and transfusions are allowed before and during the study as clinically indicated.<br>At least one cytopenia (absolute neutrophil count [ANC] < 1800/μL or platelet count < 100,000/μL or hemoglobin [Hgb] < 10g/dL). |

TABLE 4-continued

List of inclusion and exclusion criteria

ECOG Performance Status of 0-2
Part C Inclusion Criteria

Subjects with relapsed or refractory acute myeloid leukemia (AML) according to the WHO 2016 classification (except for acute promyelocytic leukemia [APL]):
Who have received either 2 or 3 previous regimens to treat active disease. Post-remission treatments, intrathecal chemotherapy, and radiotherapy are not considered previous regimens.
Who have received 1 previous regimen to treat active disease and have at least one of the following:
Age > 60 and ≤ 75 years.
Primary resistant AML (defined as failure to achieve CR after 1-2 courses of induction therapy)
First CR duration < 6 months
Adverse-risk per European LeukemiaNet (ELN) genetic risk stratification (Dohner 2017)
Secondary AML (prior history of MDS or therapy-related)
Age 18-75 years
ECOG performance status of 0-2

Exclusion Criteria
History of another malignancy within 3 years before the first dose of study drug or any evidence of residual disease from a previously diagnosed malignancy. Exceptions are malignancies with a negligible risk of metastasis or death.
History of myeloproliferative neoplasm (MPN) including chronic myelomonocytic leukemia (CMML)
Previous exposure to CD70-targeted agents
Prior allogeneic hematopoietic stem cell transplant, for any condition
Central nervous system leukemia based on imaging or documented positive cytology in cerebral spinal fluid
Any uncontrolled Grade 3 or higher viral, bacterial, or fungal infection within 14 days prior to the first dose of study treatment. Antimicrobial prophylaxis or ongoing treatment of resolving/controlled infection is permitted.
Subjects who have experienced major surgery (defined as requiring general anesthesia and hospitalization for > 24 hours) or significant traumatic injury that would place the subject at undue risk from study procedures, in the opinion of the investigator, within 14 days before the first dose of study treatment.
Positive for hepatitis B by surface antigen expression.
Active hepatitis C infection (positive by PCR or on antiviral therapy for hepatitis C within the last 6 months). Subjects who have been treated for hepatitis C infection are permitted if they have documented sustained virologic response of 12 weeks.
Known to be positive for human immunodeficiency virus (HIV)
Known active or latent tuberculosis
History of clinically significant sickle cell anemia, autoimmune hemolytic anemia, or idiopathic thrombocytopenia purpura
History of clinically significant chronic liver disease (e.g. liver cirrhosis) and/or ongoing alcohol abuse
Documented history of a cerebral vascular event (stroke or transient ischemic attack), unstable angina, myocardial infarction, or cardiac symptoms consistent with New York Heart Association Class III-IV within 6 months prior to their first dose of SEA-CD70.
Chemotherapy, systemic radiotherapy, biologics, other anti-neoplastic or investigational agents, and/or other antitumor treatment with immunotherapy that is not completed 4 weeks prior to first dose of SEA-CD70. Focal radiotherapy that is not completed 2 weeks prior to the first dose of SEA-CD70.
Hydroxyurea or 6-mercaptopurine used for cytoreduction may be given up to 24 hours prior to treatment.
Subjects with either of the following:
A condition requiring systemic treatment with either corticosteroids (>10 mg daily prednisone or equivalent) or other immunosuppressive medications within 2 weeks of first dose of SEA-CD70
Active known or suspected clinically significant autoimmune disease or clinically significant autoimmune-related toxicity from prior immuno-oncology-based therapy
Subjects who are breastfeeding, pregnant, or planning to become pregnant from time of informed consent until 2 months (monotherapy) or 6 months (combination therapy) after final dose of study drug
Known hypersensitivity to any excipient contained in the drug formulation of SEA-CD70
Estimated life expectancy < 12 weeks Outcome measures are described in Table 5. All treatment components will be administered intravenously.

TABLE 5

Outcome measures

| Outcome measure | Time frame |
|---|---|
| Primary | |
| Number of participants with adverse events (AEs) | Through 30-37 days following last dose of SEA-CD70; up to approximately 2 years |
| Number of participants with laboratory abnormalities | Through 30-37 days following last dose of SEA-CD70; up to approximately 2 years |
| Number of participants with a dose-limiting toxicity (DLT) at each dose level (Part A only) | Though end of DLT evaluation period; up to approximately 2 weeks |
| Secondary | |
| Area under the plasma concentration-time curve | Through 30-37 days following last dose of SEA-CD70; up to approximately 2 years |
| Time maximum concentration attained | Through 30-37 days following last dose of SEA-CD70; up to approximately 2 years |
| Maximum observed plasma concentration | Through 30-37 days following last dose of SEA-CD70; up to approximately 2 years |
| Minimum plasma concentration per dosing interval | Through 30-37 days following last dose of SEA-CD70; up to approximately 2 years |
| Terminal elimination half-life | Through 30-37 days following last dose of SEA-CD70; up to approximately 2 years |
| Antidrug antibodies | Through 30-37 days following last dose of SEA-CD70; up to approximately 2 years |
| Complete remission (CR) Rate | Up to approximately 4 years |
| Complete emission with incomplete platelet recovery (CRi) rate | Up to approximately 4 years |
| Complete remission with partial hematologic recovery (CRh) rate | Up to approximately 4 years |
| Hematologic response (HI) rate | Up to approximately 4 years |
| Objective response rate (ORR) | Up to approximately 4 years |
| Blast clearance rate | Up to approximately 4 years |
| Duration of response (DOR) | Up to approximately 4 years |
| Overall survival (OS) | Up to approximately 4 years |
| Event-free survival (EFS) | Up to approximately 4 years |
| Minimal residual disease (MRD)-negative ORR | Up to approximately 4 years |
| Time to response (TTR) | Up to approximately 4 years |
| Rate of conversion to transfusion independence | Up to approximately 4 years |
| Maintenance of TI | Up to approximately 4 years |

Example 6: Dose-Dependent Effects of h1F6SEA on Survival in the Raji NHL Burkitt Lymphoma Mouse Model Studies have shown that acute myeloid leukemia (AML) and myelodysplastic disease (MDS) express CD70 and its receptor CD27. The objective of this study was to test animal survival in response to the anti-CD70 monoclonal antibody SEA-CD70 (h1F6SEA). Animal survival was assessed in response to administration of SEA-CD70 in a CD70-expressing cell xenograft mouse model, the Raji NHL-Burkitt model.

Figure 5:
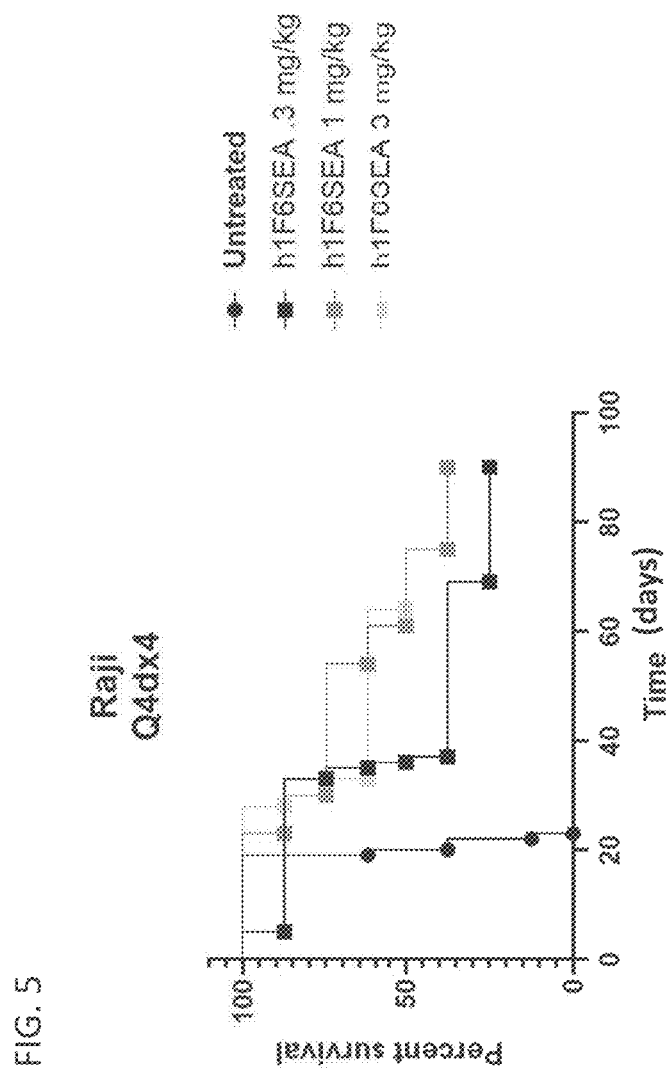
FIG. 5 is a Kaplan-Meyer graph of results assessing the impact of treatment with SEA-CD70 on percent animal survival over time in the Raji NHL Burkitt Lymphoma model. SEA-CD70 is labeled as h1F6SEA.

SCID mice were implanted with 1×10⁶ Raji cells intravenously in the tail vein on day zero. One day post-implant animals were randomized into treatment groups of eight mice per group. Animals were dosed once daily every four days for a total of 4 cycles (Q4dx4) with h1F6SEA at 0.3, 1 and 3 mg/kg on day 1 post tumor implant intraperitoneally. Stock concentration antibody was diluted to the appropriate concentration and injected into animals at 10 µl/g of body weight. Animals were then monitored for disease symptoms. Animals were followed until disease symptoms appeared and then were euthanized. Analysis of animals occurred over time and animals were sacrificed when they showed disease symptoms. Animals in the untreated group showed a median survival of 20 days while animals treated with 0.3 mg/kg h1F6SEA progressed to 36.5 days, and animals treated with either 1 or 3 mg/kg progressed to 68 and 69.5 days, post implant. The total number of animals in each group on individual days during the study is shown in Table 6. The percent survival was computed for animals across all treatment groups (FIG. 5). The Kaplan-Meyer graph shows a significant increase in percent survival between treated and untreated animals, and a dose response between 0.3 mg/kg and 1 or 3 mg/kg (FIG. 5). The percent survival was quantified across experimental days for all treatment groups including dosages of h1F6SEA of 0.3 mg/kg, 1 mg/kg and 3 mg/kg. Treatment of mice with h1F6SEA increased survival compared to that of untreated mice (FIG. 5).

TABLE 6

Kaplan-Meyer results of anti-tumor activity of h1F6SEA in the Raji NHL Burkitt Lymphoma model.

| Days | Untreated | h1F6SEA .3 mg/kg | h1F6SEA 1 mg/kg | h1F6SEA 3 mg/kg |
|---|---|---|---|---|
| 0 | 8 | 8 | 8 | 8 |
| 5 |   | 8 |   |   |
| 19 | 8 |   |   |   |
| 20 | 5 |   |   |   |
| 22 | 3 |   |   |   |
| 23 | 1 |   | 8 |   |
| 25 |   |   |   |   |
| 28 |   |   |   | 8 |
| 30 |   |   | 7 |   |
| 31 |   |   |   |   |
| 33 |   | 7 |   | 7 |
| 35 |   | 6 |   |   |
| 36 |   | 5 |   |   |
| 37 |   | 4 |   |   |
| 44 |   |   |   |   |
| 46 |   |   |   |   |
| 54 |   |   | 6 |   |
| 61 |   |   | 5 |   |
| 64 |   |   |   | 5 |
| 69 |   | 3 |   |   |
| 75 |   |   | 4 | 4 |
| 79 |   |   |   |   |
| 90 |   | 2 | 3 | 3 |

Figure 6:
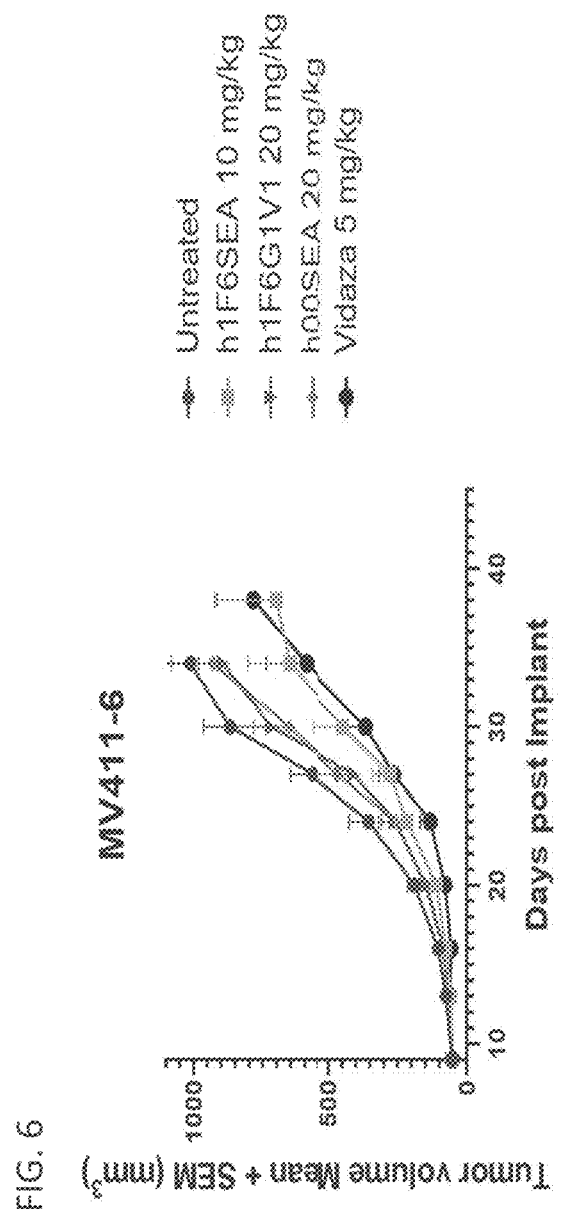
FIG. 6 is a graph assessing the anti-tumor efficacy of h1F6SEA, h1F6G1V1, hOOSEA, and azacitidine in the MV-411 acute myeloid leukemia model. SEA-CD70 is labeled as h1F6SEA. An antibody comprising the same CDRs as SEA-CD70, but comprising inactivating backbone mutations, is labeled as h1F6G1V1. An afucosylated human IgG1 isotype control antibody is labeled as hOOSEA.

Example 7. Dose-Dependent Effects of h1F6SEA on Tumor Growth in the MV411 Acute Myeloid Leukemia Mouse Model In this study, tumor growth in response to administration of the anti-CD70 antibody SEA-CD70 (h1F6SEA) was assessed in a CD70 expressing cell xenograft mouse model, the MV-411 line, an acute myeloid leukemia model. Tumor growth was reported as a volume and calculated as an average across animals within each treatment group (FIG. 6) as well as reported for each individual within each treatment group (FIG. 7A-D, Table 7). Daily tumor volumes (mm³) from individual animals within different treatment groups are summarized in Table 7.

Figure 7A:
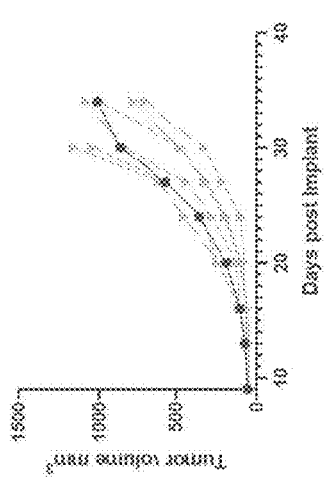
FIG. 7A-7D is a series of spider plots assessing the anti-tumor efficacy of h1F6SEA, hOOSEA (afucosylated human IgG1 isotype control antibody), h1F6G1V1 (antibody comprising the same CDRs as SEA-CD70, but comprising inactivating backbone mutations), and azacitidine in the MV-411 acute myeloid leukemia model. Tumor volumes for individual animals are plotted for each treatment condition and overlaid with the median tumor volume in the untreated group.
Figure 7B:
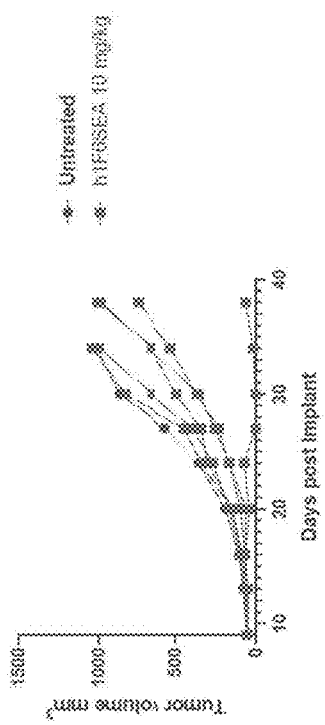
Figure 7D:
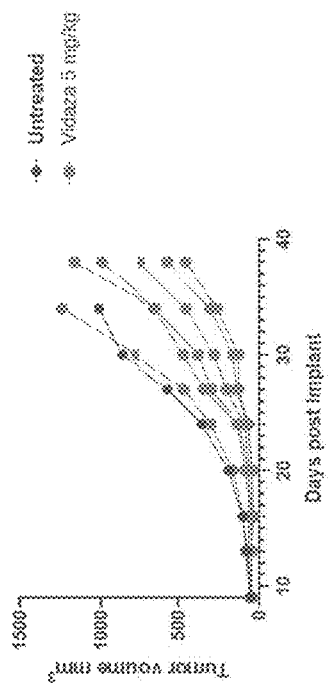
Figure 7C:
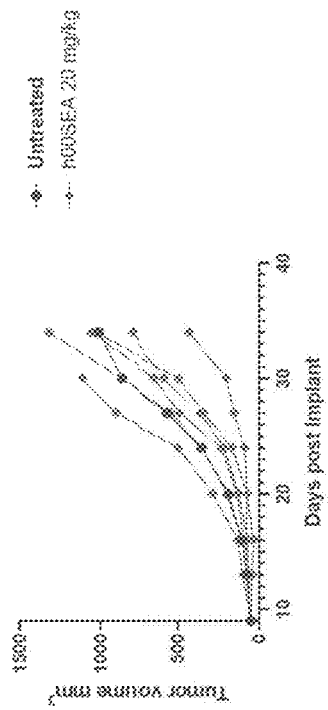

SCID mice were implanted with 5×10⁶ MV-411 cells sub-cutaneous in the flank on day 0. When mean tumor size of 50 mm³ (measured by using the formula: Volume (mm³)= 0.5*Length*Width² where the length is the longer dimension) was reached, mice were randomized into treatment groups of six mice per group. Animals were treated per treatment group; groups receiving antibody were treated every 4 days for four cycles, animals receiving azacitidine were treated every 4 days for four cycles. Treatments were given intraperitoneally. Stock concentrations of antibody and chemotherapy were diluted to the appropriate concentration and injected into animals at 10 µl/g of body weight. Tumor length and width, and animal weight were measured two times weekly throughout the study and tumor volume was calculated using the formula above. Animals were followed until tumor volume measured ~1000 mm³, at which time the animals were euthanized. Animals were dosed on various schedules based on treatment received nine days post tumor implant; animals receiving antibody were treated Q4dx4, and azacitidine-treated animals were dosed once daily every four days for a total of four cycles (Q4dx4). Analysis of tumor volume changes over time indicated a modest tumor delay as compared to animals in the untreated group or those being treated with non-binding antibodies (FIG. 6 and FIG. 7A-D). When looking at the time it took for tumors in each group to reach a 10× fold change, untreated took an average of 26.8 days while the h1F6SEA 10 mg/kg treatment group took on average 32.65, an 18% delay in tumor growth (FIG. 6, and FIG. 7A-D). This could, however, be longer as one animal never reached 10× fold change. Animals treated with azacitidine (labeled as Vidaza in FIG. 6, FIG. 7D and Table 7) also showed a growth delay taking 33.68 days to reach 10× fold change, a 20.5% delay in tumor growth (FIG. 6 and FIG. 7A-D). It should also be noted that one mouse in the h1F6SEA 10 mg/kg group showed a very robust tumor growth delay that extended the length of the study (FIG. 7A and Table 7).

TABLE 7

Anti-tumor efficacy of h1F6SEA, h1F6G1V1, h00SEA, and Vidaza in the MV-411 Acute Myeloid Leukemia model.

| Days post Implant | Untreated | | | | | | | h1F6SEA 10 mg/kg | | | | |
|---|---|---|---|---|---|---|---|---|---|---|---|---|
| 9 | 0.0 | 50.3 | 56.9 | 54.4 | 58.3 | 50.7 | 52.1 | 54.1 | 58.6 | 51.0 | 59.2 | 59.0 |
| 13 | 66.3 | 81.3 | 70.8 | 94.2 | 94.7 | 50.1 | 48.7 | 68.7 | 59.9 | 47.1 | 56.4 | 72.6 |
| 16 | 95.4 | 116.4 | 81.8 | 116.8 | 135.7 | 76.8 | 90.8 | 83.5 | 67.6 | 65.3 | 60.4 | 98.2 |
| 20 | 146.2 | 203.7 | 155.1 | 240.6 | 271.7 | 117.9 | 151.0 | 142.8 | 93.1 | 63.1 | 42.0 | 165.9 |
| 24 | 279.6 | 326.0 | 224.0 | 489.0 | 633.3 | 179.0 | 336.7 | 299.1 | 165.4 | 161.4 | 70.9 | 266.6 |
| 27 | 522.2 | 616.5 | 453.6 | 670.7 | 871.2 | 268.4 | 447.0 | 337.6 | 231.0 | 254.6 | 0.0 | 392.1 |
| 30 | 813.3 | 1012.1 | 766.1 | 1060.9 | 1090.0 | 464.8 | 831.7 | 494.8 | 365.1 | 352.6 | 0.0 | 661.5 |
| 34 | 1099.2 | | 1163.4 | | | 773.7 | 1042.3 | 655.6 | 531.6 | 666.1 | 15.4 | 998.9 |
| 38 | | | | | | | | 1005.8 | 751.7 | 988.1 | 63.1 | |
| 41 | | | | | | | | | 1024.7 | | 66.6 | |

| Days post Implant | h1F6G1V1 20 mg/kg | | | | | | | h00SEA 20 mg/kg | | | | |
|---|---|---|---|---|---|---|---|---|---|---|---|---|
| 9 | 48.0 | 62.8 | 51.3 | 49.1 | 52.1 | 58.2 | 55.5 | 60.3 | 51.0 | 52.6 | 56.3 | 50.1 |
| 13 | 46.1 | 64.4 | 65.7 | 61.5 | 56.8 | 65.4 | 65.1 | 62.5 | 101.8 | 76.4 | 72.8 | 43.4 |
| 16 | 59.3 | 109.1 | 97.7 | 68.1 | 64.7 | 103.8 | 76.7 | 94.2 | 131.0 | 106.9 | 70.0 | 34.3 |
| 20 | 91.5 | 234.8 | 241.3 | 80.6 | 104.4 | 127.2 | 73.6 | 135.4 | 287.0 | 199.5 | 126.6 | 75.5 |
| 24 | 188.7 | 449.2 | 338.1 | 96.3 | 198.9 | 274.9 | 90.9 | 234.5 | 499.1 | 349.4 | 215.2 | 165.8 |
| 27 | 306.6 | 606.7 | 567.6 | 213.6 | 325.4 | 433.0 | 154.9 | 490.1 | 905.1 | 544.0 | 364.4 | 344.4 |
| 30 | 474.6 | 1156.6 | 1039.1 | 325.4 | 470.6 | 847.7 | 202.6 | 649.0 | 1112.9 | 872.9 | 589.5 | 497.7 |
| 34 | 782.9 | | | 709.0 | 1001.0 | 1081.8 | 432.6 | 1062.8 | | 1321.2 | 801.4 | 1034.7 |
| 38 | 1269.5 | | | 1330.9 | | | 696.2 | | | | 1203.9 | |
| 41 | | | | | | | 1109.2 | | | | | |

| Days post Implant | Vidaza 5 mg/kg | | | | | |
|---|---|---|---|---|---|---|
| 9 | 45.0 | 50.0 | 49.9 | 57.6 | 59.5 | 55.2 |
| 13 | 47.9 | 47.5 | 73.3 | 50.9 | 84.1 | 65.6 |
| 16 | 35.9 | 42.5 | 48.9 | 47.2 | 99.2 | 70.8 |
| 20 | 45.2 | 47.1 | 86.6 | 69.9 | 162.6 | 63.4 |
| 24 | 74.2 | 66.4 | 136.7 | 125.0 | 301.0 | 92.0 |
| 27 | 141.5 | 129.0 | 344.5 | 295.9 | 465.4 | 202.5 |
| 30 | 161.8 | 130.7 | 469.6 | 379.5 | 778.9 | 279.0 |
| 34 | 303.9 | 260.2 | 649.8 | 640.9 | 1238.8 | 451.9 |
| 38 | 568.7 | 452.8 | 1164.6 | 993.8 | | 740.5 |
| 41 | 978.2 | 688.1 | | | | 1063.7 |

Figure 8B:
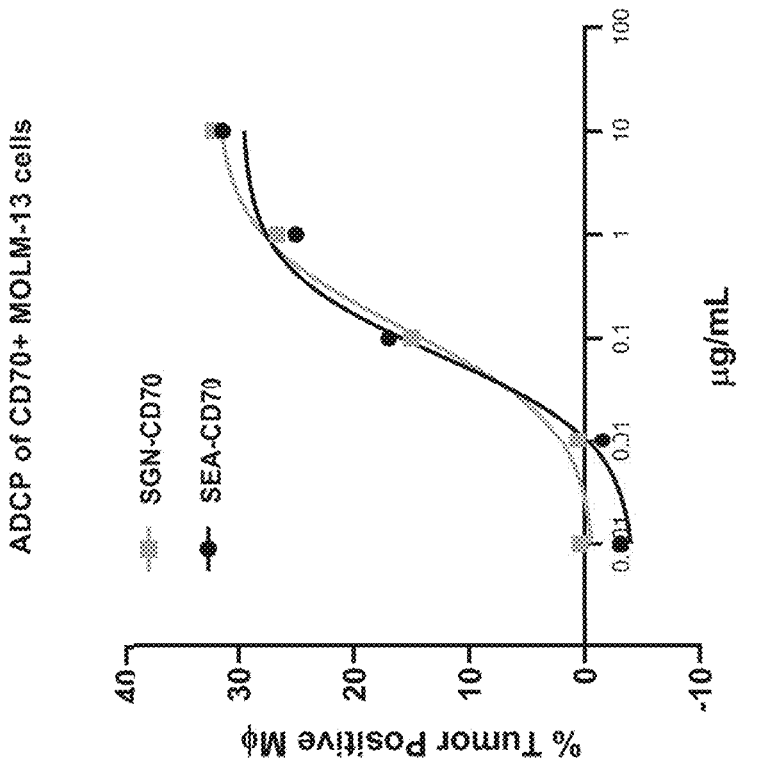
FIG. 8A-8B is a series of graphs evaluating SEA-CD70 and SGN-CD70 mediated ADCP activity against AML cell lines. Data shown represents the percent positive macrophages over background control.
Figure 8A:
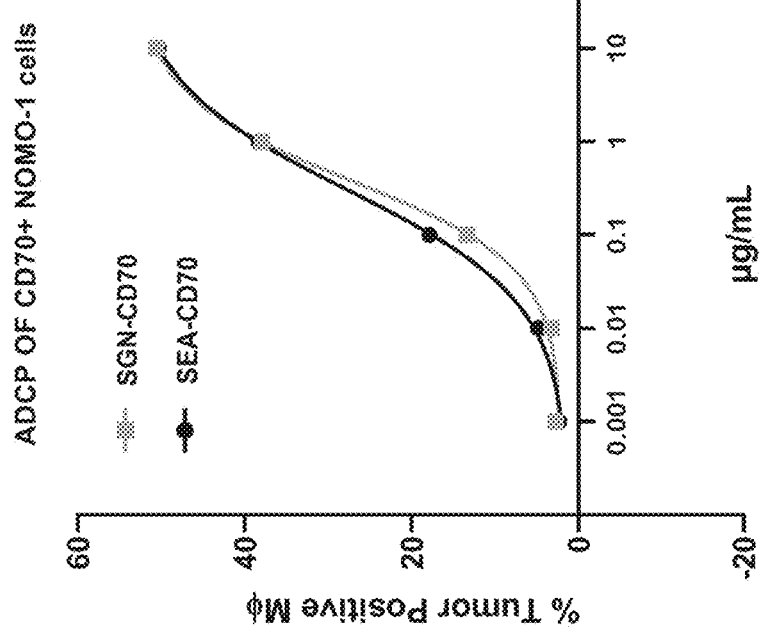

Example 8. Evaluation of SEA-CD70 and SGN-CD70 Mediated ADCP Activity Against AML Cell Lines SEA-CD70 and SGN-CD70 (also referred to as SGN-70) mediated ADCP were determined using CD70+ target cells (NOMO-1 and MOLM-13) loaded with a lipophilic fluorescent dye and mixed with monocyte-derived macrophages overnight. Phagocytosis of fluorescently labeled target cells was determined by flow cytometry. Phagocytosis was measured for the appearance of double-labeled coincident events (fluorescent target cells) and anti-CD11c positivity to identify monocyte/macrophages. Macrophages readily phagocytosed target cells coated with either SEA-CD70 or SGN-CD70 in an antibody dose-dependent manner (FIG. 8A and FIG. 8B). SEA-CD70 and SGN-CD70 mediated phagocytosis to similar levels.

The following protocol was used to assess ADCC activity on AML cell lines:
1. Target cells were labeled using the PKH26 Red Fluorescent Cell Linker Mini Kit (Sigma Aldrich) and following the manufacturer's instructions.
2. Cells (4000 cells/well) were incubated with the indicated test articles for 30 minutes, washed and resuspended in RPMI plus 10% ultra-low IgG FBS.
3. PBMC-derived macrophages (100,000 cells/well), generated by incubating PBMC-derived monocytes with 500 U/mL (50 ng/mL) GM-CSF for 10-12 days, were added to the target cells and incubated at 37° C. for 2 hours.
4. Plates were centrifuged and cells resuspended in 100 µl of APC-CD11 antibody (macrophage marker) and incubated on ice for 30 minutes.
5. Cells were washed, resuspended in PBS and analyzed by flow cytometry to determine the percentage of phagocytosis

Figure 9A:
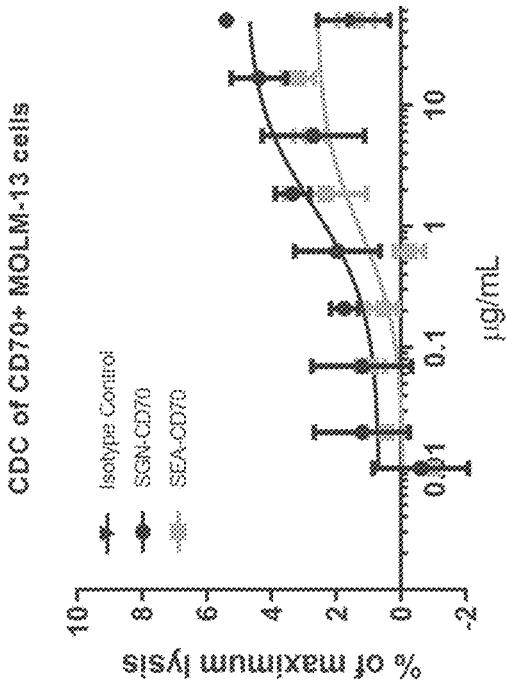
FIG. 9A-9B is a series of graphs evaluating SEA-CD70 and SGN-CD70 CDC mediated CDC activity against AML cell lines.
Figure 9B:
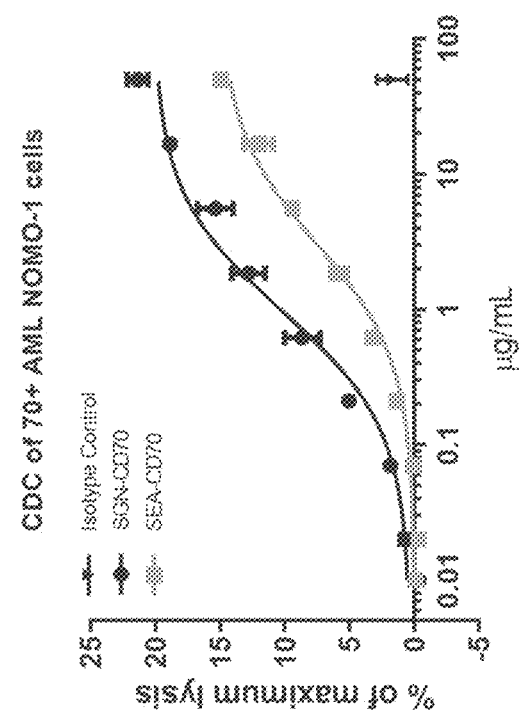

Example 9. Evaluation of SEA-CD70 and SGN-CD70 Mediated CDC Activity Against AML Cell Lines SEA-CD70 and SGN-CD70 were further tested for their ability to induce cell lysis by complement fixation. AML cell lines positive for CD70 were fluorescently labeled and treated with increasing concentrations of CD70 directed antibodies. Cells were then exposed to human compliment and lysis determined as release of fluorescent dye. The CD70+AML cell lines MOLM-13 and NOMO-1 were lysed in an antibody-specific, dose-dependent manner when coated with either SEA-CD70 or SGN-CD70 in the presence of normal human serum that was not heat inactivated (FIGS. 9A and 9B).

The following protocol was used to assess CDC activity on AML cell lines:
1. Cells were incubated with 10 mg/ml anti-CRP monoclonal antibodies mix (anti-hCD46, anti-hCD55, anti-hCD59) for 30 minutes on ice.
2. Cells were washed and plated (200,000 cells/well) in media containing non-heat-inactivated serum, Sytox Green (Life technology), and antibodies, which were added at the indicated final concentration, for 2 hours at 37° C.
3. Cell dead was quantified by detecting Sitox Green fluorescent signal on an Envison plate reader (Perkin Elmer) and normalized over positive control (1% Triton X-100 treated cells).

Figure 10:
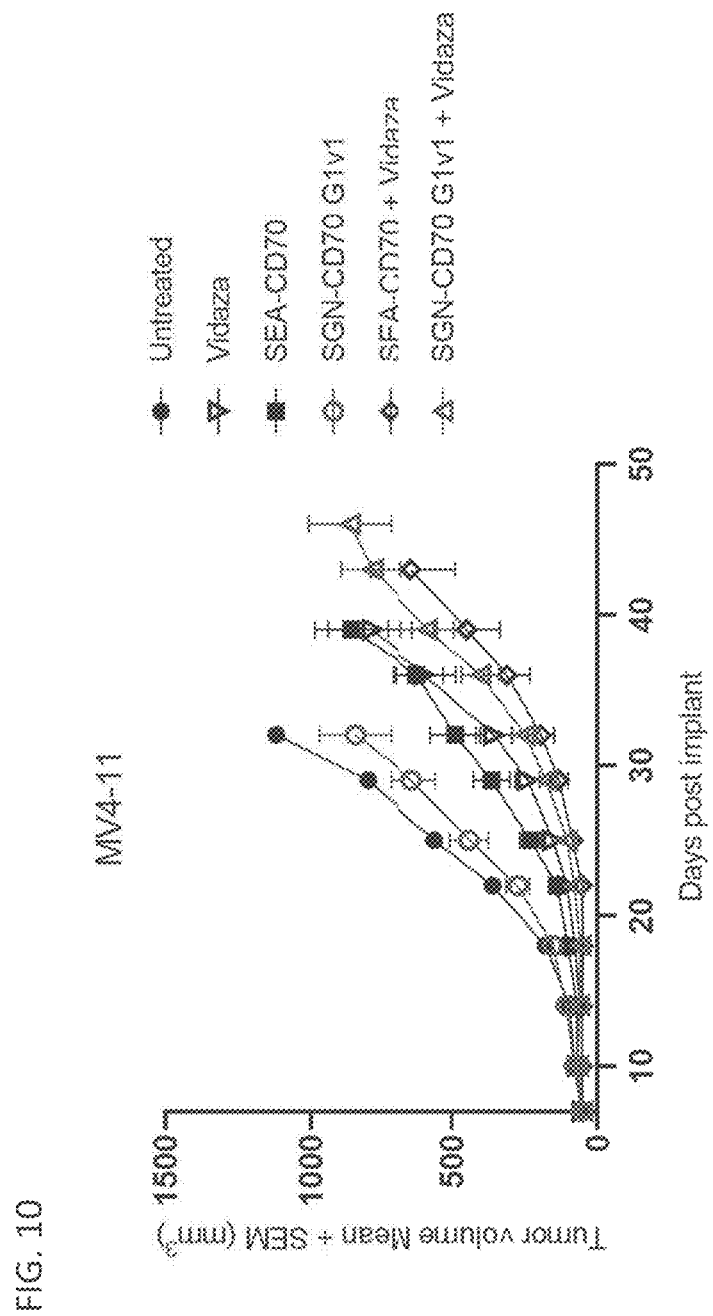
FIG. 10 is a graph evaluating the effect of SEA-CD70 in combination with azacitidine (VIDAZA®) on tumor growth in the MV411 AML xenograft mouse model. Mean tumor volume (±SEM) is reported for each treatment arm. For each treatment group, data are plotted until the first animal in each group was sacrificed for reaching a tumor size >1000 mm$^3$.

Example 10. Effect of SEA-CD70 and Azacitidine in Combination on Tumor Growth in the MV411 AML Xenograft Mouse Model In this study, tumor growth in response to administration of the afucosylated anti-CD70 antibody SEA-CD70 (h1F6SEA) alone or in combination with azacitidine (VIDAZA®) was assessed in a CD70-expressing cell xenograft mouse model MV4-11 line. Tumor growth was reported as a volume and calculated as an average across animals within each treatment group (FIG. 10). SCID mice were implanted with 5×10e6 MV4-11 cells subcutaneously in the flank on day 0. When mean tumor size of 50 mm$^3$ (measured by using the formula: Volume (mm$^3$) =0.5*Length*Width$^2$, where the length is the longer dimension) was reached, mice were randomized into treatment groups of 9 mice per group. Treatments were given intraperitoneally. Stock concentrations of antibody and chemotherapy were diluted to the appropriate concentration and injected into animals at 10 µl/g of body weight. Tumor length and width, and animal weight were measured two times weekly throughout the study and tumor volume was calculated using the formula above. Animals were followed until tumor volume measured ~1000 mm$^3$, at which time the animals were euthanized. Animals were dosed on various schedules based on treatment received; animals receiving antibodies were treated with a dose of 10 mg/kg (Q4dx5), azacitidine-treated animals were dosed once daily for five consecutive days (azacitidine 2 mg/kg; Q1dx5) for a total of 3 cycles (3 weeks), animal receiving combination of treatments received each treatment at the same dose and schedule as the single treatments. Analysis of tumor volume changes over time indicates that both azacitidine and SEA-CD70 reduce tumor growth when compared to control untreated animals. In addition, when animals were treated with a combination of SEA-CD70 and azacitidine, a further increase in tumor delay was observed compared to both untreated animals and single SEA-CD70 or azacitidine treatments (FIG. 10). As expected, treatment with SEA-CD70 G1V1 antibodies, which carry mutations in the Fc domains which reduce binding to Fcgamma receptors (E233P, L234V, L235A) (see McEarchern et al., 2008, *Clin. Cancer Res.* 14(23):7763-72; Armour et al., 1999, *Eur. J. Immunol.* 29:2613-2624) were not effective in reducing tumor growth. Surprisingly, when SEA-CD70 G1V1 was combined with azacitidine a significant delay in tumor growth was observed (FIG. 10). Without wishing to be bound by any theory, the mechanism underling such observation may be related to changes in expression of CD70 or CD27 caused by azacitidine treatment, or inhibition of CD27/CD70 signaling. When looking at the time it took for tumors in each group to reach a 10× fold change, untreated animals took an average of 17.82 days, while the SEA-CD70 treatment group took on average 25.08 days, a 31% delay in tumor growth (FIG. 10). Animals treated with azacitidine also showed a growth delay taking 26.59 days to reach a 10× fold change, a 33% delay in tumor growth compared to untreated control (FIG. 10). Animals treated with combination of azacitidine and SEA-CD70 took an average 33.81 days to reach a 10× fold increase (a 47.3% delay in tumor growth) (FIG. 10), indicating that the combination of SEA-CD70 and azacitidine effectively delays tumor growth compared to the two agents used as single agents.

Figure 11A:
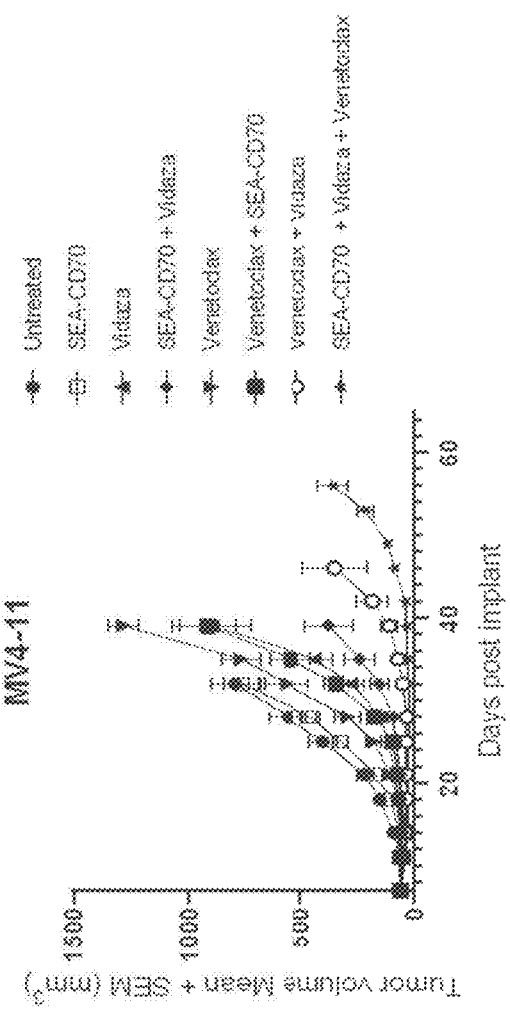
FIG. 11A-B is a series of graphs evaluating the effect of SEA-CD70 in combination with azacitidine (VIDAZA®), venetoclax (VENCLEXTA®; ABT-199), or both (azacitidine+venetoclax) on tumor growth in the MV411 AML xenograft mouse model.

Example 11. Effect of SEA-CD70 in Combination with Azacitidine, Venetoclax (ABT-199) or Both (Azacitidine+Venetoclax) on Tumor Growth in the MV4-11 AML Xenograft Mouse Model In this study, tumor growth in response to administration of the afucosylated anti-CD70 antibody SEA-CD70 (h1F6SEA) alone or in combination with azacitidine (VIDAZA®), venetoclax (VENCLEXTA®; ABT-199), or SEA-CD70+azacitidine+venetoclax (triplet combination), was assessed in a CD70-expressing cell xenograft mouse model MV4-11 line. Tumor growth was reported as a volume and calculated as an average across animals within each treatment group (FIG. 11A). Immunocompromised SCID mice were implanted with 5×10e6 MV4-11 cells subcutaneously in the flank on day 0. When mean tumor size of 50 mm$^3$ (measured by using the formula: Volume (mm$^3$) =0.5*Length*Width$^2$, where the length is the longer dimension) was reached, mice were randomized into treatment groups of 10 mice per group. Stock concentrations of antibody and chemotherapy were diluted to the appropriate concentration and injected into animals at 10 µl/g of body weight. Tumor length and width, and animal weight were measured two times weekly throughout the study and tumor volume was calculated using the formula above. Animals were followed until tumor volume measured ~1000 mm$^3$, at which time the animals were euthanized. Animals were dosed on various schedules based on treatment received; animals receiving antibody were treated with 10 mg/kg of antibody (Q4dx5), azacitidine-treated animals were dosed daily (2 mg/kg) for five consecutive days (Q1dx5) each week, for a total of 3 cycles (3 weeks); venetoclax was given at 25 mg/kg every day by oral gavage for 21 days consecutively (Q1dx21). Animal receiving combination of treatments received each treatment at the same dose and schedule as the single treatments.

As shown in FIG. 11A, SEA-CD70, azacitidine and venetoclax treatments delay tumor growth when dosed as single agents. Notably, the addition of SEA-CD70 to either azacitidine or venetoclax reduced tumor growth significantly when compared to the relative single arm treatments (p<0.05 in both comparison at day 39, two-way ANOVA). The combination of venetoclax+azacitidine also further inhibited tumor growth when compared to the single agents (p<0.01 and p<0.001 when compared to azacitidine or venetoclax single arms respectively at day 39, two-way ANOVA)

Figure 11B:
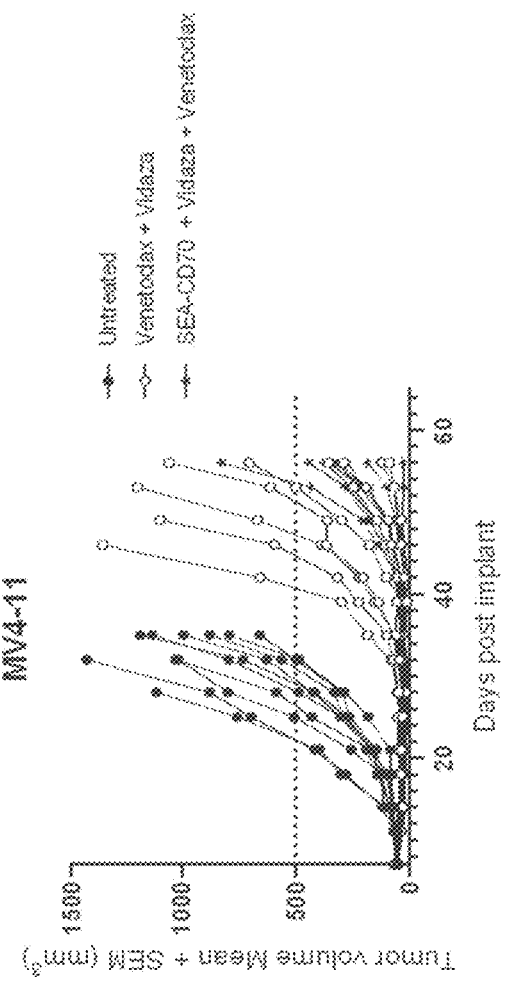

The addition of SEA-CD70 to venetoclax and azacitidine (triplet combination), further delayed tumor growth compared to the two agent combination (p=0.0594 at day 39, two-way ANOVA). At day 46, the azacitidine+venetoclax combination group had a mean tumor size of 349.9±141.7 mm$^3$ (mean±SEM) while the triplet combination had a mean tumor size of 85±11.09 mm$^3$ (mean±SEM) (p<0.05; one-tailed t-test). As shown in FIG. 11B, when observing the single animal tumor growth curves, five animals treated with a combination of venetoclax+azacitidine reached a 10× fold increase in tumor volume at day 56, while only one animal treated with the triplet combination reached the 10× threshold at the time the experiment was interrupted.

Overall these results indicate that, when added to standard of care agents (azacitidine, venetoclax, or a combination of azacitidine+venetoclax) SEA-CD70 further delayed tumor growth.

What is claimed is:

1. A method of treating a CD70-expressing cancer in a subject, the method comprising administering to the subject a therapeutically effective amount of a nonfucosylated anti-CD70 antibody, wherein the method results in a depletion of cancer cells in the subject, wherein the method does not result in a depletion of CD70+T regulatory cells (CD70+ Tregs) in the subject, wherein the anti-CD70 antibody comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, and wherein the cancer is selected from the group consisting of myelodysplastic syndrome (MDS) and acute myeloid leukemia (AML).

2. The method of claim 1, wherein the anti-CD70 antibody a heavy chain variable region comprising the amino acid sequence of SEQ ID NO:1 and a light chain variable region comprising the amino acid sequence of SEQ ID NO:2.

3. The method of claim 1, wherein the Fc domain is an antibody effector domain mediating one or more of antibody-dependent cellular cytotoxicity (ADCC), antibody-dependent cellular phagocytosis (ADCP), and complement-dependent cellular cytotoxicity (CDC).

4. The method of claim 1, wherein the anti-CD70 antibody is vorsetuzumab.

5. The method of claim 1, wherein the antibody is conjugated to a therapeutic agent.

6. The method of claim 5, wherein the therapeutic agent is a chemotherapeutic agent or an immunomodulatory agent.

7. The method of claim 6, wherein the chemotherapeutic agent is monomethyl auristatin E (MMAE) or monomethyl auristatin F (MMAF).

8. The method of claim 1, wherein the method comprises administering a population of anti-CD70 antibodies, wherein each antibody in the population of anti-CD70 antibodies comprises a heavy chain variable region comprising the three CDRs of SEQ ID NO:1, a light chain variable region comprising the three CDRs of SEQ ID NO:2, wherein the CDRs of the anti-CD70 antibody are defined by the Kabat numbering scheme, and an Fc domain, wherein at least 50% of the anti-CD70 antibodies in the population of the anti-CD70 antibodies lack core fucosylation.

9. The method of claim 8, wherein at least 90% of the anti-CD70 antibodies in the population of the anti-CD70 antibodies lack core fucosylation.

10. The method of claim 1, wherein the cancer is MDS.

11. The method of claim 10, wherein the MDS is relapsed or refractory MDS.

12. The method of claim 1, wherein the cancer is AML.

13. The method of claim 12, wherein the AML is relapsed or refractory AML.

14. The method of claim 1, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cancer cells express CD70.

15. The method of claim 1, wherein administering the nonfucosylated anti-CD70 antibody to the subject results in a depletion of cancer cells by at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or about 100% compared to the amount of cancer cells before administering the nonfucosylated anti-CD70 antibody to the subject.

16. The method of claim 1, wherein administering the nonfucosylated anti-CD70 antibody to the subject results in a depletion of CD70+Tregs of no more than about 20%, about 10%, about 9%, about 8%, about 7%, about 6%, about 5%, about 4%, about 3%, about 2%, about 1%, or about 0.1% compared to the amount of CD70+Tregs before administering the nonfucosylated anti-CD70 antibody to the subject.

17. The method of claim 1, wherein one or more therapeutic effects in the subject is improved after administration of the nonfucosylated anti-CD70 antibody relative to a baseline.

18. The method of claim 17, wherein the one or more therapeutic effects is selected from the group consisting of: objective response rate, duration of response, time to response, progression free survival and overall survival.

19. The method of claim 1, wherein the anti-CD70 antibody is administered in combination with azacitidine.

20. The method of claim 1, wherein the anti-CD70 antibody is administered in combination with venetoclax.

21. The method of claim 1, wherein the anti-CD70 antibody is administered in combination with azacitidine and venetoclax.

22. The method of claim 1, wherein the anti-CD70 antibody is administered in combination with fluoroquinalone.

* * * * *

SEQUENCE LISTING

<160> NUMBER OF SEQ ID NOS: 7

<210> SEQ ID NO 1
<211> LENGTH: 118
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115
```

<210> SEQ ID NO 2
<211> LENGTH: 111
<212> TYPE: PRT
<213> ORGANISM: Artificial Sequence
<220> FEATURE:
<223> OTHER INFORMATION: Synthetic Construct

<400> SEQUENCE: 2

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gly Gly Thr Lys Val Glu Ile Lys
            100                 105                 110
```

<210> SEQ ID NO 3
<211> LENGTH: 112
<212> TYPE: PRT
<213> ORGANISM: Artificial Sequence
<220> FEATURE:
<223> OTHER INFORMATION: Synthetic Construct

<400> SEQUENCE: 3

```
Asp Ile Val Met Thr Gln Ser Pro Asp Ser Leu Ala Val Ser Leu Gly
1               5                   10                  15
```

```
Glu Arg Ala Thr Ile Asn Cys Arg Ala Ser Lys Ser Val Ser Thr Ser
                20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Val Pro Trp Thr Phe Gly Gln Gly Thr Lys Val Glu Ile Lys Arg
            100                 105                 110
```

<210> SEQ ID NO 4
<211> LENGTH: 448
<212> TYPE: PRT
<213> ORGANISM: Artificial Sequence
<220> FEATURE:
<223> OTHER INFORMATION: Synthetic Construct

<400> SEQUENCE: 4

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Tyr Thr Gly Glu Pro Thr Tyr Ala Asp Ala Phe
 50                  55                  60

Lys Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Tyr Gly Asp Tyr Gly Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 5
<211> LENGTH: 218
<212> TYPE: PRT
<213> ORGANISM: Artificial Sequence
<220> FEATURE:
<223> OTHER INFORMATION: Synthetic Construct

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 6
<211> LENGTH: 330
<212> TYPE: PRT
<213> ORGANISM: Artificial Sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 7
<211> LENGTH: 106
<212> TYPE: PRT
<213> ORGANISM: Artificial Sequence
<220> FEATURE:
<223> OTHER INFORMATION: Synthetic Construct

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```